US010454037B2

(12) United States Patent
Vladimirov et al.

(10) Patent No.: US 10,454,037 B2
(45) Date of Patent: *Oct. 22, 2019

(54) ORGANIC SEMICONDUCTOR COMPOSITION COMPRISING A LIQUID MEDIUM

(71) Applicant: BASF SE, Ludwigshafen (DE)

(72) Inventors: Ilja Vladimirov, Mannheim (DE); Jochen Brill, Speyer (DE); Dieter Freyberg, Einselthum (DE); Thomas Weitz, Mannheim (DE); Thomas Musiol, Maxdorf (DE); Silke Annika Koehler, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/504,851

(22) PCT Filed: Aug. 17, 2015

(86) PCT No.: PCT/IB2015/056248
§ 371 (c)(1),
(2) Date: Feb. 17, 2017

(87) PCT Pub. No.: WO2016/027217
PCT Pub. Date: Feb. 25, 2016

(65) Prior Publication Data
US 2017/0250347 A1 Aug. 31, 2017

(30) Foreign Application Priority Data
Aug. 18, 2014 (EP) ..................... 14181269

(51) Int. Cl.
*C09K 11/00* (2006.01)
*H01L 51/00* (2006.01)
*C07D 471/06* (2006.01)
*H01L 51/05* (2006.01)
*H01L 51/42* (2006.01)
*H01L 51/50* (2006.01)

(52) U.S. Cl.
CPC ........ H01L 51/0053 (2013.01); C07D 471/06 (2013.01); H01L 51/0004 (2013.01); H01L 51/0005 (2013.01); H01L 51/0007 (2013.01); H01L 51/0035 (2013.01); H01L 51/0074 (2013.01); *H01L 51/0558* (2013.01); *H01L 51/4253* (2013.01); *H01L 51/5012* (2013.01); *Y02E 10/549* (2013.01); *Y02P 70/521* (2015.11)

(58) Field of Classification Search
CPC ......... C09K 11/06; H01L 51/00; H01L 31/20; C07D 471/08
USPC ............ 252/301.26; 313/498, 504; 136/252; 546/37, 66
See application file for complete search history.

(56) References Cited

U.S. PATENT DOCUMENTS

| 4,461,922 A | 7/1984 | Gay et al. |
|---|---|---|
| 4,539,507 A | 9/1985 | VanSlyke et al. |
| 4,678,608 A * | 7/1987 | Dugliss ................ C09K 11/00 252/700 |
| 4,720,432 A | 1/1988 | VanSlyke et al. |
| 4,769,292 A | 9/1988 | Tang et al. |
| 5,324,853 A | 6/1994 | Jones et al. |
| 6,198,091 B1 | 3/2001 | Forrest et al. |
| 6,198,092 B1 | 3/2001 | Bulovic et al. |
| 6,310,235 B1 | 10/2001 | Gick |
| 6,451,415 B1 | 9/2002 | Forrest et al. |
| 6,864,396 B2 | 3/2005 | Smith et al. |
| 7,569,693 B2 | 8/2009 | Marks et al. |
| 7,671,202 B2 | 3/2010 | Marks et al. |
| 7,674,406 B2 * | 3/2010 | Bindra et al. ............ C09K 3/00 252/700 |
| 7,902,363 B2 | 3/2011 | Facchetti et al. |
| 9,442,401 B2 * | 9/2016 | Sekido ................. G03G 5/14 |
| 2003/0100779 A1 | 5/2003 | Vogel et al. |
| 2003/0111649 A1 * | 6/2003 | Park et al. ............ C09K 3/00 252/700 |
| 2004/0046182 A1 | 3/2004 | Chen et al. |
| 2005/0098726 A1 | 5/2005 | Peumans et al. |
| 2005/0224905 A1 | 10/2005 | Forrest et al. |
| 2006/0202195 A1 | 9/2006 | Marks et al. |
| 2010/0319778 A1 | 12/2010 | Kastler et al. |
| 2012/0256137 A1 | 10/2012 | James et al. |
| 2013/0026421 A1 | 1/2013 | James et al. |
| 2014/0042369 A1 | 2/2014 | Huang et al. |

(Continued)

FOREIGN PATENT DOCUMENTS

| DE | 1 945 359 A1 | 3/1971 |
| DE | 26 12 355 A1 | 10/1977 |

(Continued)

OTHER PUBLICATIONS

Valery A. Postnikov, et al., "Molecularly Smooth Single-Crystalline Films of Thiophene-Phenylene Co-Oligomers Grown at the Gas-Liquid Interface", Crystal Growth and Design, vol. 14, 2014, pp. 1726-1737.

(Continued)

*Primary Examiner* — Charanjit Aulakh

(74) *Attorney, Agent, or Firm* — Oblon, McClelland, Maier & Neustadt, L.L.P.

(57) ABSTRACT

Disclosed are a novel semiconductor composition comprising at least one organic semiconductor in a liquid medium and the use thereof the production of organic semiconductor devices, in particular organic field effect transistors, organic solar cells, light-emitting diodes and sensors.

19 Claims, 10 Drawing Sheets

(56) References Cited

U.S. PATENT DOCUMENTS

2014/0218452 A1  8/2014  Li et al.
2015/0144845 A1  5/2015  Suzuki et al.
2015/0188053 A1  7/2015  Newsome

FOREIGN PATENT DOCUMENTS

| | | |
|---|---|---|
| EP | 0 387 715 A2 | 9/1990 |
| EP | 0 532 798 A1 | 3/1993 |
| EP | 1 266 882 A1 | 12/2002 |
| EP | 2 077 590 A1 | 7/2009 |
| JP | 2009-78963 A | 4/2009 |
| JP | 2009-283786 A | 12/2009 |
| JP | 2011-522097 A | 7/2011 |
| JP | 2014 51476 A | 3/2014 |
| JP | 2014-139143 A | 7/2014 |
| JP | 2015-173210 | 10/2015 |
| WO | WO 99/32427 A1 | 7/1999 |
| WO | WO 00/70655 A2 | 11/2000 |
| WO | WO 02/38531 A1 | 5/2002 |
| WO | WO 02/100536 A1 | 12/2002 |
| WO | WO 03/029168 A2 | 4/2003 |
| WO | WO 03/029181 A1 | 4/2003 |
| WO | WO 2004/009526 A1 | 1/2004 |
| WO | WO 2005/019373 A2 | 3/2005 |
| WO | WO 2007/093643 A1 | 8/2007 |
| WO | WO 2007/116001 A2 | 10/2007 |
| WO | WO 2011/023490 A1 | 3/2011 |
| WO | WO 2011/023491 A1 | 3/2011 |
| WO | WO 2011/076324 A1 | 6/2011 |
| WO | WO 2011/082991 A2 | 7/2011 |
| WO | WO 2011/128035 A1 | 10/2011 |
| WO | WO 2012/090110 A1 | 7/2012 |
| WO | WO 2012/113608 A1 | 8/2012 |
| WO | WO 2012/113609 A1 | 8/2012 |
| WO | WO 2013/187275 A1 | 12/2013 |
| WO | WO 2013/190255 A2 | 12/2013 |
| WO | WO 2014/038708 A1 | 3/2014 |
| WO | WO 2014/087300 A1 | 6/2014 |
| WO | WO 2015/128779 A1 | 9/2015 |

OTHER PUBLICATIONS

Hiromi Minemawari, et al., "Inkjet printing of single-crystal films", Nature, vol. 475, Jul. 21, 2011, pp. 364-367.
International Search Report dated Dec. 25, 2015 in PCT/IB2015/056248.
International Preliminary Report on Patentability and Written Opinion dated Feb. 21, 2017 in PCT/IB2015/056248.

* cited by examiner figure 10a
figure 10b
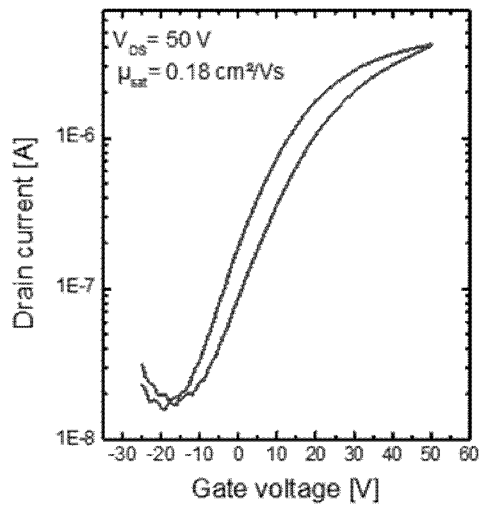
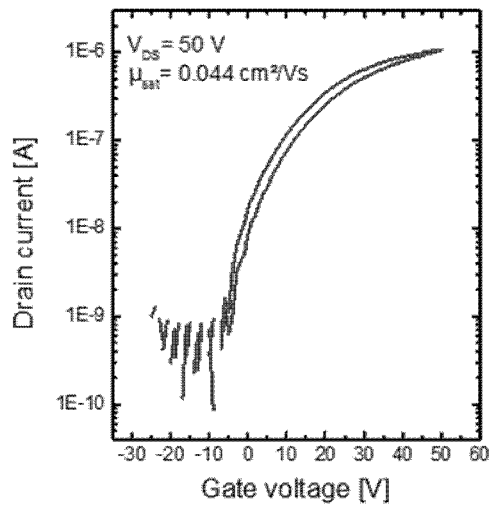

figure 14a
figure 14b
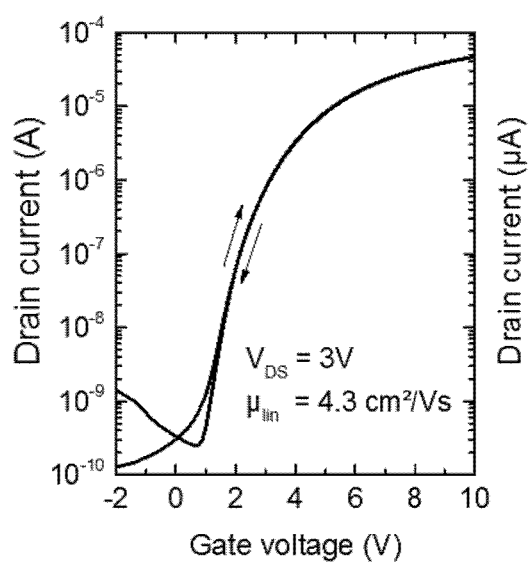
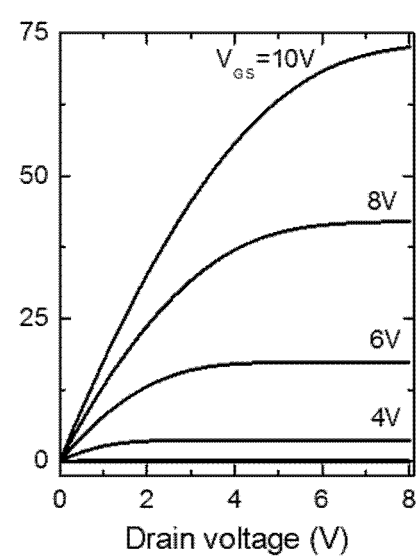

ORGANIC SEMICONDUCTOR COMPOSITION COMPRISING A LIQUID MEDIUM

CROSS-REFERENCE TO RELATED APPLICATIONS

This application is a National Stage of PCT/IB2015/056248, which was filed on Aug. 17, 2015. This application is based upon and claims the benefit of priority to European Application No. 14181269.3, which was filed on Aug. 18, 2014.

FIELD OF THE INVENTION

The present invention relates to a novel semiconductor composition comprising at least one organic semiconductor in a liquid medium and the use thereof for the production of organic semiconductor devices, in particular organic field-effect transistors, organic solar cells, light-emitting diodes and sensors.

Organic semiconductors based on low molecular weight molecules or polymeric materials are already used in many sectors of the electronics industry. In many cases, these organic semiconductors have advantages over the classical inorganic semiconductors, for example better substrate compatibility and better processability of the semiconductor components based on them. They allow processing on flexible substrates and enable their orbital energies to be adjusted precisely to the particular application range by the methods of molecular modeling. The significantly reduced costs of such components have brought an upswing to the field of research of organic electronics.

Organic electronics is concerned principally with the development of new materials and manufacturing processes for the production of electronic components based on organic semiconductor layers. These include in particular organic field-effect transistors (OFETs) and organic electroluminescent devices (hereinafter abbreviated as "EL" devices). Great potential for development is ascribed to organic field-effect transistors, for example in storage elements, backplanes and integrated optoelectronic devices. An organic electroluminescent device is a self-emission device utilizing the principle that a fluorescent material emits light by the recombination energy of holes injected from an anode and electrons injected from a cathode when an electric field is applied. EL devices in form of organic light-emitting diodes (OLEDs) are especially of interest as an alternative to cathode ray tubes and liquid-crystal displays for producing flat visual display units. Owing to the very compact design and the intrinsically low power consumption, devices which comprise OLEDs are suitable especially for mobile applications, for example for applications in cell phones, laptops, etc.

Organic photovoltaics is concerned principally with the development of new materials for organic solar cells. A great potential for development is ascribed to materials which have maximum transport widths and high mobilities for light-induced excited states (high exciton diffusion lengths) and are thus advantageously suitable for use as an active material in so-called excitonic solar cells. It is generally possible with solar cells based on such materials to achieve very good quantum yields.

Different types of chemical sensors are known, in particular electronic conductance sensors, mass-sensitive-sensors utilizing a quartz crystal microbalance, surface acoustic-wave sensors and optical sensors. Organic semiconductors with a sufficient crystal size are promising candidates for gas sensors. They are e.g. chemically sensitive to reactive gases and can be oxidized or reduced. Gas sensors have found wide application in various technical fields, e.g. in the field of work safety and environmental protection for detecting toxic or irritant gases or vapors like CO and $NO_2$, as well as in air conditioning in cars, airplanes, houses etc. to ethanol sensors for breath analyzers.

It is still a challenge to provide organic electronic devices, organic solar cells and optoelectronic devices, such as organic thin film transistors (OTFTs), OLEDs, printable circuits, capacitors, sensors etc., that have good performance properties and can be prepared by large-scale standard manufacturing processes. In particular there is still a demand for cost-effective wet-processing techniques that allow the preparation of active components comprising organic semiconductors that good application properties (e.g. high charge carrier mobilities) and are stable under ambient conditions.

Known methods for the fabrication of devices on the basis of solution-processed semiconducting films have several drawbacks. Thus, in many cases the obtained application properties, like charge carrier mobilities, still need to be improved. Further, the solvents employed in such processes have only a limited compatibility with the organic semiconductors or are environmentally harmful.

Valery A. Postnikov et al. describe in Cryst. Growth Des. 2014, 14, 1726-1737, the formation of molecularly smooth single-crystalline films of thiophene-phenylene co-oligomers (TPCOs) grown at the gas-liquid interface. Suitable techniques for the growth of single crystals at the gas-solution interface are solvent-antisolvent crystallization (SAC), isothermal slow solvent evaporation (ISSE) and isochoric cooling (IC). For SAC toluene was used as solvent and ethanol, isopropanol or mixtures thereof were used as antisolvent. For ISSE and IC toluene, hexane and chlorobenzene were employed.

H. Minemawari et al. describe in Nature, vol. 475, 21 Jul. 2011, 364-367 a method that combines the technique of antisolvent crystallization with inkjet printing to produce organic semiconducting thin films of high crystallinity. Specifically, it is shown that mixing fine droplets of an antisolvent and a solution of an active semiconducting component within a confined area on an amorphous substrate can trigger the controlled formation of uniform single-crystal or polycrystalline thin films that grow at the liquid-air interface. In all examples 1,2-dichlorobenzene is used as the solvent and N,N-dimethylformamide is used as the antisolvent.

US 2014042369 A1 describes an organic semiconductor formulation comprising an organic semiconductor in a liquid medium, wherein the liquid medium comprises a first liquid and optionally a second liquid, the first liquid being an aromatic compound having electronic properties complementary to the electronic structure of the organic semiconductor compound, and the second liquid being a solvent or solvent mixture in which the organic semiconductor has a solubility of at least about 0.1 mg/mL. Although this document names a plethora of different semiconductors and solvents the only semiconductor used in the working examples is N,N'-bis(2-ethylhexyl)-(1,7 and 1,6)-dicyanoperylene-3,4:9,10-bis(dicarboximide). The tested solvents are N,N-dimethylaniline, nitrobenzene, 2-methylanisole, xylene, dichlorobenzene and benzonitrile.

The application properties of semiconductor devices obtained from those solvents still need improvement. Furthermore, N,N-dimethylaniline and nitrobenzene are toxic and environmentally dangerous and 2-methylanisol, xylene, dichlorobenzene and benzonitrile are harmful to health.

Accordingly, there is a need in the art to develop new organic semiconductor formulations in a liquid medium that enable manufacturing of semiconductor devices with good application properties by large-scale standard processes.

It has now surprisingly been found that liquid aliphatic or aromatic carbocycles and heterocycles that bear at least two carboxylic ester groups are particularly suitable for liquid organic semiconductor compositions. They are non-hazardous, show a good compatibility with a great number of different organic semiconductors and the resulting liquid organic semiconductor formulations are suitable for the production of various semiconductor devices with good application properties. The use of said liquid aliphatic or aromatic carbocycles and heterocycles leads to the formation of thin films that exhibit excellent application properties in various field effect devices. The liquid compositions according to the invention are especially suitable for the formation of organic thin film transistors (OTFTs) by a wet-processing technique under ambient conditions. The semiconductor layers obtained from the liquid compositions according to the invention are characterized by good solid state properties, e.g. a good crystallinity. As a result, field-effect devices such as thin-film transistors that are fabricated with the semiconductor compositions usually have high performance under ambient conditions, e.g. characterized by one or more of the following properties: large charge mobilities, low threshold voltages, and high current on-off ratios.

SUMMARY OF THE INVENTION

A first object of the present invention relates to a composition comprising
A) at least one organic semiconductor selected from rylene compounds of the general formula (I.a)

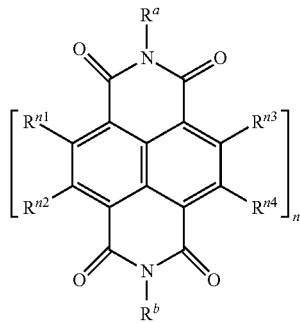

(I.a)

wherein
n is 1, 2, 3 or 4,
$R^a$ and $R^b$ are independently of one another selected from hydrogen and in each case unsubstituted or substituted alkyl, alkenyl, alkadienyl, alkynyl, cycloalkyl, bicycloalkyl, cycloalkenyl, heterocycloalkyl, aryl and heteroaryl, the $R^{n1}$, $R^{n2}$, $R^{n3}$ and $R^{n4}$ radicals are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, where $E^1$ and $E^2$ are each independently selected from hydrogen, alkyl, cycloalkyl, heterocycloalkyl, aryl or hetaryl,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino,
compounds of the formula (I.b)

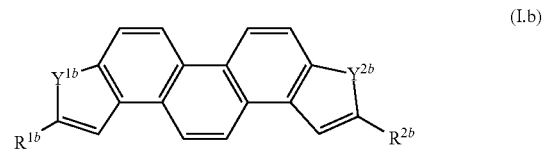

(I.b)

wherein
$R^{1b}$ and $R^{2b}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl,
$Y^{1b}$ and $Y^{2b}$ are independently selected from O, S, Se and $NR^3$, where $R^3$ is selected from hydrogen and in each case unsubstituted or substituted alkyl, cycloalkyl and aryl,
compounds of the formula (I.c)

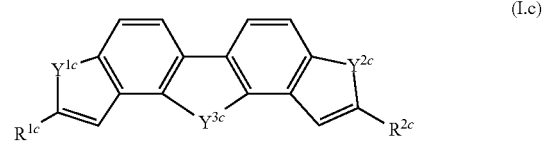

(I.c)

wherein
$R^{1c}$ and $R^{2c}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl,
$Y^{1c}$, $Y^{2c}$ and $Y^{3c}$ are independently selected from O, S, Se and $NR^{3c}$, where $R^{3c}$ is selected from hydrogen and in each case unsubstituted or substituted alkyl, cycloalkyl and aryl,
compounds of the formula (I.d)

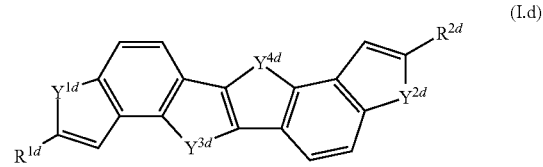

(I.d)

wherein
$R^{1d}$ and $R^{2d}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1d}$, $Y^{2d}$, $Y^{3d}$ and $Y^{4d}$ are independently selected from O, S, Se and $NR^{3d}$, where $R^{3d}$ is selected from hydrogen and in each case unsubstituted or substituted alkyl, cycloalkyl and aryl, compounds of the formula (I.e)

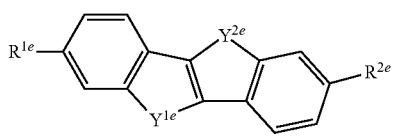

wherein
$R^{1e}$ and $R^{2e}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1e}$ and $Y^{2e}$ are independently selected from O, S, Se and $NR^{3e}$, where $R^{3e}$ is selected from hydrogen and in each case unsubstituted or substituted alkyl, cycloalkyl and aryl, B) at least one compound that is liquid at 20° C. and 1013 mbar, selected from compounds of the formula (II)

wherein
A is a 5- to 8-membered unsubstituted or substituted, aliphatic or aromatic carbocycle or heterocycle, $X^1$ and $X^2$ are independently selected from *—(C=O)—O—, *—($CH_2$)$_m$—O— or *—($CH_2$)$_m$—O—(C=O)—, where * is the point of linkage to the aliphatic or aromatic carbocycle or heterocycle, and m has the value 0, 1, or 2;

and
$R^c$ and $R^d$ are independently selected from unbranched and branched $C_1$-$C_{12}$-alkyl and $C_2$-$C_{12}$-alkenyl.

In a special embodiment, the composition according to the invention additionally comprises a cosolvent C) selected from organic solvents and mixtures of organic solvents different from component B).

A further object of the invention is a process for the preparation of an electronic device, optical device or optoelectronic device, comprising:
(a) providing a composition comprising A) at least one organic semiconductor and B) at least one compound that is liquid at 20° C. and 1013 mbar, as defined above and in the following,
(b) applying the composition provided in step (a) to at least a portion of the surface of a substrate to allow deposition of the at least one organic semiconductor on the substrate.

A further object of the invention is the use of a composition as defined above and in the following for the production of a semiconductor material, preferably a semiconductor material in organic electronics or in organic photovoltaics.

DETAILED DESCRIPTION OF THE INVENTION

Without wishing to be bound to any particular theory, it is believed that devices comprising an organic semiconductor component prepared from a composition according to the invention can exhibit improved properties because the liquid component B) is beneficial for the deposition of the organic semiconductor A) on a substrate. In particular, component B) shows an ideal balance of good solubility with respect to the semiconductors A) and a sufficient low volatility to allow the formation of semiconductor layers with excellent properties. For organic semiconductors this leads to advantageous solid state properties, like the formation of larger crystallites and a reduced number of grain boundaries. An increase in crystallinity, crystal grain size and crystalline domains of semiconductor layers deposited from a composition according to the invention can be detected by optical microscopy (see FIGS. 1a and 1b). Larger crystallites can contribute, at least in part, to improved charge transport, possibly because of the reduced number of grain boundaries which act as charge trapping sites.

In light of the foregoing, the present teachings provide organic semiconductor formulations that can exhibit properties such as tailored compatibility with a given organic semiconductor, improved long-term and chemical stability, low-temperature processability, and large processing versatility. As a result, field effect devices such as thin film transistors that are fabricated with the present semiconductor formulations can have high performance under ambient conditions, for example, demonstrating one or more of large charge mobilities, low threshold voltages, and high current on-off ratios.

In particular, the new organic semiconductor composition has at least one of the following advantages:
The composition allows the preparation of various articles, structures or devices on the basis of semiconductors A) by solution-processing.
The composition according to the invention allows the preparation of various articles, structures, or devices from semiconductors A) by solution-processing, including coating, such as spin-coating and slot dye coating and various printing techniques.
The deposition of the semiconductors A) on a substrate can be performed in a broad temperature range. In a special embodiment, the deposition of the semiconductors A) on a substrate can be performed at low temperatures, in many cases at a temperature of less than 100° C.
OFETs, in particular OTFTs produced from the semiconductor composition according to the invention are characterized by at least one of the following properties: a high charge transport mobility, a high on/off ratio, low threshold voltages and air stability.
The new organic semiconductor composition leads to advantageous solid state properties, like the formation of larger crystallites, a reduced number of grain boundaries and therefore to an improved charge transport.
OFETs, in particular OTFTs produced from the semiconductor composition according to the invention are characterized by a greater continuity of the obtained film within the channel region of the organic electronic device.
The compounds B) used according to the invention are generally non-toxic.

The expression "halogen" denotes in each case fluorine, bromine, chlorine or iodine, particularly chlorine, bromide or iodine.

In the context of the invention, the expression "unsubstituted or substituted alkyl, cycloalkyl, heterocycloalkyl, aryl and hetaryl" represents unsubstituted or substituted alkyl, unsubstituted or substituted cycloalkyl, unsubstituted or substituted heterocycloalkyl, unsubstituted or substituted aryl and unsubstituted or substituted hetaryl.

In the context of the invention, the expression "in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl," represents unsubstituted or substituted linear $C_1$-$C_{30}$-alkyl, unsubstituted or substituted branched $C_3$-$C_{30}$-alkyl, unsubstituted or substituted linear $C_2$-$C_{30}$-alkenyl, unsubstituted or substituted branched $C_3$-$C_{30}$-alkenyl, unsubstituted or substituted linear $C_2$-$C_{30}$-alkinyl, unsubstituted or substituted branched $C_4$-$C_{30}$-alkinyl, unsubstituted or substituted cycloalkyl, unsubstituted or substituted aryl and unsubstituted or substituted hetaryl.

In the context of the invention, the expression "in each case unsubstituted or substituted alkyl, cycloalkyl and aryl" represents unsubstituted or substituted alkyl, unsubstituted or substituted cycloalkyl and unsubstituted or substituted aryl.

In the context of the invention, the expression "unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino" represents unsubstituted or substituted alkyl, unsubstituted or substituted alkoxy, unsubstituted or substituted alkylthio, unsubstituted or substituted (monoalkyl)amino, unsubstituted or substituted (dialkyl)amino, unsubstituted or substituted cycloalkyl, unsubstituted or substituted cycloalkoxy, unsubstituted or substituted cycloalkylthio, unsubstituted or substituted (monocycloalkyl)amino, unsubstituted or substituted (dicycloalkyl)amino, unsubstituted or substituted heterocycloalkyl, unsubstituted or substituted heterocycloalkoxy, unsubstituted or substituted heterocycloalkylthio, unsubstituted or substituted (monoheterocycloalkyl)amino, unsubstituted or substituted (diheterocycloalkyl)amino, unsubstituted or substituted aryl, unsubstituted or substituted aryloxy, unsubstituted or substituted arylthio, unsubstituted or substituted (monoaryl)amino, unsubstituted or substituted (diaryl)amino, unsubstituted or substituted hetaryl, unsubstituted or substituted hetaryloxy, unsubstituted or substituted hetarylthio, unsubstituted or substituted (monohetaryl)amino and unsubstituted or substituted (dihetaryl)amino.

In the context of the present invention, the expression "alkyl" comprises straight-chain or branched alkyl groups. Alkyl is preferably $C_1$-$C_{30}$-alkyl, more preferably $C_1$-$C_{22}$-alkyl. Short chain alkyl groups are preferably selected from $C_1$-$C_6$-alkyl groups. Long chain alkyl groups are preferably selected from $C_7$-$C_{22}$-alkyl groups. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propyl pentyl, 2-propylpentyl, n-nonyl, 1-methyloctyl, 2-methyloctyl, 1-ethylheptyl, 2-ethylheptyl, 1-propylhexyl, 2-propylhexyl, 1-butylpentyl, n-decyl, 2-methyldecyl, 1-methylnonyl, 2-methylnonyl, 1-ethyloctyl, 2-ethyloctyl, 1-propylheptyl, 2-propylheptyl, 1-butylhexyl, 2-butylhexyl, n-undecyl, 2-ethylnonyl, 1-propyloctyl, 2-propyloctyl, 1-butylheptyl, 2-butylheptyl, 1-pentylhexyl, n-dodecyl, 2-ethyldecyl, 2-propylnonyl, 1-butyloctyl, 2-butyloctyl, 1-pentylheptyl, 2-pentylheptyl, 2-propyldecyl, n-tridecyl, 1-pentyloctyl, 2-pentyloctyl, 1-hexylheptyl, 2-butylnonyl, n-tetradecyl, 1-hexyloctyl, 2-hexyloctyl, 2-pentylnonyl, 2-hexylnonyl, 2-pentyldecyl, 2-butyldecyl, n-hexadecyl, 1-heptyloctyl, 2-heptylnonyl, 2-hexyldecyl, 2-heptyldecyl, n-octadecyl, 2-octyldecyl, n-eicosyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-methyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl and 2-methyloctacosanyl.

The expression alkyl also comprises alkyl radicals whose carbon chains may be interrupted by one or more nonadjacent groups which are selected from —O—, —S—, —NR$^a$—, —C(=O)—, —S(=O)— and/or —S(=O)$_2$—. R$^a$ is preferably hydrogen, alkyl, cycloalkyl, heterocycloalkyl, aryl or hetaryl.

Examples of alkyl groups whose carbon chains are interrupted by one or more nonadjacent groups are especially 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-ropylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl; 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl; (1-ethylethylidene)aminoethylene, (1-ethylethylidene)aminopropylene, (1-ethylethylidene)aminobutylene, (1-ethylethylidene)aminodecylene and (1-ethylethylidene)aminododecylene; propan-2-on-1-yl, butan-3-on-1-yl, butan-3-on-2-yl and 2-ethylpentan-3-on-1-yl; 2-methylsulfoxidoethyl, 2-ethylsulfoxidoethyl, 2-propylsulfoxidoethyl, 2-isopropylsulf-oxidoethyl, 2-butylsulfoxidoethyl, 2- and 3-methylsulfoxidopropyl, 2- and 3-ethylsulf-oxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl; 2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^5E^6$ where $E^5$ and $E^6$ are each independently hydrogen, alkyl, cycloalkyl, heterocycloalkyl, aryl or hetaryl. Cycloalkyl, heterocycloalkyl, aryl and hetaryl substituents of the alkyl groups may in turn be unsubstituted or substituted; suitable substituents are the substituents mentioned below for these groups. Special embodiments of substituted alkyl groups are perfluoro-$C_1$-$C_{30}$-alkyl, 1H,1H-perfluoro-$C_2$-$C_{30}$-alkyl and 1H,1H,2H,2H-perfluoro-$C_3$-$C_{30}$-alkyl. Examples for those fluorinated alkyl groups are mentioned in the following.

Examples of substituted alkyl groups are especially carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxy-tetradecyl; sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl; 2-hydroxyethyl, 2- and 3-hydroxypropyl, 1-hydroxyprop-2-yl, 3- and 4-hydroxybutyl, 1-hydroxybut-2-yland 8-hydroxy-4-oxaoctyl; 2-cyanoethyl, 3-cyanopropyl, 2- and 4-cyanobutyl, 2-methyl-3-ethyl-3-cyanopropyl, 7-cyano-7-ethylheptyl and 4,7-dimethyl-7-cyanoheptyl; 2-chloroethyl, 2- and 3-chloropropyl, 2-, 3- and 4-chlorobutyl, 2-bromoethyl, 2- and 3-bromopropyl and 2-, 3- and 4-bromobutyl; 2-nitroethyl, 2- and 3-nitropropyl and 2-, 3- and 4-nitrobutyl.

Carboxylate and sulfonate respectively represent a derivative of a carboxylic acid function and a sulfonic acid function, especially a metal carboxylate or sulfonate, a carboxylic ester or sulfonic ester function or a carboxamide or sulfonamide function. Such derivatives include, for example, esters with $C_1$-$C_4$-alkanols, such as methanol, ethanol, n-propanol, isopropanol, n-butanol, sec-butanol and tert-butanol.

The above remarks regarding alkyl also apply to the alkyl moiety in alkoxy, alkylthio (=alkylsulfanyl), monoalkylamino and dialkylamino.

Examples of alkoxy groups are especially methoxy, ethoxy, propoxy, isopropoxy, butoxy, isobutoxy, sec-butoxy, tert-butoxy, pentoxy, isopentoxy, neopentoxy, tert-pentoxy and hexoxy.

Examples of alkylthio groups are especially methylthio, ethylthio, propylthio, isopropylthio, butylthio, isobutylthio, sec-butylthio, tert-butylthio, pentylthio, isopentylthio, neopentylthio, tert-pentylthio and hexylthio.

Examples of monoalkylamino groups and dialkylamino groups are especially methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

Alkylene represents a linear saturated hydrocarbon chain having from 1 to 10 and especially from 1 to 4 carbon atoms, such as ethane-1,2-diyl, propane-1,3-diyl, butane-1,4-diyl, pentane-1,5-diyl or hexane-1,6-diyl.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^7E^8$ where $E^7$ and $E^8$ are each independently hydrogen, alkyl, cycloalkyl, heterocycloalkyl, aryl or hetaryl. In the case of substitution, the cycloalkyl groups preferably bear one or more, for example one, two, three, four or five, $C_1$-$C_6$-alkyl groups. Examples of substituted cycloalkyl groups are especially 2- and 3-methyl-cyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methyl-cyclooctyl, 2-, 3-, 4- and 5-ethylcyclooctyl, 2-, 3-, 4- and 5-propylcyclooctyl, 3- and 4-hydroxycyclohexyl, 3- and 4-nitrocyclohexyl and 3- and 4-chlorocyclohexyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the term "aryl" refers to mono- or polycyclic aromatic hydrocarbon radicals. Aryl usually is an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl.

Substituted aryls may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^9E^{10}$ where $E^9$ and $E^{10}$ are each independently hydrogen, alkyl, cycloalkyl, heterocycloalkyl, aryl or hetaryl. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, (2-chloro-6-methyl)phenyl, (2-chloro-6-ethyl)phenyl, (4-chloro-6-methyl)phenyl, (4-chloro-6-ethyl)phenyl.

The above remarks regarding aryl also apply to the aryl moiety in aryloxy, arylthio (=arylsulfanyl), monoarylamino and diarylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —$NR^b$—, —C(=O)—, —S(=O)— and/or —S(=O)$_2$—. $R^b$ is preferably hydrogen, alkyl, cycloalkyl, heterocycloalkyl, aryl or hetaryl. Examples of heterocycloalkyl groups are especially pyrrolidinyl, piperidinyl, 2,2,6,6-tetramethylpiperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^{11}E^{12}$ where $E^{11}$ and $E^{12}$ are each independently hydrogen, alkyl, cycloalkyl, heterocycloalkyl, aryl or hetaryl. In the case of substitution, the heterocycloalkyl groups preferably bear one or more, for example one, two, three, four or five, $C_1$-$C_6$-alkyl groups.

The above remarks regarding heterocycloalkyl also apply to the heterocycloalkyl moiety in heterocycloalkoxy, heterocycloalkylthio (=heterocycloalkylsulfanyl), monoheterocycloalkylamino and diheterocycloalkylamino.

In the context of the present invention, the expression "hetaryl" (heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^{13}E^{14}$ where $E^{13}$ and $E^{14}$ are each independently hydrogen, alkyl, cycloalkyl, heterocycloalkyl, aryl or hetaryl. Halogen substituents are preferably fluorine, chlorine or bromine. The substituents are preferably selected from $C_1$-$C_6$-alkyl, $C_1$-$C_6$-alkoxy, hydroxyl, carboxyl, halogen and cyano.

The above remarks regarding hetaryl also apply to the hetaryl moiety in hetaryloxy, hetarylthio, monohetarylamino and dihetarylamino.

For the purposes of the present invention, the expression "acyl" refers to alkanoyl or aroyl groups which generally have from 2 to 11, preferably from 2 to 8, carbon atoms, for example the acetyl, propanoyl, butanoyl, pentanoyl, hexanoyl, heptanoyl-, 2-ethyl-hexanoyl, 2-propylheptanoyl, pivaloyl, benzoyl or naphthoyl group.

The groups $NE^1E^2$, $NE^3E^4$, $NE^5E^6$, $NE^7E^8$, $NE^9E^{10}$, $NE^{11}E^{12}$ and $NE^{13}E^{14}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

Component A)

A skilled person will readily appreciate that the compounds (A) may be present in pure form or comprising the respective depicted compound and at least one structural isomer thereof.

In the compounds of the formula I, n denotes the number of naphthalene units which are bonded in the peri position and form the base skeleton of the inventive rylene compounds. The rylene compounds according to the invention do not only encompass rylene diimides but also the structurally close related naphthalene diimides (n=1). In the individual $R'''^1$ to $R'''^4$ radicals, n denotes the particular naphthalene group of the rylene skeleton to which the radicals are bonded. $R'''^1$ to $R'''^4$ radicals which are bonded to different naphthalene groups may each have identical or different definitions. Accordingly, the compounds of the general formula I may be naphthalene diimides, perylenediimides, terrylenediimides or quaterrylenediimides of the following formulae:

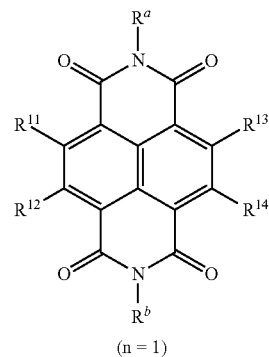

(n = 1)

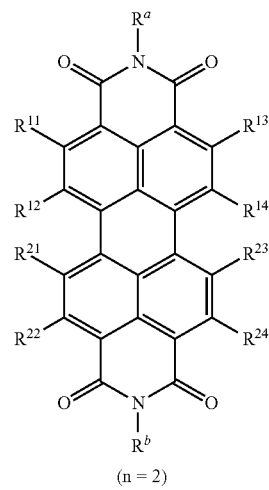

(n = 2)

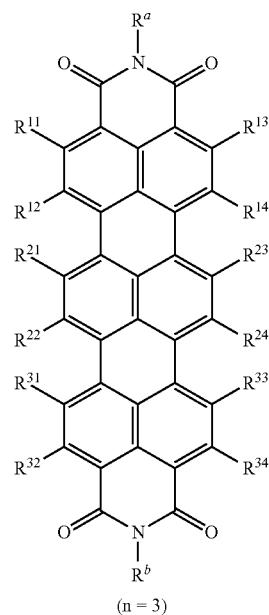

(n = 3)

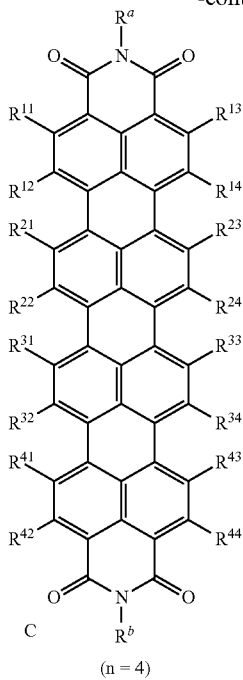

(n = 4)

Preferably, in the compounds of the formula I the radicals $R^a$ and $R^b$ are independently of one another selected from hydrogen, linear $C_1$-$C_{30}$-alkyl, branched $C_3$-$C_{30}$-alkyl, perfluoro-$C_1$-$C_{30}$-alkyl, 1H,1H-perfluoro-$C_2$-$C_{30}$-alkyl, 1H,1H,2H,2H-perfluoro-$C_1$-$C_{30}$-alkyl, a radical of the formula G.1, a radical of the formula G.2 and a radical of the formula G.3

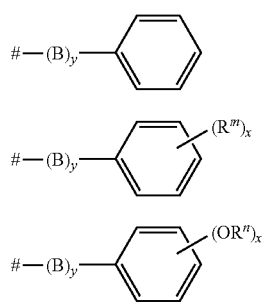

where
# represents the bonding side to a nitrogen atom,
B where present, is a $C_1$-$C_{10}$-alkylene group which may be interrupted by one or more nonadjacent groups which are selected from —O— and —S—,
y is 0 or 1,
$R^m$ is independently of one another selected from $C_1$-$C_{30}$-alkyl, $C_1$-$C_{30}$-fluoroalkyl, fluorine, chlorine, bromine, $NE^3E^4$, nitro and cyano, where $E^3$ and $E^4$, independently of one another, are hydrogen, alkyl, cycloalkyl, heterocycloalkyl, aryl or hetaryl,
$R^n$ is independently of one another selected from $C_1$-$C_{30}$-alkyl,
x in formulae G.2 and G.3 is 1, 2, 3, 4 or 5.
In a preferred embodiment of the compounds (I), the radicals $R^a$ and $R^b$ are independently selected from radicals of the general formulae (G.1) (G.2) and (G.3). In particular, $R^a$ and $R^b$ have the same meaning and are selected from radicals of the general formulae (G.1) (G.2) and (G.3).

Preferably, in the formula (G.2) the $R^m$ radicals are selected from $C_1$-$C_{12}$-alkyl or $C_1$-$C_{12}$-fluoroalkyl. In particular, in the formula (G.2) the $R^m$ radicals are selected from $C_1$-$C_4$-alkyl or $C_1$-$C_4$-fluoroalkyl.

Preferably, in the formula (G.3) the $R^n$ radicals are selected from $C_1$-$C_{12}$-alkyl.

In a preferred embodiment, in the compounds of the formula (I) $R^a$ and $R^b$ are each independently selected from radicals of the formula (G.2). Preferably, $R^a$ and $R^b$ are each independently selected from phenyl-($C_1$-$C_{30}$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{30}$-alkyl and the phenylalkyl group is attached to the imide nitrogen atom via the alkyl moiety of the phenylalkyl group.

More preferably, $R^a$ and $R^b$ have the same meaning and are selected from phenyl-($C_1$-$C_{30}$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{30}$-alkyl. In particular, $R^a$ and $R^b$ have the same meaning and are selected from phenyl-($C_1$-$C_4$)-alkyl groups, wherein the benzene ring of the phenylalkyl group bears 1, 2, 3, 4 or 5 substituents, independently selected from F, Cl, Br, CN, $C_1$-$C_{30}$-alkyl and perfluoro-$C_1$-$C_{12}$-alkyl.

Examples of preferred radicals of the formula (G.1) are mentioned in the following table 1. In a preferred embodiment, in the compounds of the formula (I) $R^a$ and $R^b$ are each independently selected from radicals of the formula (G.1) mentioned in the following table 1. In particular, $R^a$ and $R^b$ have the same meaning and are selected from radicals of the formula (G.1) mentioned in the following table 1.

Table 1 (preferred radicals of the formula G.1):

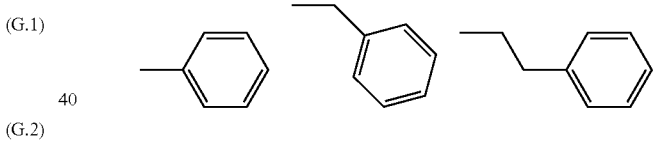

Examples of preferred radicals of the formula (G.2) are mentioned in the following table 2. In a preferred embodiment, in the compounds of the formula (I) $R^a$ and $R^b$ are each independently selected from radicals of the formula (G.2) mentioned in the following table 2. In particular, $R^a$ and $R^b$ have the same meaning and are selected from radicals of the formula (G.2) mentioned in the following table 2.

Table 2 (preferred radicals of the formula G.2):

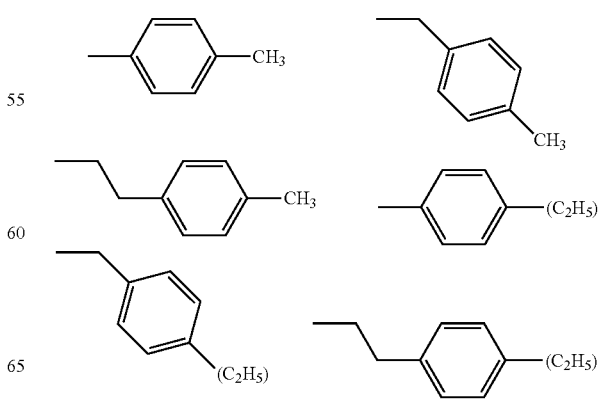

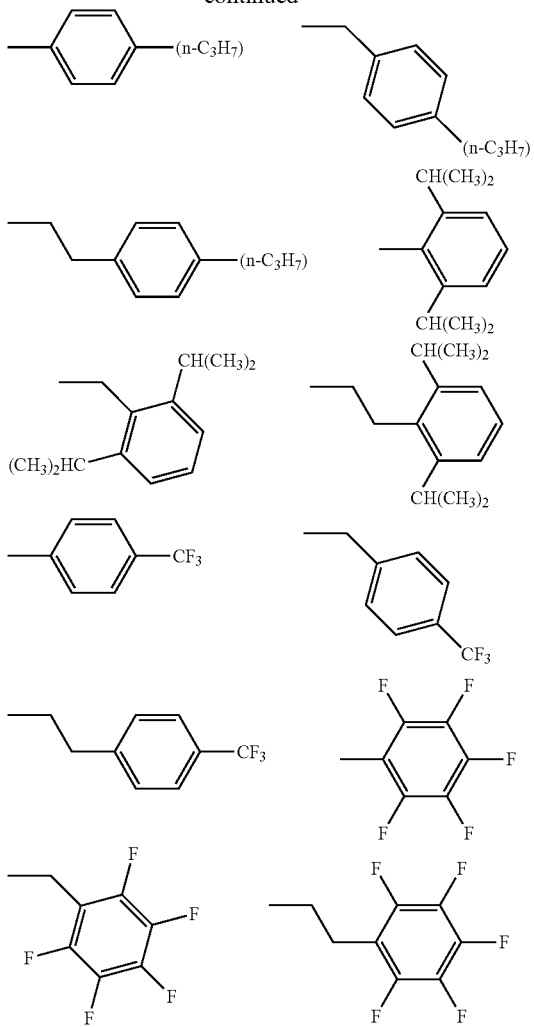

In a preferred embodiment, $R^a$ and $R^b$ are each independently selected from linear $C_1$-$C_{30}$-alkyl radicals. In particular, $R^a$ and $R^b$ have the same meaning and are selected from linear $C_1$-$C_{30}$-alkyl radicals. Preferred linear alkyl groups are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

In a preferred embodiment, $R^a$ and $R^b$ are each independently selected from branched $C_3$-$C_{30}$-alkyl radicals. In particular, $R^a$ and $R^b$ have the same meaning and are selected from branched $C_3$-$C_{30}$-alkyl radicals.

Preferably, in the compounds of the formula I the radicals $R^a$ and $R^b$ are selected from radicals of the general formulae (III.1), (III.2) and (III.3)

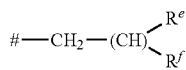 (III.1)

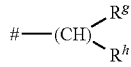 (III.2)

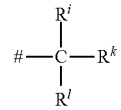 (III.3)

wherein
# is a bonding site, and
in the formula (III.1) $R^e$ and $R^f$ are independently selected from $C_1$- to $C_{27}$-alkyl, where the sum of the carbon atoms of the $R^e$ and $R^f$ radicals is an integer from 2 to 28,
in the formula (III.2) $R^g$ and $R^h$ are independently selected from $C_1$- to $C_{28}$-alkyl, where the sum of the carbon atoms of the $R^g$ and $R^h$ radicals is an integer from 2 to 29,
in the formula (III.3) $R^i$, $R^k$ and $R^l$ are independently selected from $C_1$- to $C_{27}$-alkyl, where the sum of the carbon atoms of the R, $R^k$ and $R^l$ radicals is an integer from 3 to 29.

Preferably, in the formula (III.1), $R^e$ and $R^f$ are independently selected from $C_1$- to $C_{20}$-alkyl, especially $C_1$- to $C_{12}$-alkyl.

Preferably, in the formula (III.1), the sum of the carbon atoms of the radicals (III.1) is an integer from 3 to 55, more preferably from 4 to 40, in particular from 5 to 30.

Preferred radicals of the formula (III.1) are:
2-methylpropyl, 2-ethylbutyl, 2-methylbutyl, 2-propylpentyl, 2-ethylpentyl, 2-methylpentyl, 2-butylhexyl, 2-propylhexyl, 2-ethylhexyl, 2-methylhexyl, 2-pentylheptyl, 2-butylheptyl, 2-propylheptyl, 2-ethylheptyl, 2-methylheptyl, 2-hexyloctyl, 2-pentyloctyl, 2-butyloctyl, 2-propyloctyl, 2-ethyloctyl, 2-methyloctyl, 2-heptylnonyl, 2-hexylnonyl, 2-pentylnonyl, 2-butylnonyl, 2-propylnonyl, 2-ethylnonyl, 2-methylnonyl, 2-octyldecyl, 2-heptyldecyl, 2-hexyldecyl, 2-pentyldecyl, 2-butyldecyl, 2-propyldecyl, 2-ethyldecyl, 2-methyldecyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-m ethyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-hexadecyloctadecyl, 2-pentadecyloctadecyl, 2-tetradecyloctadecyl, 2-tridecyloctadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-octadecyleicosanyl, 2-heptadecyleicosanyl, 2-hexadecyleicosanyl, 2-pentadecyleicosanyl, 2-tetradecyleicosanyl, 2-tridecyleicosanyl, 2-dodecyleicosanyl, 2-undecyleicosanyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-eicosanyldocosanyl, 2-nonadecyldocosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-nonadecyltetracosanyl, 2-octadecyltetracosanyl, 2-heptadecyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-hexacosanyloctacosanyl, 2-pentacosanyloctacosanyl, 2-tetracosanyloctacosanyl, 2-tricosanyloctacosanyl, 2-docosanyloctacosanyl, 2-nonadecyloctacosanyl, 2-octadecyloctacosanyl, 2-heptadecyloctacosanyl, 2-hexadecyloctacosanyl, 2-hexadecyloctacosanyl, 2-pentadecyloctacosanyl, 2-tetradecyloctacosanyl, 2-tridecyloctacosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl, 2-methyloctacosanyl.

Examples of preferred radicals of the formula (III.1) are 2-ethylhexyl, 2-ethylheptyl, 2-ethyloctyl, 2-ethylnonyl and 2-ethyldecyl.

In a preferred embodiment of the compounds (I.a), the radicals $R^a$ and $R^b$ are each independently selected from radicals of the formula (III.2). In particular, $R^a$ and $R^b$ have the same meaning and are selected from radicals of the formula (III.2).

Preferred radicals of the formula (III.2) are:
1-ethylpropyl, 1-methylpropyl, 1-propylbutyl, 1-ethylbutyl, 1-methylbutyl, 1-butylpentyl, 1-propylpentyl, 1-ethyl pentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethyl heptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-heptyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl.

Particularly preferred radicals of the formula (III.2) are: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butyl pentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

In a preferred embodiment of the compounds (I.a), the radicals $R^a$ and $R^b$ are each independently selected from radicals of the formula (III.3). In particular, $R^a$ and $R^b$ have the same meaning and are selected from radicals of the formula (III.3).

A particularly preferred radical of the formula (III.3) is tert.-butyl.

Preferably at least one of the radicals $R^a$ and $R^b$ is selected from perfluoro-$C_1$-$C_{30}$-alkyl, 1H,1H-perfluoro-$C_2$-$C_{30}$-alkyl or 1H,1H,2H,2H-perfluoro-$C_3$-$C_{30}$-alkyl.

In a preferred embodiment of the compounds (I.a), the radicals $R^a$ and $R^b$ are selected from perfluoro-$C_1$-$C_{30}$-alkyl, 1H,1H-perfluoro-$C_2$-$C_{30}$-alkyl or 1H,1H,2H,2H-perfluoro-$C_3$-$C_{30}$-alkyl.

In a preferred embodiment, at least one of the radicals $R^a$ and $R^b$ is selected from $CF_3$, $C_2F_5$, n-$C_3F_7$, n-$C_4F_9$, n-$C_5F_{11}$, n-$C_6F_{13}$, $CF(CF_3)_2$, $C(CF_3)_3$, $CF_2CF(CF_3)_2$, $CF(CF_3)(C_2F_5)$, $CH_2$—$CF_3$, $CH_2$—$C_2F_5$, $CH_2$-(n-$C_3F_7$), $CH_2$-(n-$C_4F_9$), $CH_2$-(n-$C_5F_{11}$), $CH_2$-(n-$C_6F_{13}$), $CH_2$—$CF(CF_3)_2$, CH$_2$—C(CF$_3$)$_3$, CH$_2$—CF$_2$CF(CF$_3$)$_2$, CH$_2$—CF(CF$_3$)(C$_2$F$_5$), CH$_2$—CH$_2$—CF$_3$, CH$_2$—CH$_2$—C$_2$F$_5$, CH$_2$—CH$_2$-(n-C$_3$F$_7$), CH$_2$—CH$_2$-(n-C$_4$F$_9$), CH$_2$—CH$_2$-(n-C$_5$F$_{11}$), CH$_2$—CH$_2$-(n-C$_6$F$_{13}$), CH$_2$—CH$_2$—CF(CF$_3$)$_2$, CH$_2$—CH$_2$—C(CF$_3$)$_3$, CH$_2$—CH$_2$—CF$_2$CF(CF$_3$)$_2$ and CH$_2$—CH$_2$—CF(CF$_3$)(C$_2$F$_5$). In particular, R$^a$ and R$^b$ have the same meaning and are selected from the afore-mentioned radicals.

It has been found that semiconductors prepared from an enantiomerically enriched mixture or an enantiomerically pure rylene compound of the general formula (I.a) can have advantageous properties. WO 2012/090110 describes enantiomerically enriched mixtures that have unexpected electron-transport efficiency compared to the racemate or either of the enantiomers in optically pure form. The teaching of this document is incorporated herein by reference.

In particular, the substituents R$^a$ and R$^b$ are identical and selected from a branched C$_{4-40}$ alkyl group, a branched C$_{4-40}$ alkenyl group and a branched C$_{4-40}$ haloalkyl group, wherein the branched C$_{4-40}$ alkyl group, the branched C$_{4-40}$ alkenyl group, or the branched C$_{4-40}$ haloalkyl group are selected from:

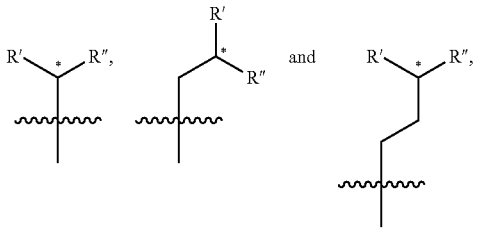

where R' is a C$_{1-20}$ alkyl or haloalkyl group; and R" is different from R' and selected from a C$_{1-20}$ alkyl group, a C$_{2-20}$ alkenyl group, and a C$_{1-20}$ haloalkyl group. The asterisk * denotes a stereogenic center such that R$^a$ and R$^b$ have either an (R)- or an (S)-configuration. In a preferred embodiment, the mixture is enantiomerically enriched, that is, the mixture includes an excess of either the (R,R)-stereoisomer (in which both R$^a$ and R$^b$ have the (R)-configuration) or the (S,S)-stereoisomer (in which both R$^a$ and R$^b$ have the (S)-configuration).

Preferred chiral substituents R$^a$ and R$^b$ are (1S)-1-methylbutyl, (1S)-1-methylpentyl, (1S)-1-methylhexyl, (1S)-1-methylheptyl, (1S)-1-methyloctyl, (1S)-1-ethylpropyl, (1S)-1-ethylbutyl, (1S)-1-ethylpentyl, (1S)-1-propylbutyl, (1S)-1-propylpentyl, (1S)-1-propylhexyl, (1R)-1-methylbutyl, (1R)-1-methylpentyl, (1R)-1-methylhexyl, (1R)-1-methylheptyl, (1R)-1-methyloctyl, (1R)-1-ethylpropyl, (1R)-1-ethylbutyl, (1R)-1-ethylpentyl, (1R)-1-propylbutyl, (1R)-1-propylpentyl, (1R)-1-propylhexyl.

A preferred class of compounds of the formula (I.a) are cyanated or halogenated rylene diimides, more preferably cyanated or halogenated perylene diimides, in particular N,N'-bis-substituted-(1,7 & 1,6)-di-cyano-perylene-3,4:9,10-bis(dicarboximide)s, N,N'-bis-substituted-(1,7 & 1,6)-di-fluoro-perylene-3,4:9,10-bis(dicarboximide)s, N,N'-bis-substituted-(1,7 & 1,6)-di-chloro-perylene-3,4:9,10-bis(dicarboximide)s and N,N'-bis-substituted-(1,7 & 1,6)-di-bromo-perylene-3,4:9,10-bis(dicarboximide)s. Suitable cyanated or halogenated rylene diimides are described e.g. in U.S. Pat. Nos. 7,671,202, 7,902,363, and 7,569,693, and U.S. Patent Application Publication No. 2010/0319778.

In a further preferred embodiment the compounds of the formula (I.a) are selected from halogenated perylene bisimide derivatives described by R. Schmidt, J. H. Oh, Y.-S. Sun, M. Deppisch, A.-M. Krause, K. Radacki, H. Braunschweig, M. Könemann, P. Erk, Z. Bao and F. Würthner in *J. Am. Chem. Soc.* 2009, 131, 6215-6228.

In a further preferred embodiment the compounds of the formula (I.a) are selected from perylenediimides as described in WO 2007/093643 and WO 2007/116001.

In one special embodiment, component A) is selected from compounds of the general formula (I.a1)

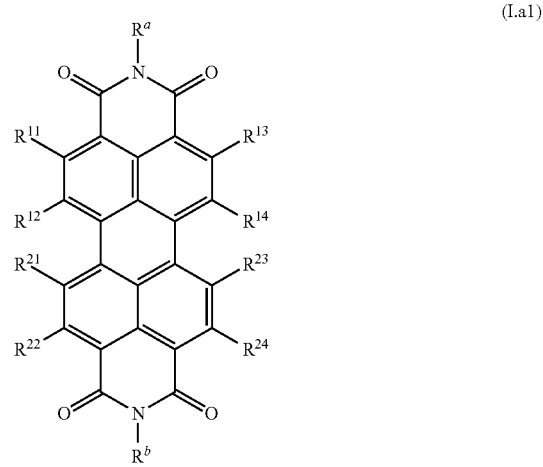

(I.a1)

wherein
R$^a$ and R$^b$ are defined as above,
R$^{12}$ and R$^{23}$ are independently selected from F, Cl, Br, CN, and
R$^{11}$, R$^{13}$, R$^{14}$, R$^{21}$, R$^{22}$ and R$^{24}$ are hydrogen.

Specific examples of compounds of the formula (I.a) include:
N,N'-bis(cyclohexyl)-1,6-dicyano-perylene-3,4:9,10-bis(dicarboximide),
N,N'-bis(cyclohexyl)-1,7-dicyano-perylene-3,4:9,10-bis(dicarboximide),
N,N'-bis(1H,1H-perfluorobutyl)-1,6-dicyano-perylene-3,4:9,10-bis(dicarboximide),
N,N'-bis(1H,1H-perfluorobutyl)-1,7-dicyano-perylene-3,4:9,10-bis(dicarboximide),
N,N'-bis(n-octyl)-1,6-dicyano-perylene-3,4:9,10-bis(dicarboximide),
N,N'-bis(n-octyl)-1,7-dicyano-perylene-3,4:9,10-bis(dicarboximide),
N,N'-bis(2-methylhexyl)-1,6-dicyano-perylene-3,4:9,10-bis(dicarboximide),
N,N'-bis(2-methylhexyl)-1,7-dicyano-perylene-3,4:9,10-bis(dicarboximide),
N,N'-bis(2-ethylhexyl)-1,6-dicyano-perylene-3,4:9,10-bis(dicarboximide),
N,N'-bis(2-ethylhexyl)-1,7-dicyano-perylene-3,4:9,10-bis(dicarboximide),
N,N'-bis[(3S)-3,7-dimethyl-6-octenyl]-1,6-dicyano-perylene-3,4:9,10-bis(dicarboximide),
N,N'-bis[(3S)-3,7-dimethyl-6-octenyl]-1,7-dicyano-perylene-3,4:9,10-bis(dicarboximide),
N,N'-bis(4-n-hexylphenyl)-1,6-dicyano-perylene-3,4:9,10-bis(dicarboximide),
N,N'-bis(4-n-hexylphenyl)-1,7-dicyano-perylene-3,4:9,10-bis(dicarboximide),
N,N'-bis(4-n-dodecylphenyl)-1,6-dicyano-perylene-3,4:9,10-bis(dicarboximide), N,N'-bis(4-n-dodecylphenyl)-1,7-dicyano-perylene-3,4:9,
10-bis(dicarboximide),
N,N'-bis(4-[(3S)-3,7-dimethyl-6-octenyl]phenyl)-1,6-dicyano-perylene-3,4:9,10-bis(dicarboximide),
N,N'-bis(4-[(3S)-3,7-dimethyl-6-octenyl]phenyl)-1,7-dicyano-perylene-3,4:9,10-bis(dicarboximide),
N,N'-bis(4-heptyloxyphenyl)-1,6-dicyano-perylene-3,4:9,
10-bis(dicarboximide),
N,N'-bis(4-heptyloxyphenyl)-1,7-dicyano-perylene-3,4:9,
10-bis(dicarboximide),
N,N'-bis(4-biphenylyl)-1,6-dicyano-perylene-3,4:9,10-bis(dicarboximide),
N,N'-bis(4-biphenylyl)-1,7-dicyano-perylene-3,4:9,10-bis(dicarboximide),
N,N'-bis[4-(4'-n-octylbiphenylyl)]-1,6-dicyano-perylene-3,4:9,10-bis(dicarboximide),
N,N'-bis[4-(4'-n-octylbiphenylyl)]-1,7-dicyano-perylene-3,4:9,10-bis(dicarboximide),
N,N'-bis(4-[4'-((3S)-3,7-dimethyl-6-octenyl]biphenylyl)-1,6-dicyano-perylene-3,4:9,10-bis(dicarboximide),
N,N'-bis(4-[4'-((3S)-3,7-dimethyl-6-octenyl]biphenylyl)-1,7-dicyano-perylene-3,4:9,10-bis(dicarboximide),
N,N'-bis[4-(2',3',4',5',6'-pentafluorobiphenyl)]-1,6-dicyano-perylene-3,4:9,10-bis(dicarboximide),
N,N'-bis[4-(2',3',4',5',6'-pentafluorobiphenyl)]-1,7-dicyano-perylene-3,4:9,10-bis(dicarboximide),
N,N'-bis[4-(4'-n-octyl-2',3',5',6'-tetrafluorobiphenyl)]-1,6-dicyano-perylene-3,4:9,10-bis(dicarboximide),
N,N'-bis[4-(4'-n-octyl-2',3',5',6'-tetrafluorobiphenyl)]-1,7-dicyano-perylene-3,4:9,10-bis(dicarboximide),
N,N'-bis[4-(4'-n-octyl-2,3,5,6-tetrafluorobiphenyl)]-1,6-dicyano-perylene-3,4:9,10-bis(dicarboximide),
N,N'-bis[4-(4'-n-octyl-2,3,5,6-tetrafluorobiphenyl)]-1,7-dicyano-perylene-3,4:9,10-bis(dicarboximide),
N,N'-bis(benzyl)-1,6-dicyano-perylene-3,4:9,10-bis(dicarboximide),
N,N'-bis(benzyl)-1,7-dicyano-perylene-3,4:9,10-bis(dicarboximide),
N,N'-bis(4-n-butylbenzyl)-1,6-dicyano-perylene-3,4:9,10-bis(dicarboximide),
N,N'-bis(4-n-butylbenzyl)-1,7-dicyano-perylene-3,4:9,10-bis(dicarboximide),
N,N'-bis(4-sec-butylphenyl)-1,6-dicyano-perylene-3,4:9,
10-bis(dicarboximide),
N,N'-bis(4-sec-butylphenyl)-1,7-dicyano-perylene-3,4:9,
10-bis(dicarboximide),
N,N'-bis(4-[(3S)-3,7-di methyl-6-octenyloxy]benzyl)-1,6-dicyano-perylene-3,4:9,10-bis(dicarboximide),
N,N'-bis(4-[(3S)-3,7-dimethyl-6-octenyloxy]benzyl)-1,7-dicyano-perylene-3,4:9,10-bis(dicarboximide),
N,N'-bis(4-benzylphenyl)-1,6-dicyano-perylene-3,4:9,10-bis(dicarboximide),
N,N'-bis(4-benzylphenyl)-1,7-dicyano-perylene-3,4:9,10-bis(dicarboximide),
N,N'-bis(4-[1-(2-phenylethyl)]phenyl)-1,6-dicyano-perylene-3,4:9,10-bis(dicarboximide),
N,N'-bis(4-[1-(2-phenylethyl)]phenyl)-1,7-dicyano-perylene-3,4:9,10-bis(dicarboximide),
N,N'-bis(4-n-benzoylphenyl)-1,6-dicyano-perylene-3,4:9,
10-bis(dicarboximide),
N,N'-bis(4-n-benzoylphenyl)-1,7-dicyano-perylene-3,4:9,
10-bis(dicarboximide),
N,N'-bis(1-methylbutyl)-1,6-dicyano-perylene-3,4:9,10-bis(dicarboximide),
N,N'-bis(1-methylbutyl)-1,7-dicyano-perylene-3,4:9,10-bis(dicarboximide),
N,N'-bis(1-methylpentyl)-1,6-dicyano-perylene-3,4:9,10-bis(dicarboximide),
N,N'-bis(1-methylpentyl)-1,7-dicyano-perylene-3,4:9,10-bis(dicarboximide),
N,N'-bis[(1S)-1-methylpentyl]-1,6-dicyano-perylene-3,4:9,
10-bis(dicarboximide)
N,N'-bis[(1S)-1-methylpentyl]-1,7-dicyano-perylene-3,4:9,
10-bis(dicarboximide)
N,N'-bis[(1R)-1-methylpentyl]-1,6-dicyano-perylene-3,4:9,
10-bis(dicarboximide)
N,N'-bis[(1R)-1-methylpentyl]-1,7-dicyano-perylene-3,4:9,
10-bis(dicarboximide)
N,N'-bis(1-methylhexyl)-1,6-dicyano-perylene-3,4:9,10-bis(dicarboximide),
N,N'-bis(1-methylhexyl)-1,7-dicyano-perylene-3,4:9,10-bis(dicarboximide),
N,N'-bis(1-ethylpropyl)-1,6-dicyano-perylene-3,4:9,10-bis(dicarboximide),
N,N'-bis(1-ethylpropyl)-1,7-dicyano-perylene-3,4:9,10-bis(dicarboximide),
N,N'-bis(1-ethylbutyl)-1,6-dicyano-perylene-3,4:9,10-bis(dicarboximide),
N,N'-bis(1-ethylbutyl)-1,7-dicyano-perylene-3,4:9,10-bis(dicarboximide),
N,N'-bis(1-ethylpentyl)-1,6-dicyano-perylene-3,4:9,10-bis(dicarboximide),
N,N'-bis(1-ethylpentyl)-1,7-dicyano-perylene-3,4:9,10-bis(dicarboximide),
N,N'-bis(1-ethylhexyl)-1,6-dicyano-perylene-3,4:9,10-bis(dicarboximide),
N,N'-bis(1-ethylhexyl)-1,7-dicyano-perylene-3,4:9,10-bis(dicarboximide),
N,N'-bis(1,3-dimethylbutyl)-1,6-dicyano-perylene-3,4:9,
10-bis(dicarboximide),
N,N'-bis(1,3-dimethylbutyl)-1,7-dicyano-perylene-3,4:9,
10-bis(dicarboximide),
N,N'-bis(cyclohexyl)-1,6-dichloro-perylene-3,4:9,10-bis(dicarboximide),
N,N'-bis(cyclohexyl)-1,7-dichloro-perylene-3,4:9,10-bis(dicarboximide),
N,N'-bis(1H,1H-perfluorobutyl)-1,6-dichloro-perylene-3,4:
9,10-bis(dicarboximide),
N,N'-bis(1H,1H-perfluorobutyl)-1,7-dichloro-perylene-3,4:
9,10-bis(dicarboximide),
N,N'-bis(n-octyl)-1,6-dichloro-perylene-3,4:9,10-bis(dicarboximide),
N,N'-bis(n-octyl)-1,7-dichloro-perylene-3,4:9,10-bis(dicarboximide),
N,N'-bis(2-methylhexyl)-1,6-dichloro-perylene-3,4:9,10-bis(dicarboximide),
N,N'-bis(2-methylhexyl)-1,7-dichloro-perylene-3,4:9,10-bis(dicarboximide),
N,N'-bis(2-ethylhexyl)-1,6-dichloro-perylene-3,4:9,10-bis(dicarboximide),
N,N'-bis(2-ethylhexyl)-1,7-dichloro-perylene-3,4:9,10-bis(dicarboximide),
N,N'-bis[(3S)-3,7-dimethyl-6-octenyl]-1,6-dichloro-perylene-3,4:9,10-bis(dicarboximide),
N,N'-bis[(3S)-3,7-dimethyl-6-octenyl]-1,7-dichloro-perylene-3,4:9,10-bis(dicarboximide),
N,N'-bis(4-n-hexylphenyl)-1,6-dichloro-perylene-3,4:9,10-bis(dicarboximide),
N,N'-bis(4-n-hexylphenyl)-1,7-dichloro-perylene-3,4:9,10-bis(dicarboximide),
N,N'-bis(4-n-dodecylphenyl)-1,6-dichloro-perylene-3,4:9,
10-bis(dicarboximide), N,N'-bis(4-n-dodecylphenyl)-1,7-dichloro-perylene-3,4:9,10-bis(dicarboximide),
N,N'-bis(4-[(3S)-3,7-dimethyl-6-octenyl]phenyl)-1,6-dichloro-perylene-3,4:9,10-bis(dicarboximide),
N,N'-bis(4-[(3S)-3,7-dimethyl-6-octenyl]phenyl)-1,7-dichloro-perylene-3,4:9,10-bis(dicarboximide),
N,N'-bis(4-heptyloxyphenyl)-1,6-dichloro-perylene-3,4:9,10-bis(dicarboximide),
N,N'-bis(4-heptyloxyphenyl)-1,7-dichloro-perylene-3,4:9,10-bis(dicarboximide),
N,N'-bis(4-biphenylyl)-1,6-dichloro-perylene-3,4:9,10-bis(dicarboximide),
N,N'-bis(4-biphenylyl)-1,7-dichloro-perylene-3,4:9,10-bis(dicarboximide),
N,N'-bis[4-(4'-n-octylbiphenylyl)]-1,6-dichloro-perylene-3,4:9,10-bis(dicarboximide),
N,N'-bis[4-(4'-n-octylbiphenylyl)]-1,7-dichloro-perylene-3,4:9,10-bis(dicarboximide),
N,N'-bis(4-[4'-((3S)-3,7-dimethyl-6-octenyl]biphenylyl)-1,6-dichloro-perylene-3,4:9,10-bis(dicarboximide),
N,N'-bis(4-[4'-((3S)-3,7-dimethyl-6-octenyl]biphenylyl)-1,7-dichloro-perylene-3,4:9,10-bis(dicarboximide),
N,N'-bis[4-(2',3',4',5',6'-pentafluorobiphenyl)]-1,6-dichloro-perylene-3,4:9,10-bis(dicarboximide),
N,N'-bis[4-(2',3',4',5',6'-pentafluorobiphenyl)]-1,7-dichloro-perylene-3,4:9,10-bis(dicarboximide),
N,N'-bis[4-(4'-n-octyl-2',3',5',6'-tetrafluorobiphenyl)]-1,6-dichloro-perylene-3,4:9,10-bis(dicarboximide),
N,N'-bis[4-(4'-n-octyl-2',3',5',6'-tetrafluorobiphenyl)]-1,7-dichloro-perylene-3,4:9,10-bis(dicarboximide),
N,N'-bis[4-(4'-n-octyl-2,3,5,6-tetrafluorobiphenyl)]-1,6-dichloro-perylene-3,4:9,10-bis(dicarboximide),
N,N'-bis[4-(4'-n-octyl-2,3,5,6-tetrafluorobiphenyl)]-1,7-dichloro-perylene-3,4:9,10-bis(dicarboximide),
N,N'-bis(benzyl)-1,6-dichloro-perylene-3,4:9,10-bis(dicarboximide),
N,N'-bis(benzyl)-1,7-dichloro-perylene-3,4:9,10-bis(dicarboximide),
N,N'-bis(4-n-butylbenzyl)-1,6-dichloro-perylene-3,4:9,10-bis(dicarboximide),
N,N'-bis(4-n-butylbenzyl)-1,7-dichloro-perylene-3,4:9,10-bis(dicarboximide),
N,N'-bis(4-sec-butylphenyl)-1,6-dichloro-perylene-3,4:9,10-bis(dicarboximide),
N,N'-bis(4-sec-butylphenyl)-1,7-dichloro-perylene-3,4:9,10-bis(dicarboximide),
N,N'-bis(4-[(3S)-3,7-dimethyl-6-octenyloxy]benzyl)-1,6-dichloro-perylene-3,4:9,10-bis(dicarboximide),
N,N'-bis(4-[(3S)-3,7-dimethyl-6-octenyloxy]benzyl)-1,7-dichloro-perylene-3,4:9,10-bis(dicarboximide),
N,N'-bis(4-benzylphenyl)-1,6-dichloro-perylene-3,4:9,10-bis(dicarboximide),
N,N'-bis(4-benzylphenyl)-1,7-dichloro-perylene-3,4:9,10-bis(dicarboximide),
N,N'-bis(4-[1-(2-phenylethyl)]phenyl)-1,6-dichloro-perylene-3,4:9,10-bis(dicarboximide),
N,N'-bis(4-[1-(2-phenylethyl)]phenyl)-1,7-dichloro-perylene-3,4:9,10-bis(dicarboximide),
N,N'-bis(4-n-benzoylphenyl)-1,6-dichloro-perylene-3,4:9,10-bis(dicarboximide),
N,N'-bis(4-n-benzoylphenyl)-1,7-dichloro-perylene-3,4:9,10-bis(dicarboximide),
N,N'-bis(1-methylbutyl)-1,6-dichloro-perylene-3,4:9,10-bis(dicarboximide),
N,N'-bis(1-methylbutyl)-1,7-dichloro-perylene-3,4:9,10-bis(dicarboximide),
N,N'-bis(1-methylpentyl)-1,6-dichloro-perylene-3,4:9,10-bis(dicarboximide),
N,N'-bis(1-methylpentyl)-1,7-dichloro-perylene-3,4:9,10-bis(dicarboximide),
N,N'-bis(1-methylhexyl)-1,6-dichloro-perylene-3,4:9,10-bis(dicarboximide),
N,N'-bis(1-methylhexyl)-1,7-dichloro-perylene-3,4:9,10-bis(dicarboximide),
N,N'-bis(1-ethylpropyl)-1,6-dichloro-perylene-3,4:9,10-bis(dicarboximide),
N,N'-bis(1-ethylpropyl)-1,7-dichloro-perylene-3,4:9,10-bis(dicarboximide),
N,N'-bis(1-ethylbutyl)-1,6-dichloro-perylene-3,4:9,10-bis(dicarboximide),
N,N'-bis(1-ethylbutyl)-1,7-dichloro-perylene-3,4:9,10-bis(dicarboximide),
N,N'-bis(1-ethylpentyl)-1,6-dichloro-perylene-3,4:9,10-bis(dicarboximide),
N,N'-bis(1-ethylpentyl)-1,7-dichloro-perylene-3,4:9,10-bis(dicarboximide),
N,N'-bis(1-ethylhexyl)-1,6-dichloro-perylene-3,4:9,10-bis(dicarboximide),
N,N'-bis(1-ethylhexyl)-1,7-dichloro-perylene-3,4:9,10-bis(dicarboximide),
N,N'-bis(1,3-dimethylbutyl)-1,6-dichloro-perylene-3,4:9,10-bis(dicarboximide),
N,N'-bis(1,3-dimethylbutyl)-1,7-dichloro-perylene-3,4:9,10-bis(dicarboximide),
N,N'-bis(cyclohexyl)-1,6-dibromo-perylene-3,4:9,10-bis(dicarboximide),
N,N'-bis(cyclohexyl)-1,7-dibromo-perylene-3,4:9,10-bis(dicarboximide),
N,N'-bis(1H,1H-perfluorobutyl)-1,6-dibromo-perylene-3,4:9,10-bis(dicarboximide),
N,N'-bis(1H,1H-perfluorobutyl)-1,7-dibromo-perylene-3,4:9,10-bis(dicarboximide),
N,N'-bis(n-octyl)-1,6-dibromo-perylene-3,4:9,10-bis(dicarboximide),
N,N'-bis(n-octyl)-1,7-dibromo-perylene-3,4:9,10-bis(dicarboximide),
N,N'-bis(2-methylhexyl)-1,6-dibromo-perylene-3,4:9,10-bis(dicarboximide),
N,N'-bis(2-methylhexyl)-1,7-dibromo-perylene-3,4:9,10-bis(dicarboximide),
N,N'-bis(2-ethylhexyl)-1,6-dibromo-perylene-3,4:9,10-bis(dicarboximide),
N,N'-bis(2-ethylhexyl)-1,7-dibromo-perylene-3,4:9,10-bis(dicarboximide),
N,N'-bis[(3S)-3,7-dimethyl-6-octenyl]-1,6-dibromo-perylene-3,4:9,10-bis(dicarboximide),
N,N'-bis[(3S)-3,7-dimethyl-6-octenyl]-1,7-dibromo-perylene-3,4:9,10-bis(dicarboximide),
N,N'-bis(4-n-hexyl phenyl)-1,6-dibromo-perylene-3,4:9,10-bis(dicarboximide),
N,N'-bis(4-n-hexyl phenyl)-1,7-dibromo-perylene-3,4:9,10-bis(dicarboximide),
N,N'-bis(4-n-dodecyl phenyl)-1,6-dibromo-perylene-3,4:9,10-bis(dicarboximide),
N,N'-bis(4-n-dodecyl phenyl)-1,7-dibromo-perylene-3,4:9,10-bis(dicarboximide),
N,N'-bis(4-[(3S)-3,7-dimethyl-6-octenyl]phenyl)-1,6-dibromo-perylene-3,4:9,10-bis(dicarboximide),
N,N'-bis(4-[(3S)-3,7-dimethyl-6-octenyl]phenyl)-1,7-dibromo-perylene-3,4:9,10-bis(dicarboximide),
N,N'-bis(4-heptyloxyphenyl)-1,6-dibromo-perylene-3,4:9,10-bis(dicarboximide), N,N'-bis(4-heptyloxyphenyl)-1,7-dibromo-perylene-3,4:9,10-bis(dicarboximide), N,N'-bis(4-biphenylyl)-1,6-dibromo-perylene-3,4:9,10-bis(dicarboximide), N,N'-bis(4-biphenylyl)-1,7-dibromo-perylene-3,4:9,10-bis(dicarboximide), N,N'-bis[4-(4'-n-octylbiphenylyl)]-1,6-dibromo-perylene-3,4:9,10-bis(dicarboximide), N,N'-bis[4-(4'-n-octylbiphenylyl)]-1,7-dibromo-perylene-3,4:9,10-bis(dicarboximide), N,N'-bis(4-[4'-((3S)-3,7-dimethyl-6-octenyl]biphenylyl)-1,6-dibromo-perylene-3,4:9,10-bis(dicarboximide), N,N'-bis(4-[4'-((3S)-3,7-dimethyl-6-octenyl]biphenylyl)-1,7-dibromo-perylene-3,4:9,10-bis(dicarboximide), N,N'-bis[4-(2',3',4',5',6'-pentafluorobiphenyl)]-1,6-dibromo-perylene-3,4:9,10-bis(dicarboximide), N,N'-bis[4-(2',3',4',5',6'-pentafluorobiphenyl)]-1,7-dibromo-perylene-3,4:9,10-bis(dicarboximide), N,N'-bis[4-(4'-n-octyl-2',3',5',6'-tetrafluorobiphenyl)]-1,6-dibromo-perylene-3,4:9,10-bis(dicarboximide), N,N'-bis[4-(4'-n-octyl-2',3',5',6'-tetrafluorobiphenyl)]-1,7-dibromo-perylene-3,4:9,10-bis(dicarboximide), N,N'-bis[4-(4'-n-octyl-2,3,5,6-tetrafluorobiphenyl)]-1,6-dibromo-perylene-3,4:9,10-bis(dicarboximide), N,N'-bis[4-(4'-n-octyl-2,3,5,6-tetrafluorobiphenyl)]-1,7-dibromo-perylene-3,4:9,10-bis(dicarboximide), N,N'-bis(benzyl)-1,6-dibromo-perylene-3,4:9,10-bis(dicarboximide), N,N'-bis(benzyl)-1,7-dibromo-perylene-3,4:9,10-bis(dicarboximide), N,N'-bis(4-n-butylbenzyl)-1,6-dibromo-perylene-3,4:9,10-bis(dicarboximide), N,N'-bis(4-n-butylbenzyl)-1,7-dibromo-perylene-3,4:9,10-bis(dicarboximide), N,N'-bis(4-sec-butylphenyl)-1,6-dibromo-perylene-3,4:9,10-bis(dicarboximide), N,N'-bis(4-sec-butylphenyl)-1,7-dibromo-perylene-3,4:9,10-bis(dicarboximide), N,N'-bis(4-[(3S)-3,7-dimethyl-6-octenyloxy]benzyl)-1,6-dibromo-perylene-3,4:9,10-bis(dicarboximide), N,N'-bis(4-[(3S)-3,7-dimethyl-6-octenyloxy]benzyl)-1,7-dibromo-perylene-3,4:9,10-bis(dicarboximide), N,N'-bis(4-benzylphenyl)-1,6-dibromo-perylene-3,4:9,10-bis(dicarboximide), N,N'-bis(4-benzylphenyl)-1,7-dibromo-perylene-3,4:9,10-bis(dicarboximide), N,N'-bis(4-[1-(2-phenylethyl)]phenyl)-1,6-dibromo-perylene-3,4:9,10-bis(dicarboximide), N,N'-bis(4-[1-(2-phenylethyl)]phenyl)-1,7-dibromo-perylene-3,4:9,10-bis(dicarboximide), N,N'-bis(4-n-benzoylphenyl)-1,6-dibromo-perylene-3,4:9,10-bis(dicarboximide), N,N'-bis(4-n-benzoylphenyl)-1,7-dibromo-perylene-3,4:9,10-bis(dicarboximide), N,N'-bis(1-methylbutyl)-1,6-dibromo-perylene-3,4:9,10-bis(dicarboximide), N,N'-bis(1-methylbutyl)-1,7-dibromo-perylene-3,4:9,10-bis(dicarboximide), N,N'-bis(1-methylpentyl)-1,6-dibromo-perylene-3,4:9,10-bis(dicarboximide), N,N'-bis(1-methylpentyl)-1,7-dibromo-perylene-3,4:9,10-bis(dicarboximide), N,N'-bis(1-methylhexyl)-1,6-dibromo-perylene-3,4:9,10-bis(dicarboximide), N,N'-bis(1-methylhexyl)-1,7-dibromo-perylene-3,4:9,10-bis(dicarboximide), N,N'-bis(1-ethylpropyl)-1,6-dibromo-perylene-3,4:9,10-bis(dicarboximide), N,N'-bis(1-ethylpropyl)-1,7-dibromo-perylene-3,4:9,10-bis(dicarboximide), N,N'-bis(1-ethylbutyl)-1,6-dibromo-perylene-3,4:9,10-bis(dicarboximide), N,N'-bis(1-ethylbutyl)-1,7-dibromo-perylene-3,4:9,10-bis(dicarboximide), N,N'-bis(1-ethylpentyl)-1,6-dibromo-perylene-3,4:9,10-bis(dicarboximide), N,N'-bis(1-ethylpentyl)-1,7-dibromo-perylene-3,4:9,10-bis(dicarboximide), N,N'-bis(1-ethylhexyl)-1,6-dibromo-perylene-3,4:9,10-bis(dicarboximide), N,N'-bis(1-ethylhexyl)-1,7-dibromo-perylene-3,4:9,10-bis(dicarboximide), N,N'-bis(1,3-dimethylbutyl)-1,6-dibromo-perylene-3,4:9,10-bis(dicarboximide) and N,N'-bis(1,3-dimethylbutyl)-1,7-dibromo-perylene-3,4:9,10-bis(dicarboximide).

Some particularly preferred compounds (I.a) are specified below:

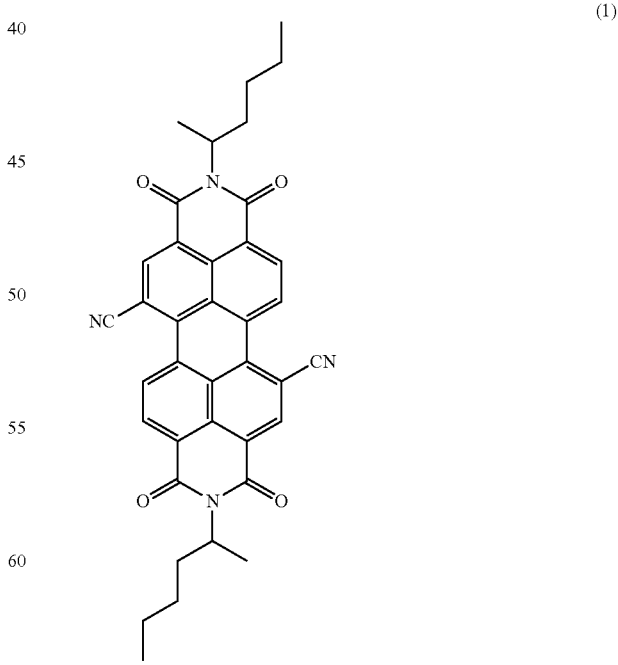

(1)

(2)
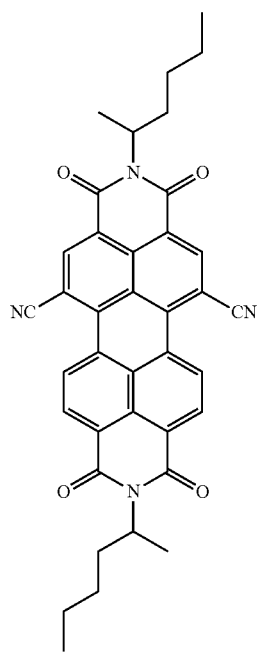
(3)
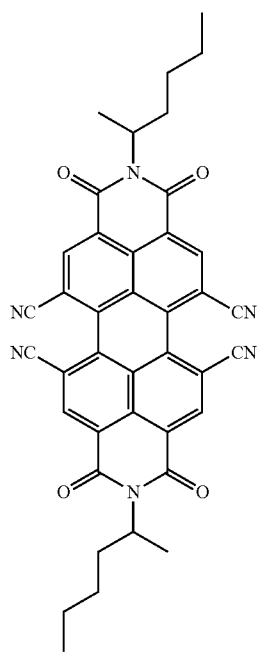
(4)
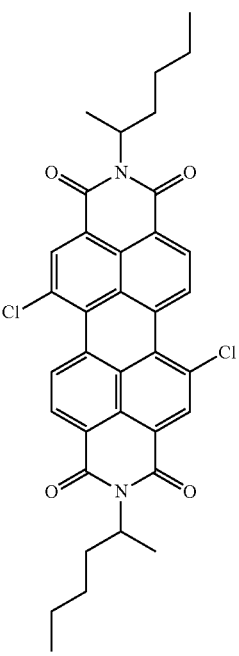
(5)
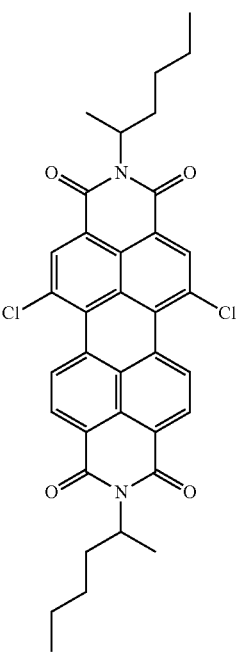

(6)
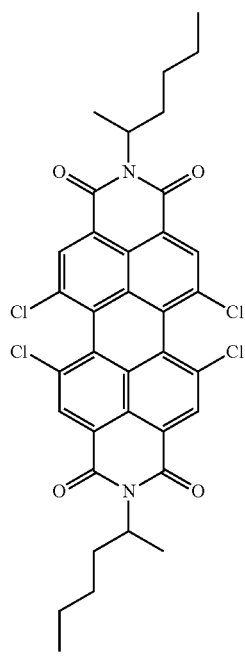
(8)
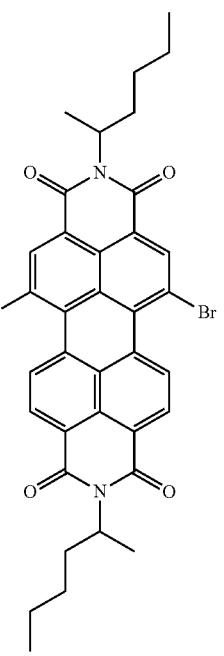
(7)
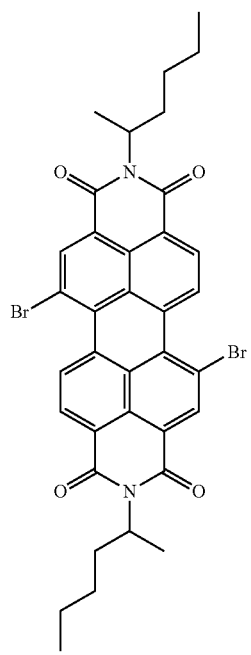
(9)
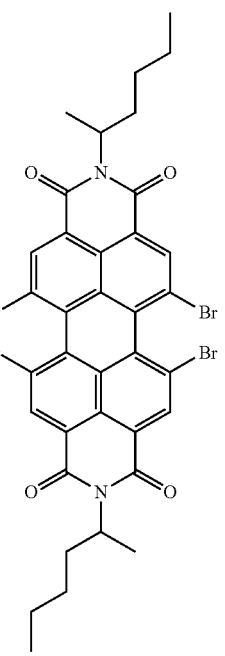

(10)
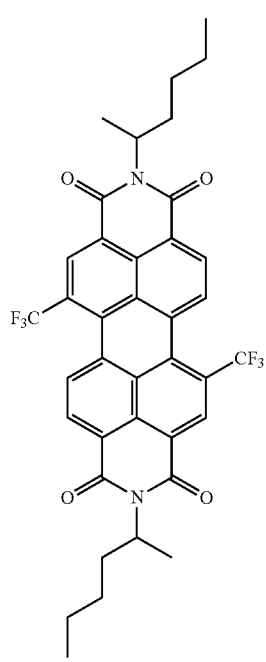
(11)
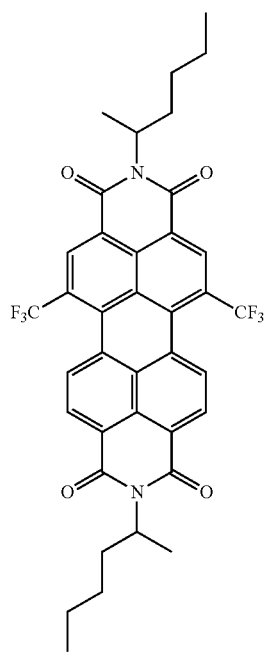
(12)
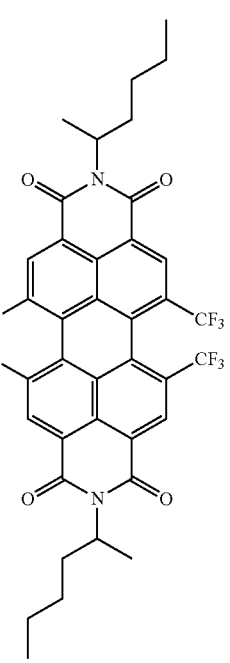
(13)
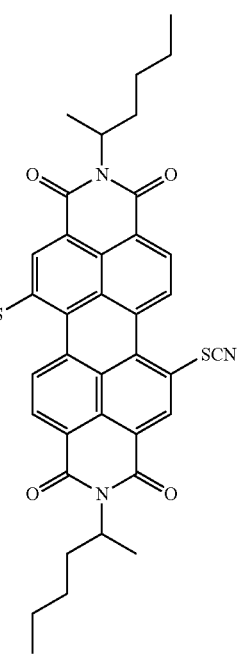

(14)
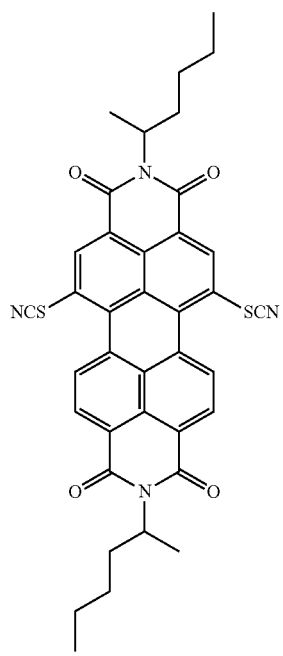
(15)
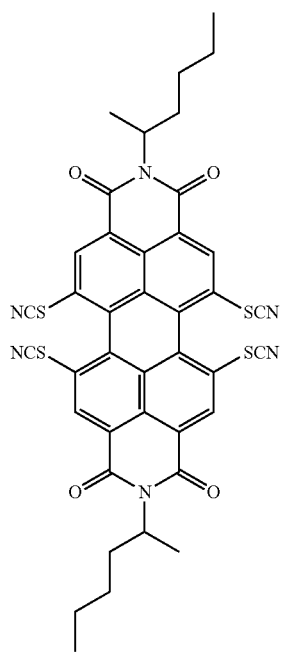
(16)
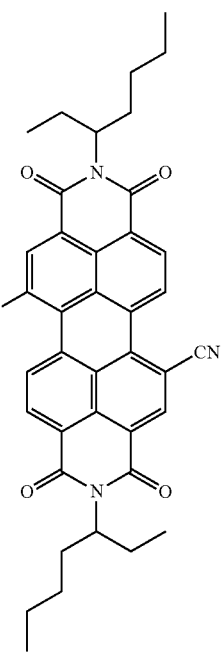
(17)
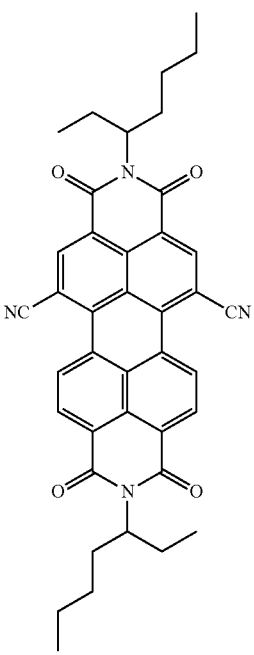

(18)
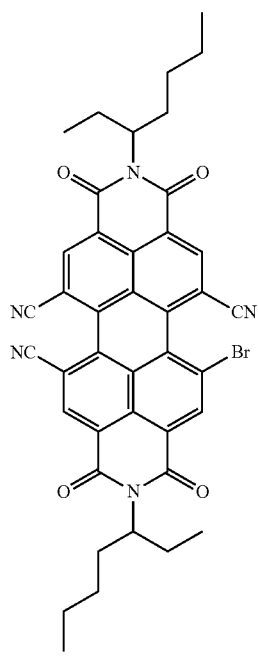
(20)
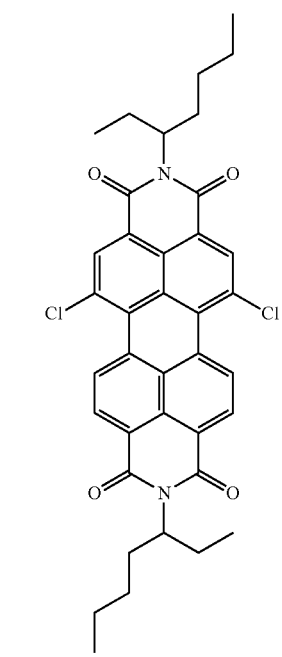
(19)
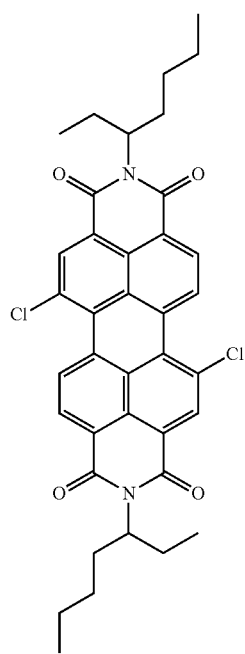
(21)
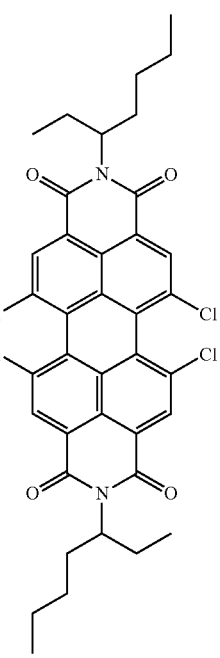

(22)
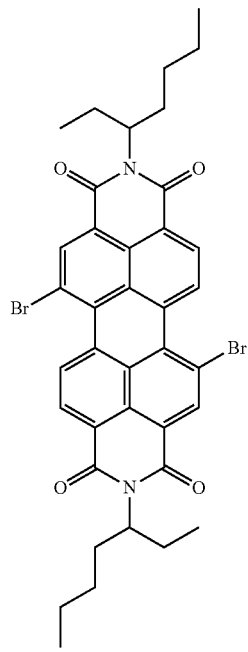
(23)
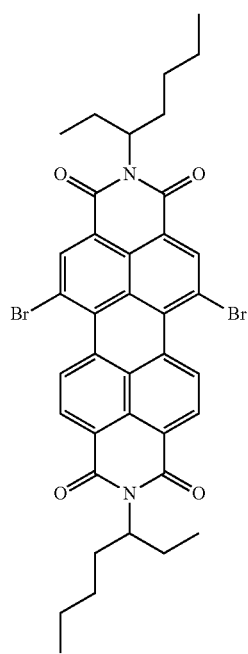
(24)
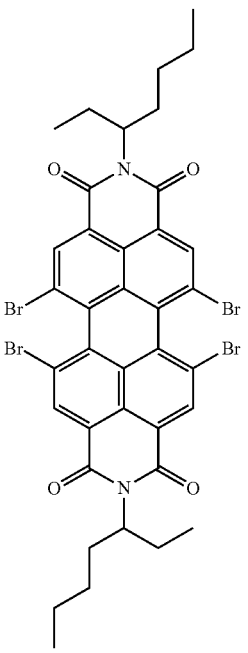
(25)
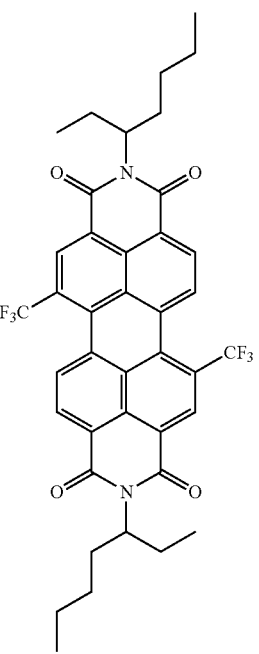

(26)
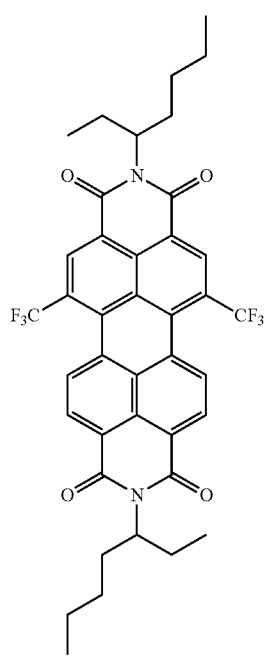
(28)
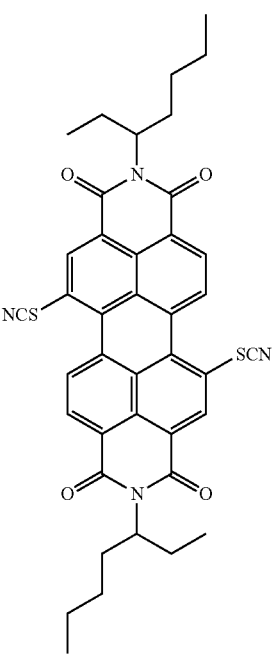
(27)
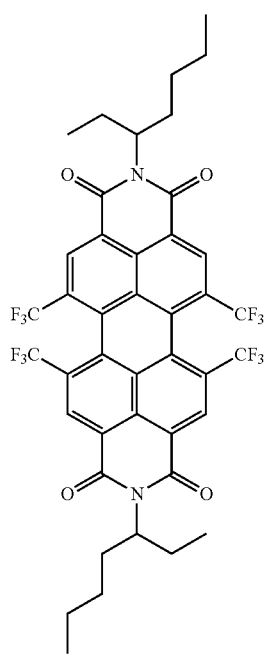
(29)
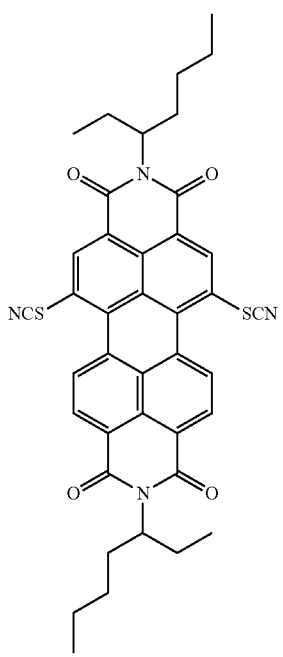

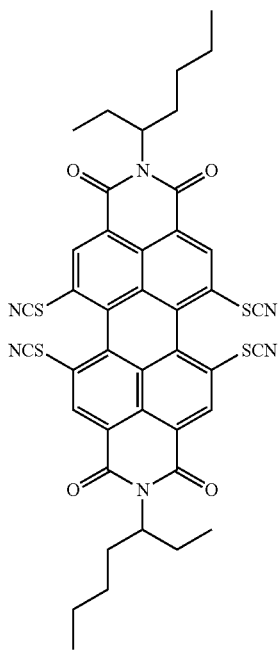
(30)
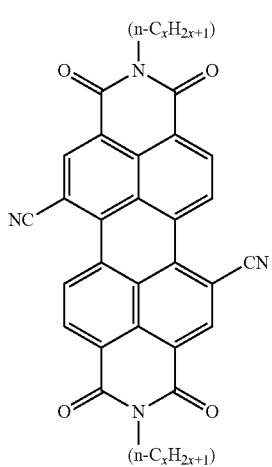
(31)
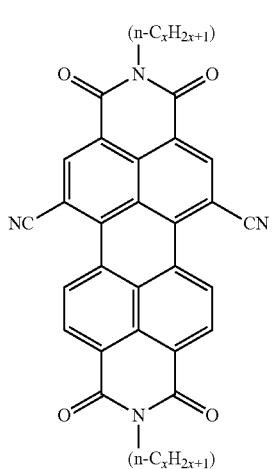
(32)
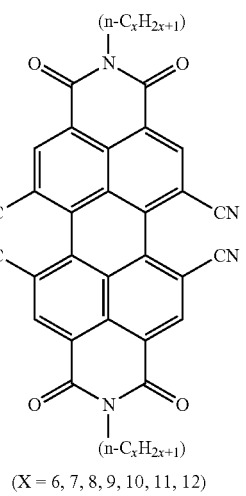
(33)
(X = 6, 7, 8, 9, 10, 11, 12)
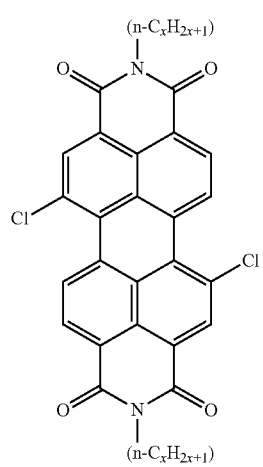
(34)
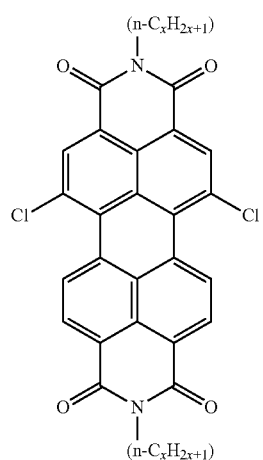
(35)

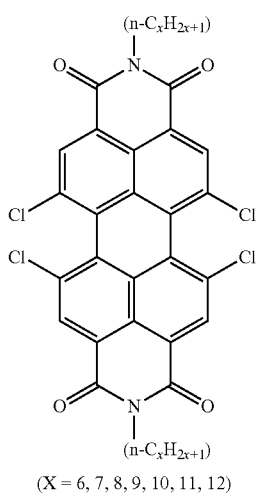
(36)
(X = 6, 7, 8, 9, 10, 11, 12)
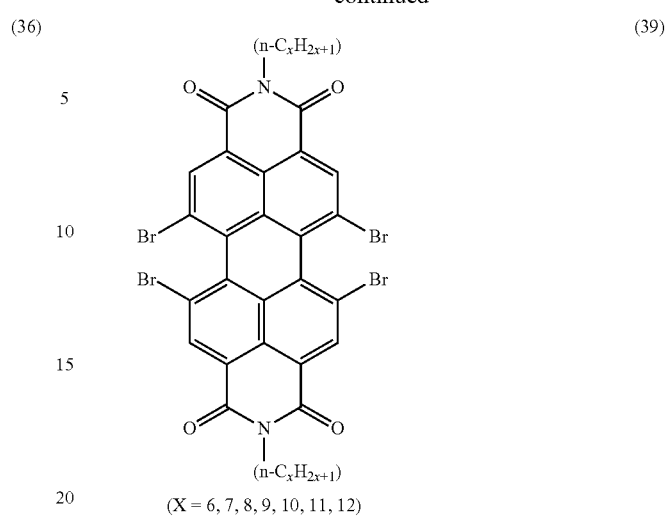
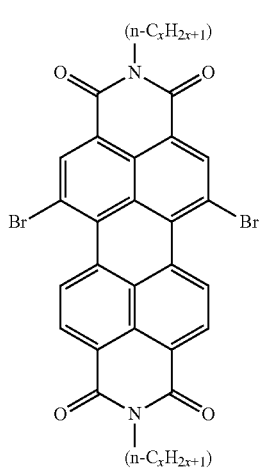
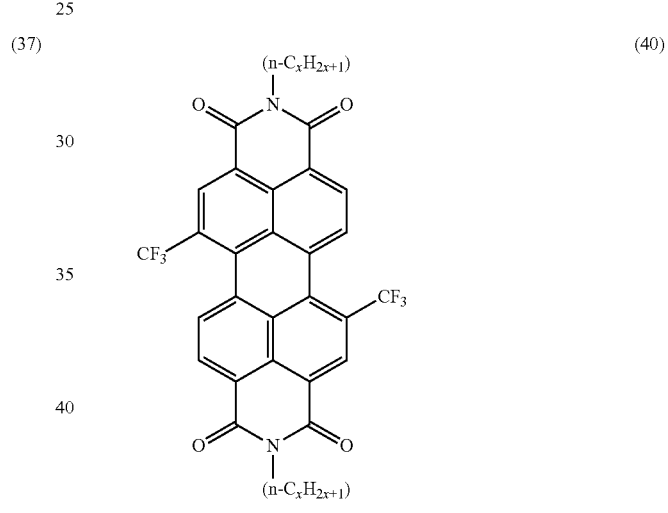
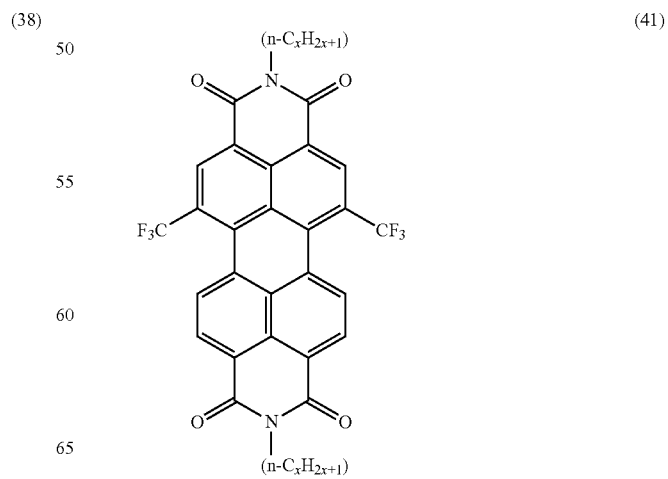

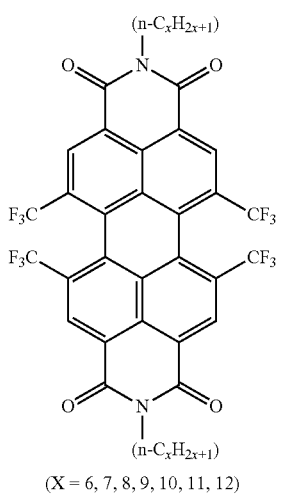
(42)
(X = 6, 7, 8, 9, 10, 11, 12)
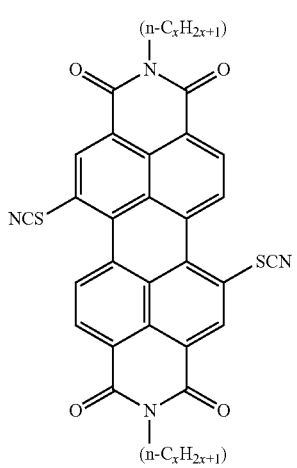
(43)
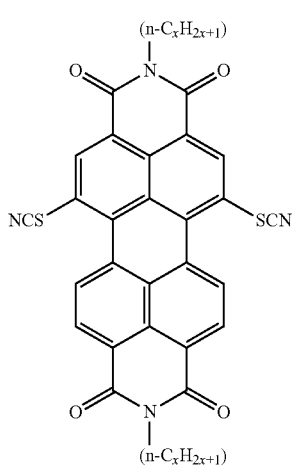
(44)
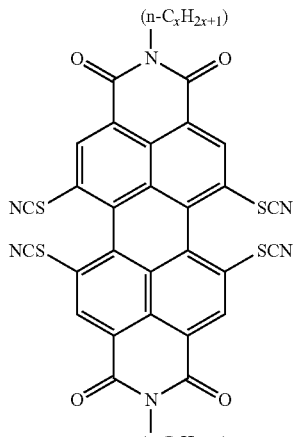
(45)
(X = 6, 7, 8, 9, 10, 11, 12)
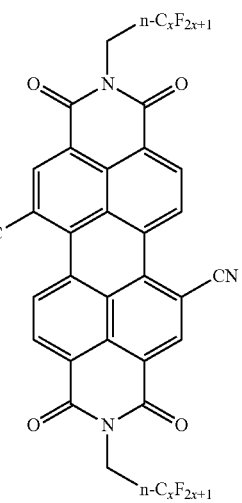
(46)
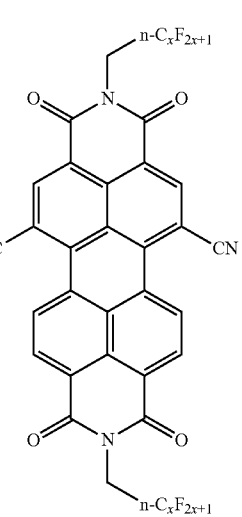
(47)

49
-continued
(48)
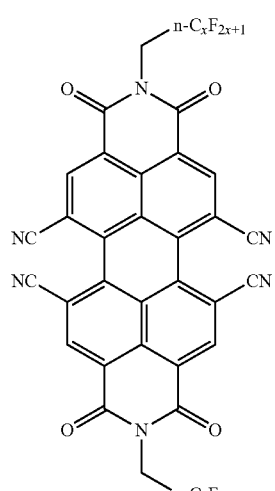
(X = 2, 3, 4)
(49)
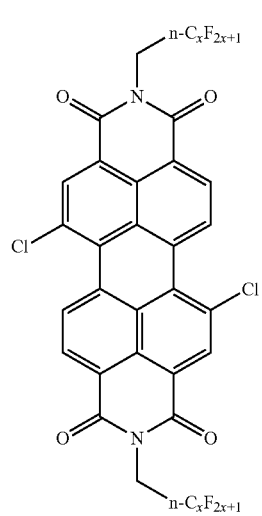
(50)
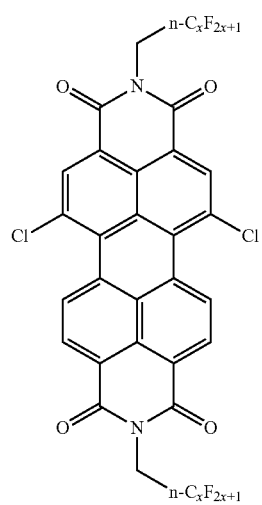
50
-continued
(51)
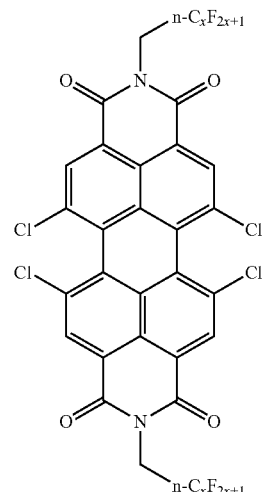
(X = 2, 3, 4)
(52)
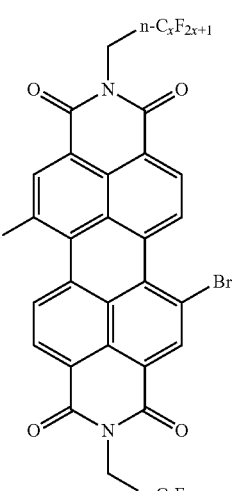
(53)
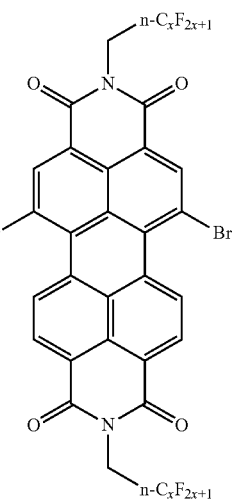

-continued
(54)
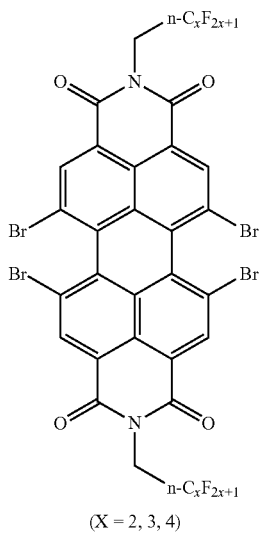
(X = 2, 3, 4)
(55)
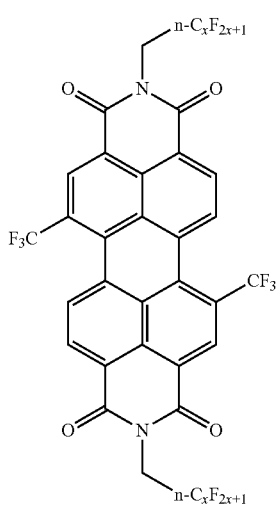
(56)
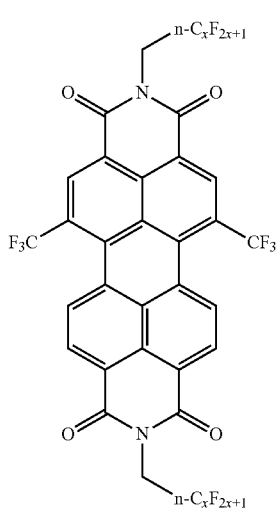
-continued
(57)
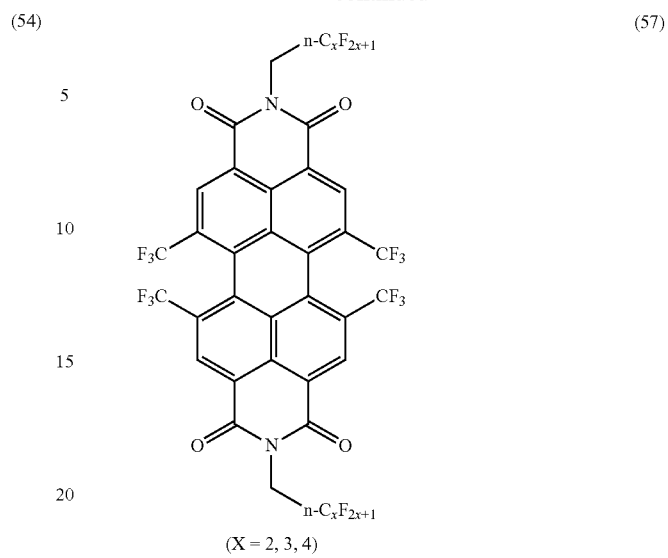
(X = 2, 3, 4)
(58)
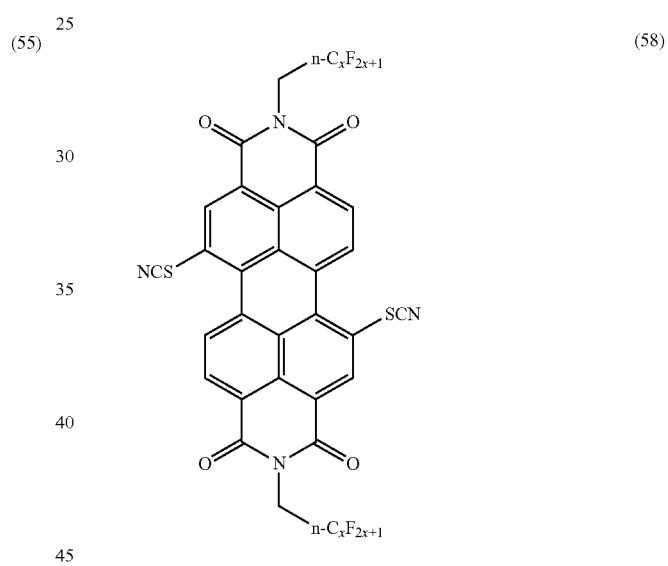
(59)
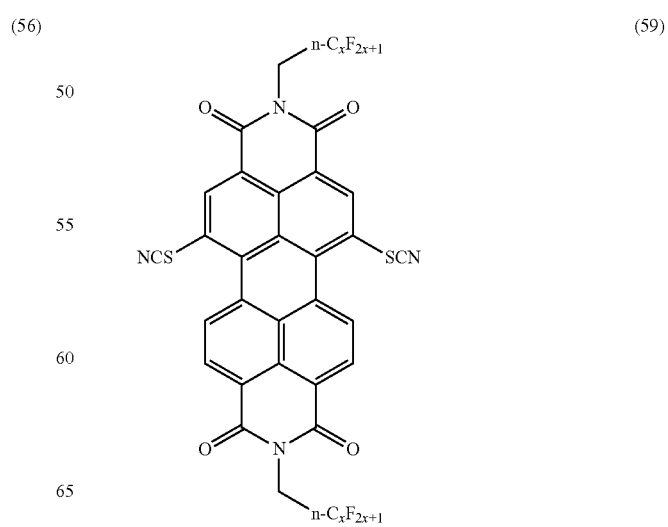

(60)
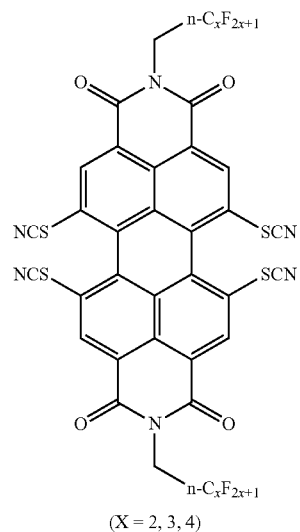
(X = 2, 3, 4)
(61)
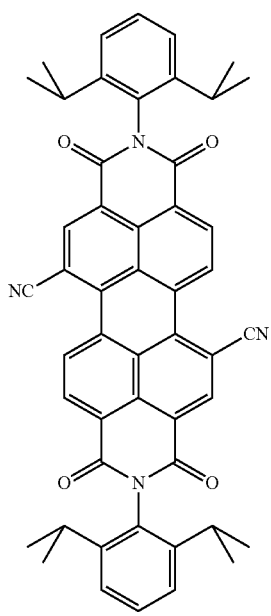
(62)
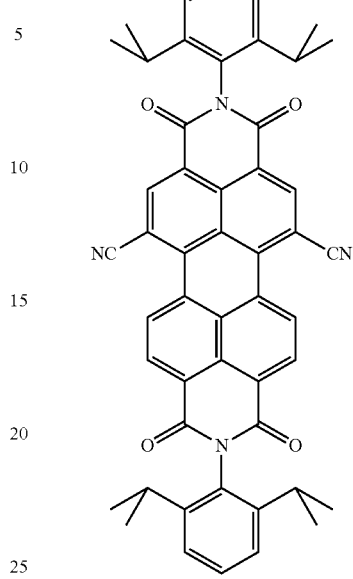
(63)
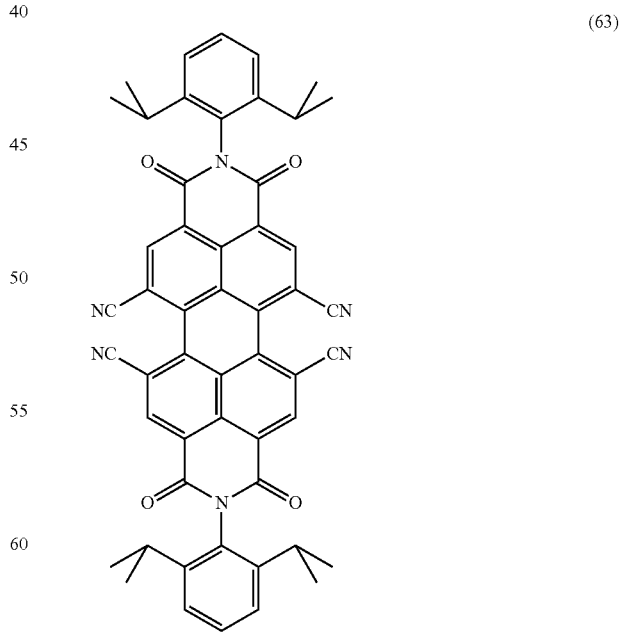

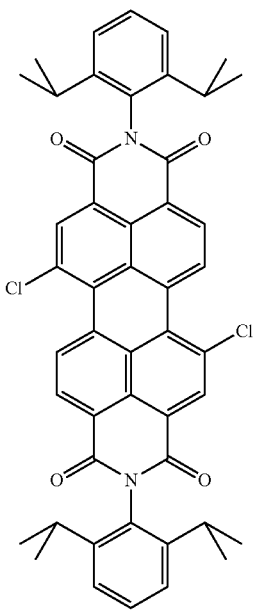
(64)
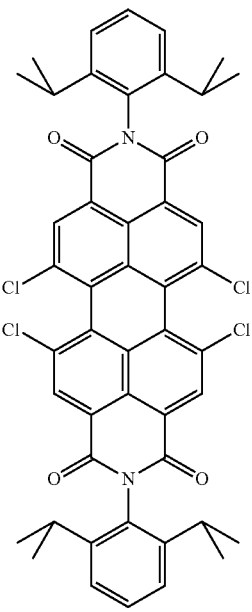
(66)
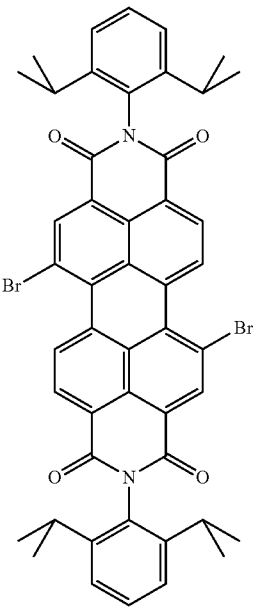
(65)
(67)

(68)
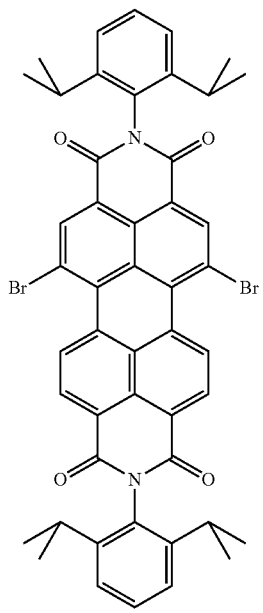
(69)
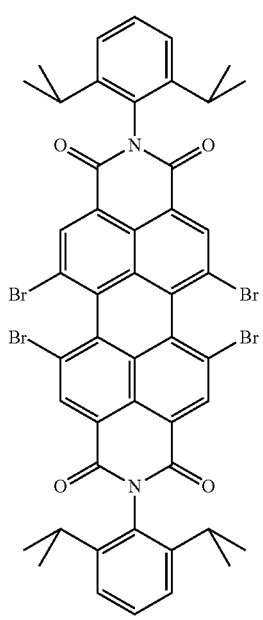
(70)
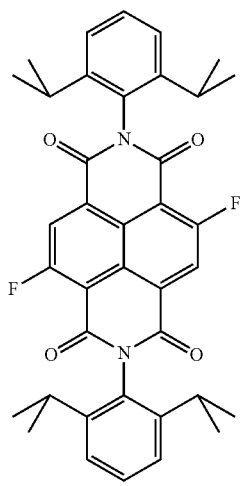
(71)
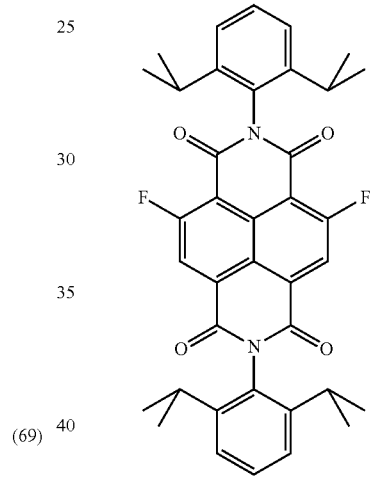
(72)
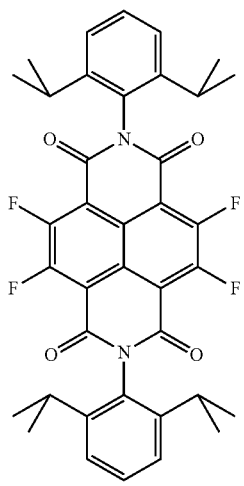

(73)
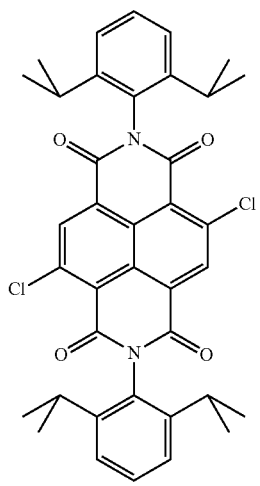
(74)
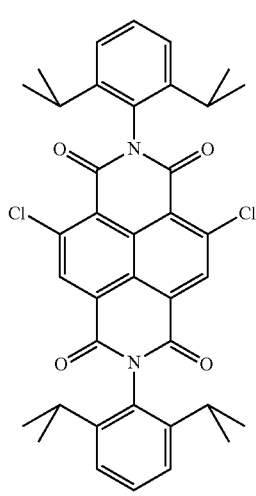
(75)
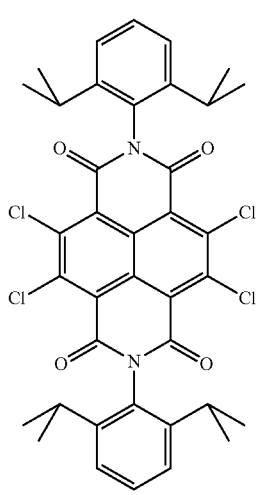
(76)
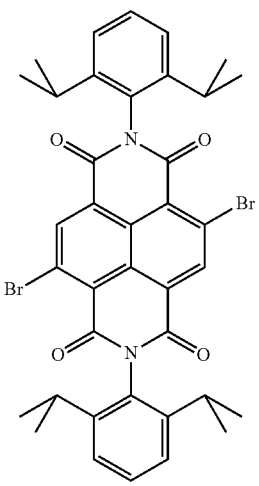
(77)
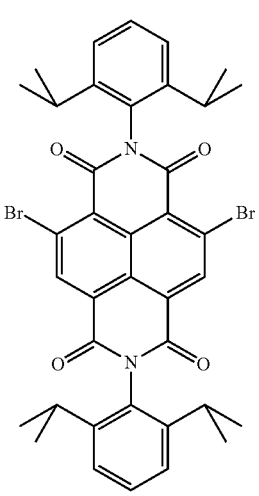
(78)
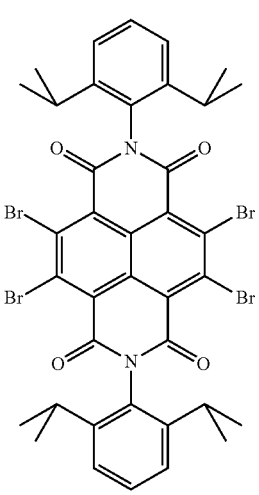

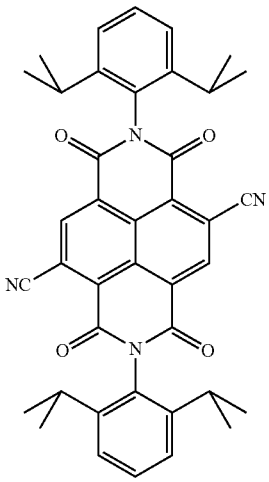
(79)
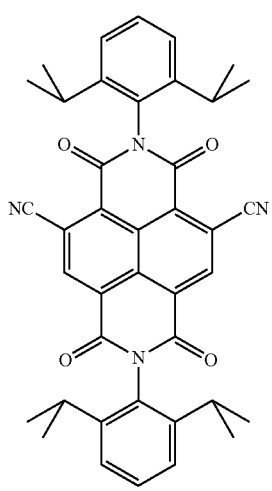
(80)
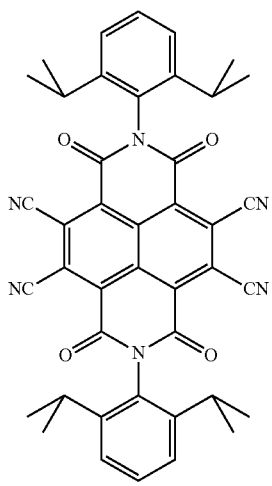
(81)
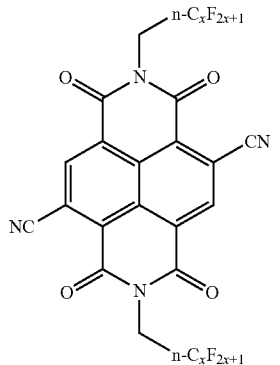
(82)
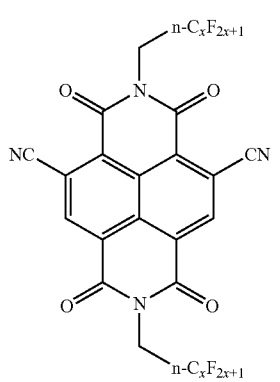
(83)
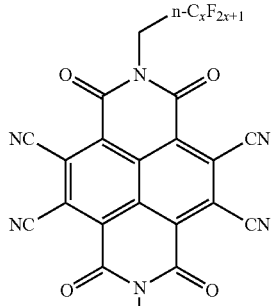
(84)
(x = 2, 3, 4)
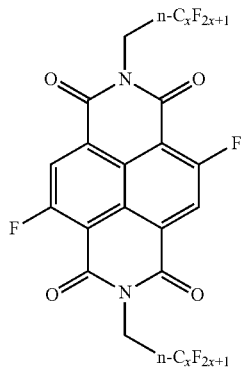
(85)

-continued
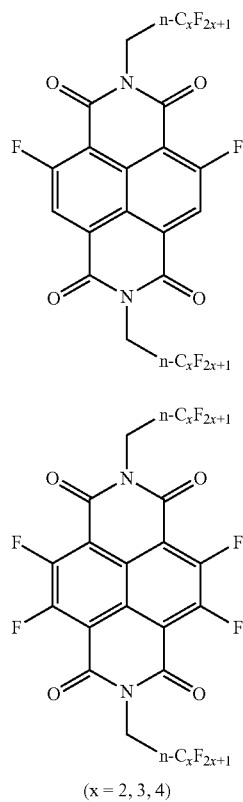
(86)
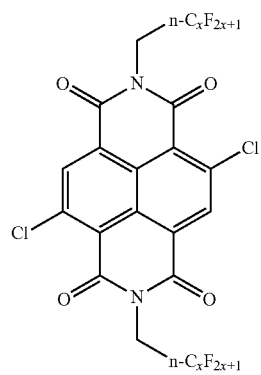
(87)
(x = 2, 3, 4)
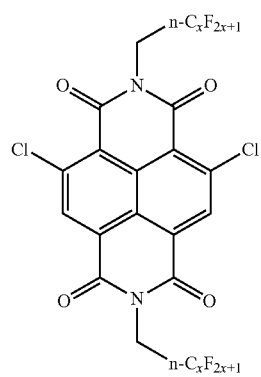
(88)
(89)
-continued
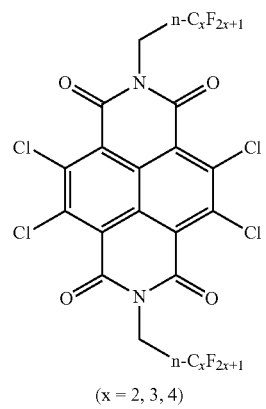
(90)
(x = 2, 3, 4)
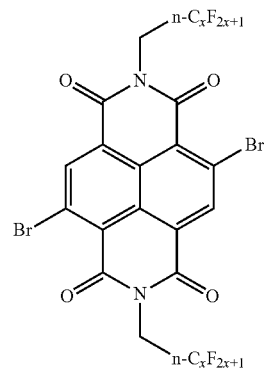
(91)
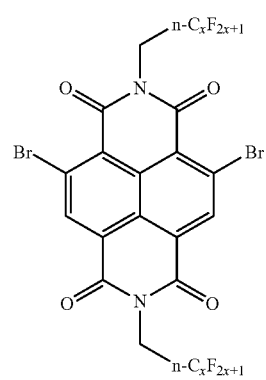
(92)
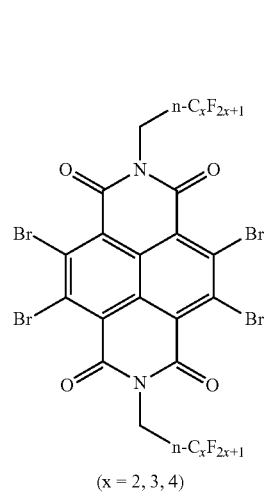
(93)
(x = 2, 3, 4)

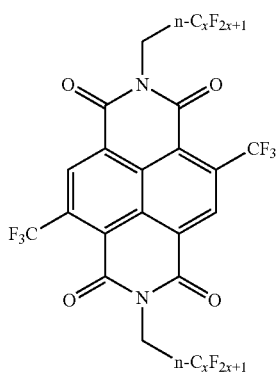
(94)
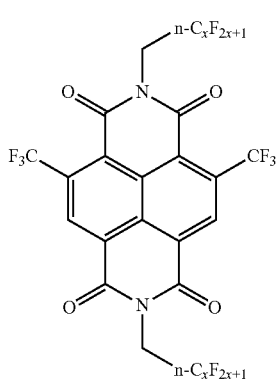
(95)
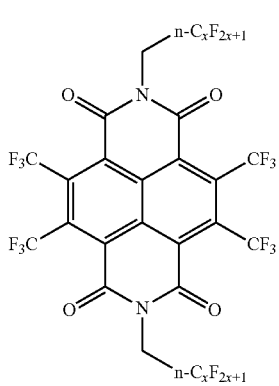
(96)
(x = 2, 3, 4)
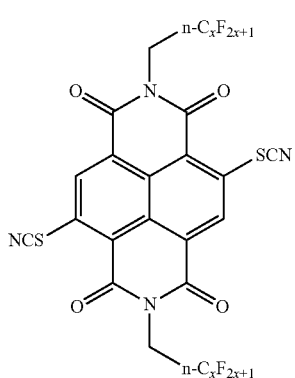
(97)
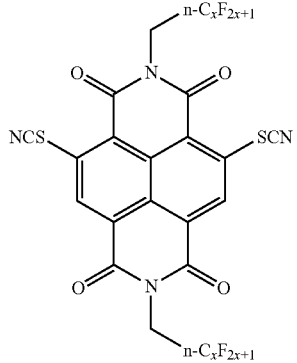
(98)
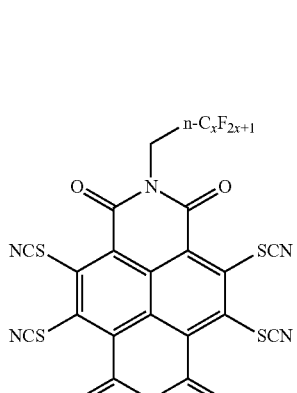
(99)
(x = 2, 3, 4)
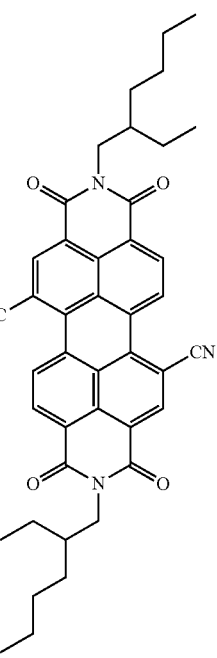
(100)

(101)
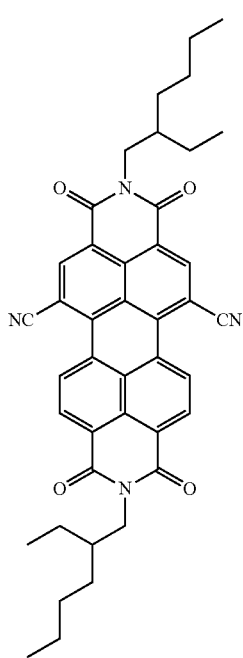
(102)
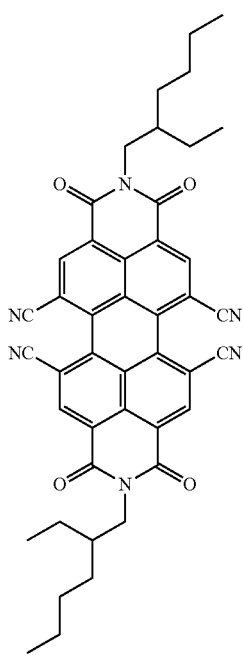
(103)
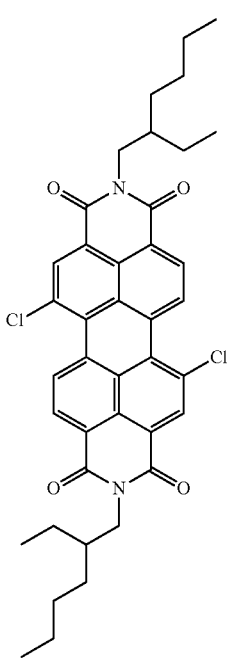
(104)
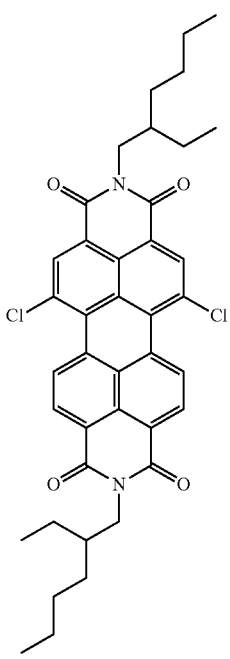

(105)
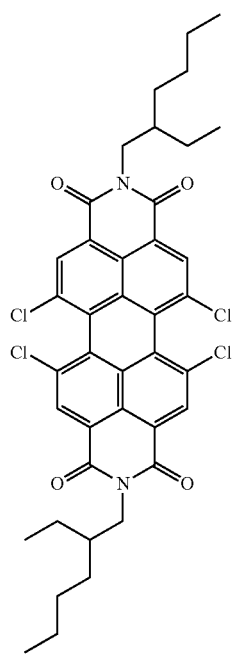
(107)
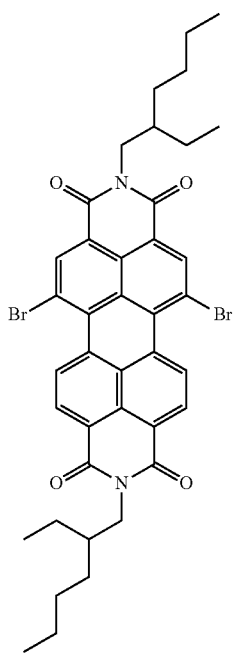
(106)
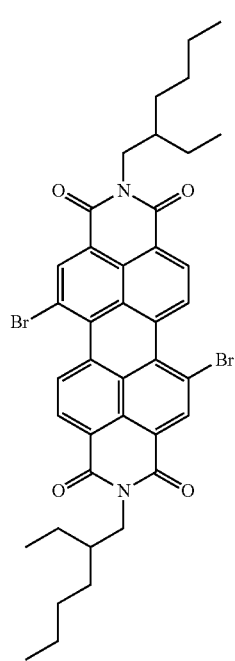
(108)
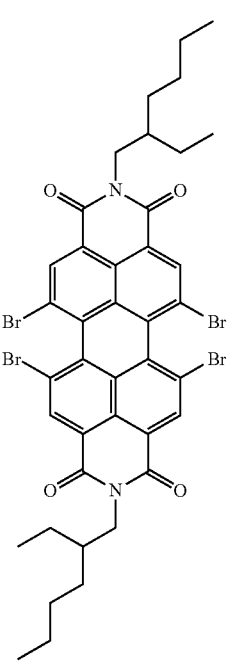

(109)
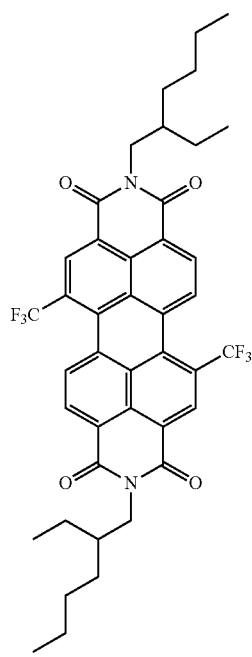
(110)
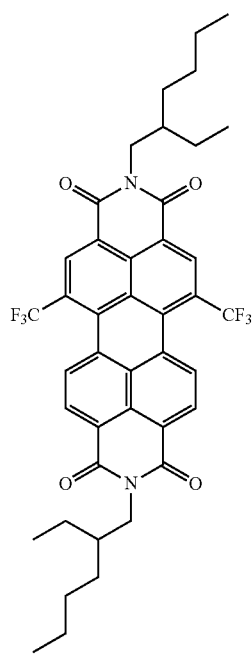
(111)
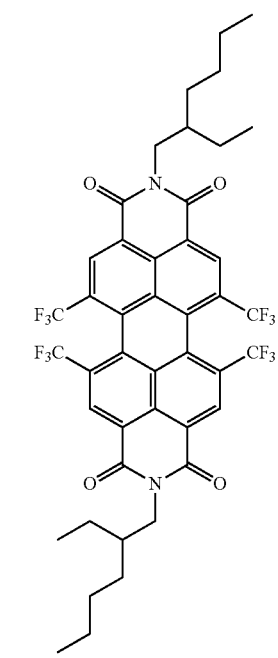
(112)
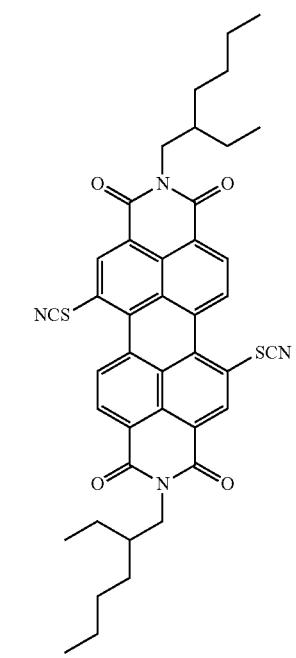

(113)
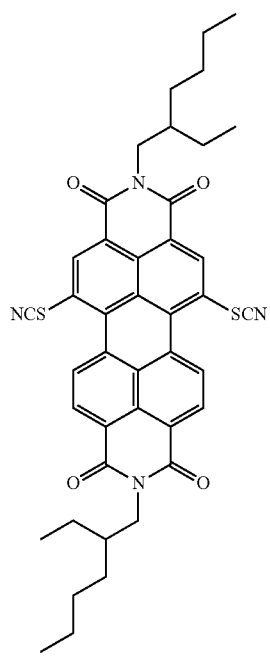
(114)
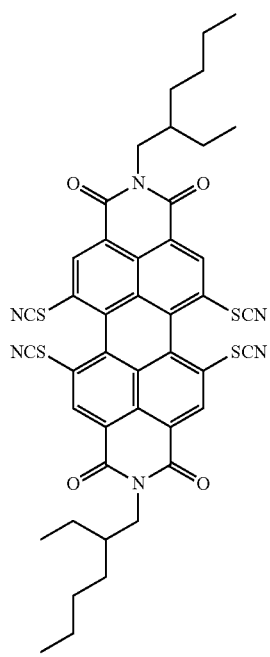
(115)
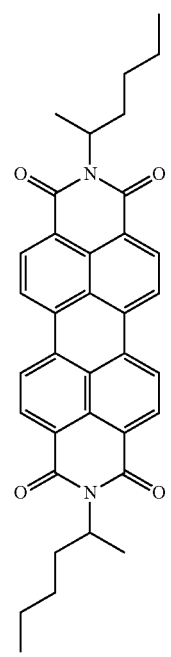
(116)
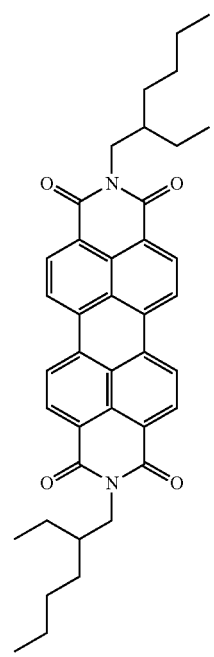

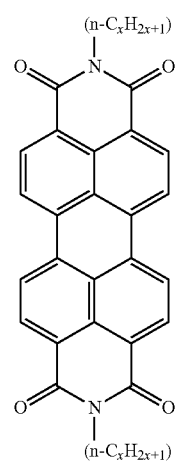
(117)
(X = 6, 7, 8, 9, 10, 11, 12)
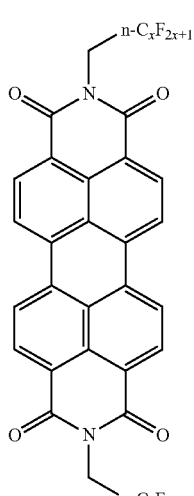
(118)
(X = 2, 3, 4)
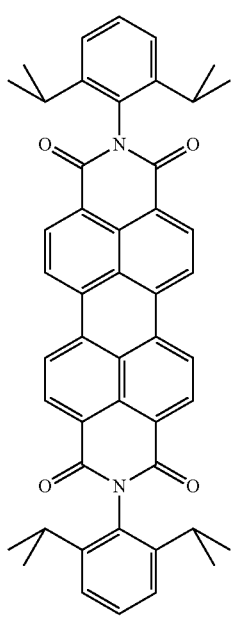
(119)
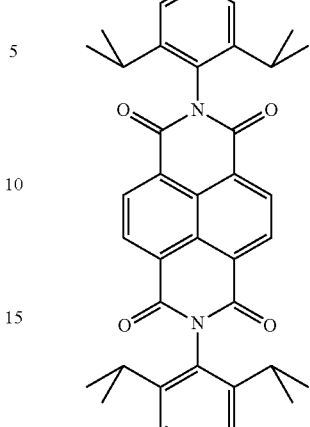
(120)
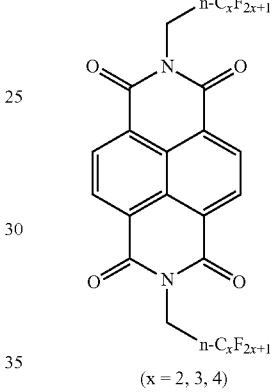
(121)
(x = 2, 3, 4)
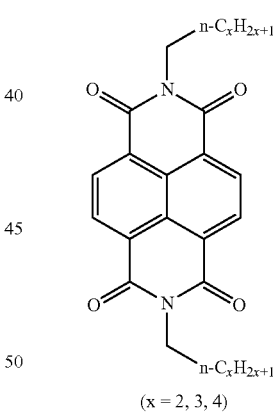
(122)
(x = 2, 3, 4)
In a further preferred embodiment, component A) comprises at least one compound of the formula (I.b)
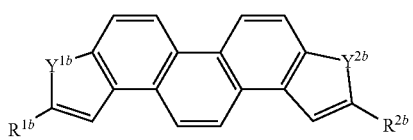
(I.b)
wherein
$R^{1b}$ and $R^{2b}$ are independently selected from hydrogen and in each case unsubstituted or substituted linear $C_1$-$C_{30}$- alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1b}$ and $Y^{2b}$ are independently selected from O, S, Se and $NR^{3b}$, where $R^{3b}$ is selected from hydrogen and in each case unsubstituted or substituted alkyl, cycloalkyl and aryl, Suitable compounds of the formula (I.b) and methods for their preparation are described in WO 2013/168048 which is incorporated herein by reference.

Preferably, $R^{1b}$ and $R^{2b}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1b}$ and $R^{2b}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1b}$ and $R^{2b}$ are independently selected from hydrogen, unsubstituted linear $C_1$-$C_{30}$-alkyl and unsubstituted branched $C_3$-$C_{30}$-alkyl.

Preferably, in the compounds of the formula (I.b1) $R^{1b}$ and $R^{2b}$ have the same meaning.

In a preferred embodiment, the compounds of the formula (I.b) are selected from compound of the formula (I.b1)

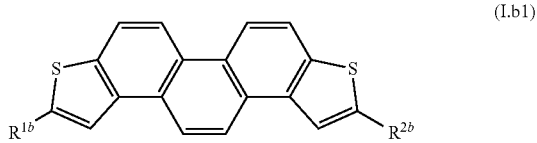

(I.b1)

wherein
$R^{1b}$ and $R^{2b}$ are independently selected from linear $C_7$-$C_{22}$-alkyl and branched $C_7$-$C_{22}$-alkyl.

Preferably, in the compounds of the formula (I.b1) $R^{1b}$ and $R^{2b}$ have the same meaning.

In a special embodiment, $R^{1b}$ and $R^{2b}$ have the same meaning and are selected from linear $C_7$-$C_{22}$-alkyl.

In a further preferred embodiment, component A) comprises at least one compound of the formula (I.c)

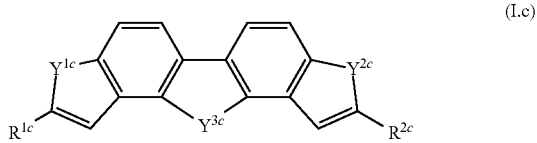

(I.c)

wherein
$R^{1c}$ and $R^{2c}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1c}$, $Y^{2c}$ and $Y^{3c}$ are independently selected from O, S, Se and $NR^{3c}$, where $R^{3c}$ is selected from hydrogen and in each case unsubstituted or substituted alkyl, cycloalkyl and aryl, Suitable compounds of the formula (I.c) and methods for their preparation are described in PCT/162015/051226 which is incorporated herein by reference.

Preferably, $Y^{1c}$, $Y^{2c}$ and $Y^{3c}$ are all S.

Preferably, $R^{1c}$ and $R^{2c}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1c}$ and $R^{2c}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1c}$ and $R^{2c}$ are independently selected from hydrogen, unsubstituted linear $C_1$-$C_{30}$-alkyl and unsubstituted branched $C_3$-$C_{30}$-alkyl.

In one special embodiment of the compounds of the formula (I.c) $R^{1c}$ is hydrogen and $R^{2c}$ is selected from linear $C_1$-$C_{30}$-alkyl and branched $C_3$-$C_{30}$-alkyl.

In a further special embodiment of the compounds of the formula (I.c) $R^{1c}$ and $R^{2c}$ are both selected from linear $C_1$-$C_{30}$-alkyl and branched $C_3$-$C_{30}$-alkyl.

In a preferred embodiment, the compounds of the formula (I.c) are selected from compound of the formula (I.c1) and (I.c2)

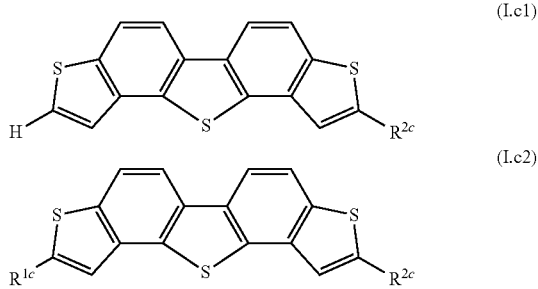

(I.c1)

(I.c2)

wherein
$R^{1c}$ and $R^{2c}$ are independently selected from linear $C_7$-$C_{22}$-alkyl and branched $C_7$-$C_{22}$-alkyl.

Preferably, in the compounds of the formula (I.c1) $R^{2c}$ is selected from linear $C_7$-$C_{22}$-alkyl.

Preferably, in the compounds of the formula (I.c2) $R^{1c}$ and $R^{2c}$ have the same meaning.

In a special embodiment, $R^{1c}$ and $R^{2c}$ have the same meaning and are selected from linear $C_7$-$C_{22}$-alkyl. Preferably, $R^{1c}$ and $R^{2c}$ have the same meaning and are selected from n-hexyl, n-heptyl, n-octyl, n-nonyl, n-decyl, n-undecyl and n-dodecyl.

In a further preferred embodiment, component A) comprises at least one compound of the formula (I.d)

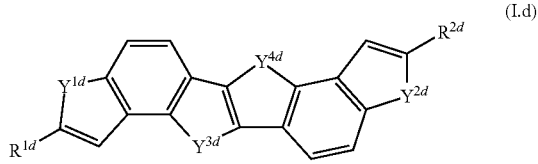

(I.d)

wherein
$R^{1d}$ and $R^{2d}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1d}$, $Y^{2d}$, $Y^{3d}$ and $Y^{4d}$ are independently selected from O, S, Se and $NR^{3d}$, where $R^{3d}$ is selected from hydrogen and in each case unsubstituted or substituted alkyl, cycloalkyl and aryl.

Suitable compounds of the formula (I.d) and methods for their preparation are described in WO/2014/087300 which is incorporated herein by reference.

Preferably, $Y^{1d}$, $Y^{2d}$, $Y^{3d}$ and $Y^{4d}$ are all S.

Preferably, $R^{1d}$ and $R^{2d}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1d}$ and $R^{2d}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1d}$ and $R^{2d}$ are independently selected from hydrogen, unsubstituted linear $C_1$-$C_{30}$-alkyl and unsubstituted branched $C_3$-$C_{30}$-alkyl.

In one special embodiment of the compounds of the formula (I.d) $R^{1d}$ is hydrogen and $R^{2d}$ is selected from linear $C_1$-$C_{30}$-alkyl and branched $C_3$-$C_{30}$-alkyl.

In a further special embodiment of the compounds of the formula (I.d) $R^{1d}$ and $R^{2d}$ are both selected from linear $C_1$-$C_{30}$-alkyl and branched $C_3$-$C_{30}$-alkyl.

In a preferred embodiment, the compounds of the formula (I.d) are selected from compound of the formula (I.d1) and (I.d2)

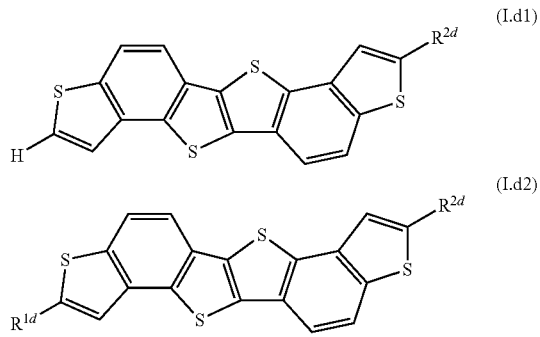

wherein
$R^{1d}$ and $R^{2d}$ are independently selected from linear $C_7$-$C_{22}$-alkyl and branched $C_7$-$C_{22}$-alkyl.

Preferably, in the compounds of the formula (I.d1) $R^{2d}$ selected from linear $C_7$-$C_{22}$-alkyl. More preferably, $R^{2d}$ is selected from n-hexyl, n-heptyl, n-octyl, n-nonyl, n-decyl, n-undecyl and n-dodecyl.

Preferably, in the compounds of the formula (I.d2) $R^{1d}$ and $R^{2d}$ have the same meaning.

In a special embodiment, $R^{1d}$ and $R^{2d}$ have the same meaning and are selected from linear $C_7$-$C_{22}$-alkyl. Preferably, $R^{1d}$ and $R^{2d}$ have the same meaning and are selected from n-hexyl, n-heptyl, n-octyl, n-nonyl, n-decyl, n-undecyl and n-dodecyl.

In a further preferred embodiment, component A) comprises at least one compound of the formula (I.e)

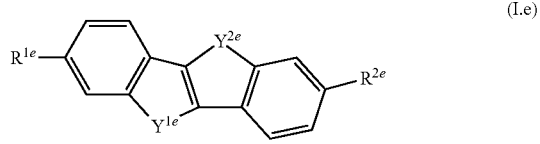

wherein
$R^{1e}$ and $R^{2e}$ are independently selected from hydrogen and in each case unsubstituted or substituted linear $C_1$-$C_{30}$-alkyl, branched $C_3$-$C_{30}$-alkyl, linear $C_2$-$C_{30}$-alkenyl, branched $C_3$-$C_{30}$-alkenyl, linear $C_2$-$C_{30}$-alkinyl, branched $C_4$-$C_{30}$-alkinyl, cycloalkyl, aryl and hetaryl, $Y^{1e}$ and $Y^{2e}$ are independently selected from O, S, Se and $NR^{3e}$, where $R^{3e}$ is selected from hydrogen and in each case unsubstituted or substituted alkyl, cycloalkyl and aryl.

Suitable compounds of the formula (I.e) and methods for their preparation are described in EP 2 077 590 B1 which is incorporated herein by reference.

Preferably, $Y^{1e}$ and $Y^{2e}$ are both S or are both Se. In particular, $Y^{1e}$ and $Y^{2e}$ are both S.

Preferably, $Y^{1e}$ and $Y^{2e}$ are independently selected from hydrogen, unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

Preferably, $R^{1e}$ and $R^{2e}$ are independently selected from hydrogen, unsubstituted linear $C_1$-$C_{30}$-alkyl, unsubstituted branched $C_3$-$C_{30}$-alkyl, linear $C_1$-$C_{30}$-fluoroalkyl and branched $C_3$-$C_{30}$-fluoroalkyl. In particular, $R^{1e}$ and $R^{2e}$ are independently selected from hydrogen, unsubstituted linear $C_1$-$C_{30}$-alkyl and unsubstituted branched $C_3$-$C_{30}$-alkyl.

Preferably, $R^{1e}$ is hydrogen and $R^{2e}$ is independently selected from unsubstituted linear $C_1$-$C_{30}$-alkyl, unsubstituted branched $C_3$-$C_{30}$-alkyl, halogen substituted linear $C_1$-$C_{30}$-alkyl and halogen substituted branched $C_3$-$C_{30}$-alkyl.

In a special embodiment of the compounds of the formula (I.e) $R^{1e}$ and $R^{2e}$ are both selected from linear $C_1$-$C_{30}$-alkyl and branched $C_3$-$C_{30}$-alkyl.

In a preferred embodiment, the compounds of the formula (I.e) are selected from compound of the formula (I.e1) and (I.e2)

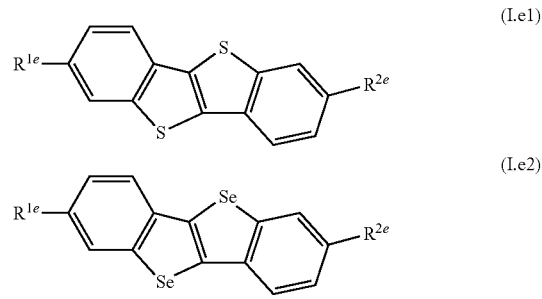

wherein
$R^{1e}$ and $R^{2e}$ are independently selected from unsubstituted linear $C_7$-$C_{22}$-alkyl and unsubstituted branched $C_7$-$C_{22}$-alkyl.

Preferably, in the compounds of the formulae (I.e1) and (I.e2) $R^{1e}$ and $R^{2e}$ have the same meaning.

Preferably, in the compounds of the formulae (I.e1) and (I.e2) $R^{1e}$ and $R^{2e}$ are selected from linear $C_7$-$C_{22}$-alkyl. Preferably, $R^{1e}$ and $R^{2e}$ have the same meaning and are selected from n-heptyl, n-octyl, n-nonyl, n-decyl, n-undecyl and n-dodecyl.

Component B)

The composition according to the invention comprises as component B) at least one compound that is liquid at 20° C. and 1013 mbar, selected from compounds of the formula (II)

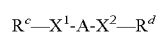

wherein

A is a 5- to 8-membered unsubstituted or substituted, aliphatic or aromatic carbocycle or heterocycle, $X^1$ and $X^2$ are independently selected from *—(C=O)—O—, *—(CH$_2$)$_m$—O— or *—(CH$_2$)$_m$—O—(C=O)—, where * is the point of linkage to the aliphatic or aromatic carbocycle or heterocycle, and m has the value 0, 1, or 2; and $R^c$ and $R^d$ are independently selected from unbranched and branched $C_1$-$C_{12}$-alkyl and $C_2$-$C_{12}$-alkenyl.

In a preferred embodiment, the at least one organic semiconductor A) has a solubility in component B) at 20° C. of at least 0.01 mg/ml, more preferably of at least 0.05 mg/ml.

If the at least one organic semiconductor A) has a solubility in component B) at 20° C. of less than 0.01 mg/ml, an additional cosolvent C), selected from organic solvents and mixtures of organic solvents different from component B), can be added to the composition according to the invention. Thus, in a further preferred embodiment the organic semiconductor A) has a solubility in the mixture of components B) and C) at 20° C. of at least 0.01 mg/ml, preferably of at least 0.05 mg/ml.

It is of course also possible to employ an additional cosolvent C) if the at least one organic semiconductor A) has a sufficient solubility in component B) alone. In this case, the additional cosolvent may be added to provide certain application properties, e.g. a good processability of the composition by a printing process.

Preferably, the component B) is present in an amount of 0.1 to 99.9999999 wt.-%, preferably in an amount of 0.5 to 99.999999 wt.-%, more preferably in an amount of 1.0 to 99.99999 wt.-%, in particular in an amount of 10 to 99.99999 wt.-%, based on the total weight of the composition.

Preferably, the component B) is present in an amount of 0.1 to 99.9999999 wt.-%, preferably in an amount of 0.5 to 99.999999 wt.-%, more preferably in an amount of 1.0 to 99.99999 wt.-%, in particular in an amount of 10 to 99.99999 wt.-%, based on the total weight of components A) and B).

Interactions between solvent and the component to be solubilized are in most cases dipole interactions (Debeye, London and Keesom). A good set of parameters for the characterization of solvents are the Hansen solubility parameters. Hansen divides the solubility parameter (delta) in three groups, dispersive interactions (delta D) dipole interactions (delta P) and hydrogen bonds (delta H). These interactions are regarded as independent of each other. Thus, the solubility parameter (delta) can be calculated as follows:

$$\delta^2 = (\delta D)^2 + (\delta P)^2 + (\delta H)^2$$

Preferably, component B) comprises at least one compound of the formula (II) with a Hansen solubility parameter (delta D) in the range of from 15 to 20, more preferably 16 to 19 mPa$^{1/2}$. In a special embodiment, component B) consists of at least one compound of the formula (II) with a Hansen solubility parameter (delta D) in the range of from 15 to 20, more preferably 16 to 19 mPa$^{1/2}$.

Preferably, component B) comprises at least one compound of the formula (II) with a Hansen solubility parameter (delta P) in the range of from 7 to 12, more preferably 8 to 11 mPa$^{1/2}$. In a special embodiment, component B) consists of at least one compound of the formula (II) with a Hansen solubility parameter (delta D) in the range of from 7 to 12, more preferably 8 to 11 mPa$^{1/2}$.

Preferably, component B) comprises at least one compound of the formula (II) with a Hansen solubility parameter (delta H) in the range of from 3.5 to 5.5, more preferably 4 to 5 mPa$^{1/2}$. In a special embodiment, component B) consists of at least one compound of the formula (II) with a Hansen solubility parameter (delta H) in the range of from 3.5 to 5.5, more preferably 4 to 5 mPa$^{1/2}$.

Preferably, component B) comprises at least one compound of the formula (II) with a boiling point at 1013.25 mbar (=1 atm) of at least 100° C., more preferably of at least 150° C., in particular of at least 200° C. In a special embodiment, component B) consists of at least one compound of the formula (II) with a boiling point at 1013.25 mbar of at least 100° C., more preferably of at least 150° C., in particular of at least 200° C.

Preferably, component B) comprises at least one compound of the formula (II) with a boiling point at 1013.25 mbar in the range of 100 to 350° C., preferably 150 to 320° C. In a special embodiment, component B) consists of at least one compound of the formula (II) with a boiling point at 1013.25 mbar in the range of 100 to 350° C., preferably 150 to 320° C.

In the following the Hansen solubility parameters and boiling points of some preferred dialkyl phthalates B) are described:

Dibutyl Phthalate:
(delta D): 17.8 mPa$^{1/2}$
(delta P): 8.6 mPa$^{1/2}$
(delta H): 4.1 mPa$^{1/2}$
boiling point (1013.25 mbar): 340° C.

Diethyl Phthalate
(delta D): 17.6 mPa$^{1/2}$
(delta P): 9.6 mPa$^{1/2}$
(delta H): 4.5 mPa$^{1/2}$
boiling point (1013.25 mbar): 295° C.

Dimethyl Phthalate
(delta D): 18.6 mPa$^{1/2}$
(delta P): 10.8 mPa$^{1/2}$
(delta H): 4.9 mPa$^{1/2}$
boiling point (1013.25 mbar): 283° C.

Diallyl Phthalate
(delta D): 17.8 mPa$^{1/2}$
(delta P): 8.5 mPa$^{1/2}$
(delta H): 4.0 mPa$^{1/2}$
boiling point (1013.25 mbar): 165° C.

Preferably, the compound of the general formula (II) is selected from compounds of the formulae (II.1), (II.2), (II.3) and (II.4)

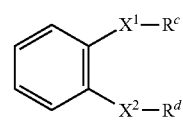

(II.1)

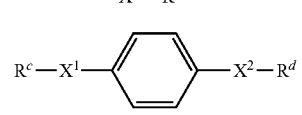

(II.2)

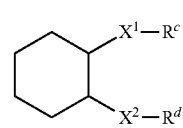

(II.3)

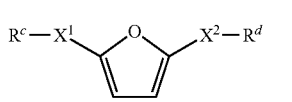

(II.4)

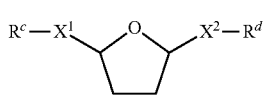

(II.5)

wherein
$X^1$ and $X^2$ are independently selected from *—(C=O)—O—, *—(CH$_2$)$_m$—O— or *—(CH$_2$)$_m$—O—(C=O)—, where * is the point of linkage to the aliphatic or aromatic carbocycle or heterocycle, and m has the value 0, 1, or 2; and
$R^c$ and $R^d$ are independently selected from unbranched and branched $C_1$-$C_{12}$-alkyl and $C_2$-$C_{12}$-alkenyl.

It is preferable that the moieties $R^c$ and $R^d$ in the compounds of the formulae (II), (II.1), (II.2), (II.3), (II.4) and (II.5) are independently of each other an unbranched or branched $C_7$-$C_{12}$-alkyl moiety.

Preferably, the moieties $R^c$ and $R^d$ in the compounds of the formulae (II), (II.1), (II.2), (II.3), (II.4) and (II.5) have the same meaning.

Preferably, in the compounds of the formulae (II), (II.1), (II.2), (II.3), (II.4) and (II.5) $R^c$ and $R^d$ are independently selected methyl, ethyl, n-propyl, isopropyl, n-butyl, sec.-butyl, tert.-butyl, isobutyl, n-pentyl, n-hexyl, n-heptyl, n-octyl, 2-ethylhexyl, n-nonyl, isononyl, isodecyl, 2-propylheptyl, n-undecyl and isoundecyl.

Preferably, in the compounds of the formulae (II), (II.1), (II.2), (II.3), (II.4) and (II.5) the groups $X^1$ and $X^2$ are both *—(C=O)—O—.

In particular, the compound of the formula II.1 is selected from dimethylphthalate, diethylphthalate, di(n-propyl)phthalate, di(n-butyl)phthalate, diallylphthalate and mixtures thereof.

Suitable compounds of the general formula (II) and of the formulae (II.1), (II.2), (II.3) and (II.4) and methods for their production are known to a person skilled in the art. Those compounds have long been known as plasticizers, i.e. additives that are used to achieve desired processing properties or desired performance characteristics in many plastics. Phthalic diesters (II.1) and terephthalic diesters (II.2) with alcohols of different chemical structure have in the past often been used as plasticizers because they have good compatibility with PVC and advantageous performance characteristics. Short-chain phthalates, e.g. dibutyl phthalate (DBP), diisobutyl phthalate (DIBP), etc. are also used as gelling aids ("fast fuser").

Dialkylcyclohexane-1,2-dicarboxylic esters (II.3) can either be purchased or produced by processes known in the prior art. The 1,2-cyclohexanedicarboxylic esters are generally obtained mostly via ring-hydrogenation of the corresponding phthalic esters. The ring-hydrogenation can take place as mentioned above by the process described in WO 99/32427. A particularly suitable ring-hydrogenation process is also described by way of example in WO 2011/082991 A2. 1,2-Cyclohexanedicarboxylic esters can moreover be obtained via esterification of 1,2-cyclohexanedicarboxylic acid or of suitable derivatives thereof with the corresponding alcohols. The esterification can take place by conventional processes known to the person skilled in the art.

The esters of 2,5-furandicarboxylic acid (FDCA=component II.4) are another plasticizer class. R. D. Sanderson et al. (J. Appl. Pol. Sci., 1994, vol. 53, 1785-1793) describe the synthesis of esters of 2,5-furandicarboxylic acids and their use as plasticizers. WO 2012/113608 describes $C_5$-dialkyl esters of 2,5-furandicarboxylic acid, WO 2012/113609 describes $C_7$-dialkyl esters of 2,5-furandicarboxylic acid, WO 2011/023490 describes $C_9$-dialkyl esters of 2,5-furandicarboxylic acid and WO 2011/023491 describes $C_{10}$-dialkyl esters of 2,5-furandicarboxylic acid.

Preferably, the compounds of the formula (II.2) are selected from di methylterephthalate, diethylterephthalate, di(n-propyl)terephthalate, di(n-butyl)terephthalate, diallylterephthalate and mixtures thereof.

Preferably, the compounds of the formula (II.3) are selected from dimethyl-1,2-cyclohexanedicarboxylate, diethyl-1,2-cyclohexanedicarboxylate, di(n-propyl)-1,2-cyclohexanedicarboxylate, di(n-butyl)-1,2-cyclohexanedicarboxylate, diallyl-1,2-cyclohexanedicarboxylate and mixtures thereof.

Preferably, the compounds of the formula (II.4) are selected from dimethyl-2,5-furandicarboxylate, diethyl-2,5-furandicarboxylate, di(n-propyl)-2,5-furandicarboxylate, di(n-butyl)-2,5-furandicarboxylate, diallyl-2,5-furandicarboxylate and mixtures thereof.

Preferably, the diesters of 2,5-tetrahydrofurandicarboxylic acid of the formula (II.5)

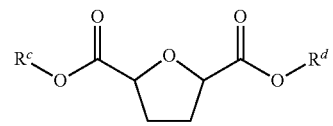

(II.5)

in which
$R^c$ and $R^d$ are independently selected from unbranched and branched $C_1$-$C_{12}$-alkyl and $C_2$-$C_{12}$-alkenyl
are prepared by a method wherein
a) optionally 2,5-furandicarboxylic acid or an anhydride or acyl halide thereof is reacted with a $C_1$-$C_3$-alkanol in the presence of a catalyst to give a di($C_1$-$C_3$-alkyl) 2,5-furandicarboxylate,
b1) 2,5-furandicarboxylic acid or an anhydride or acyl halide thereof, or the di($C_1$-$C_3$-alkyl) 2,5-furandicarboxylate obtained in step a), is reacted with at least one alcohol $R^c$—OH and, if $R^c$ and $R^d$ are different, also with at least one alcohol $R^d$—OH, in the presence of at least one catalyst to give a compound of the formula (II.5a),

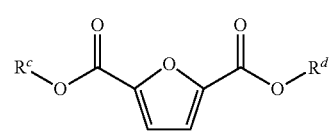

(II.5a)

c1) the compound (II.5a) obtained in step b1) is hydrogenated with hydrogen in the presence of at least one hydrogenation catalyst to give the compound of the general formula (II.5),
or
b2) 2,5-furandicarboxylic acid or the di($C_1$-$C_3$-alkyl) 2,5-furandicarboxylate obtained in step a) is hydrogenated with hydrogen in the presence of at least one hydrogenation catalyst to give a compound of the general formula (II.5b),

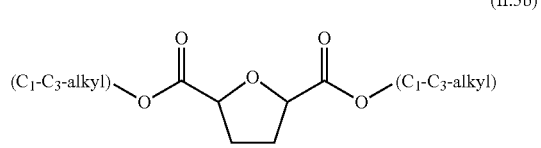

(II.5b)

c2) the compound (II.5b) obtained in step b2) is reacted with at least one alcohol
$R^c$—OH and, if $R^c$ and $R^d$ are different, also with at least one alcohol $R^d$—OH, in the presence of a catalyst to give a compound of the formula (II.5).

Preferably, the compounds of the formula (II.5) are selected from dimethyl-2,5-tetrahydrofurandicarboxylate, diethyl-2,5-tetrahydrofurandicarboxylate, di(n-propyl)-2,5-tetrahydrofurandicarboxylate, di(n-butyl)-2,5-tetrahydrofurandicarboxylate, diallyl-2,5-tetrahydrofurandicarboxylate and mixtures thereof.

The afore-mentioned process permits the production of the 2,5-tetrahydrofurandicarboxylic esters of the general formula (II.5) by two different routes (hereinafter termed variant 1 and variant 2).

Examples of $C_1$-$C_3$-alkanols suitable for use in step a) are methanol, ethanol, n-propanol, and mixtures thereof.

In variant 1 of the process of the invention, the 2,5-furandicarboxylic acid or the di($C_1$-$C_3$-alkyl) 2,5-furandicarboxylate obtained in step a) is subjected to esterification or transesterification with at least one alcohol $R^c$—OH and, if $R^c$ and $R^d$ are different, also with at least one alcohol $R^d$—OH, to give the compounds of the formula (II.5a), which are then hydrogenated to give compounds of the general formula (II.5) (step c1)).

In variant 2, the 2,5-furandicarboxylic acid or the 2,5-di($C_1$-$C_3$-alkyl) furandicarboxylate obtained in step a) is first hydrogenated to give 2,5-tetrahydrofurandicarboxylic acid or, respectively, a compound of the general formula (I.1b) (step b2)), and the hydrogenation product is then reacted with at least one alcohol $R^c$—OH and, if $R^c$ and $R^d$ are different, also with at least one alcohol $R^d$—OH to give the compounds of the general formula (II.5) (step c2)).

Conventional processes known to the person skilled in the art can be used to convert the 2,5-furandicarboxylic acid (FDCA) or the 2,5-tetrahydrofurandicarboxylic acid to the corresponding ester compounds of the general formulae (II.5), (II.5a), and (II.5b). Among these is the reaction of at least one alcohol component selected from $C_1$-$C_3$-alkanols or from the alcohols $R^c$—OH and, respectively, $R^d$—OH with FDCA or a suitable derivative thereof. Examples of suitable derivatives are the acyl halides and anhydrides. A preferred acyl halide is the acyl chloride. Esterification catalysts that can be used are the catalysts conventionally used for this purpose, e.g. mineral acids, such as sulfuric acid and phosphoric acid; organic sulfonic acids, such as methanesulfonic acid and p-toluenesulfonic acid; amphoteric catalysts, in particular titanium compounds, tin(IV) compounds, or zirconium compounds, e.g. tetraalkoxytitanium compounds, e.g. tetrabutoxytitanium, and tin(IV) oxide. The water produced during the reaction can be removed by conventional measures, e.g. by distillation. WO 02/038531 describes a process for producing esters where a) a mixture consisting essentially of the acid component or an anhydride thereof and of the alcohol component is heated to boiling point in the presence of an esterification catalyst in a reaction zone, b) the vapors comprising alcohol and water are fractionated to give an alcohol-rich fraction and a water-rich fraction, c) the alcohol-rich fraction is returned to the reaction zone, and the water-rich fraction is discharged from the process. Esterification catalysts used are the above-mentioned catalysts. An effective amount of the esterification catalyst is used and is usually in the range from 0.05 to 10% by weight, preferably from 0.1 to 5% by weight, based on the entirety of acid component (or anhydride) and alcohol component. Other detailed descriptions of the conduct of esterification processes are found by way of example in U.S. Pat. Nos. 6,310,235, 5,324,853, DE-A 2612355 (Derwent Abstract No. DW 77-72638 Y) or DE-A 1945359 (Derwent Abstract No. DW 73-27151 U). The entirety of the documents mentioned is incorporated herein by way of reference.

The esterification can generally take place at ambient pressure or at reduced or elevated pressure. It is preferable that the esterification is carried out at ambient pressure or reduced pressure.

The esterification can be carried out in the absence of any added solvent or in the presence of an organic solvent.

If the esterification is carried out in the presence of a solvent, it is preferable that the organic solvent used is inert under the reaction conditions. Among these are by way of example aliphatic hydrocarbons, halogenated aliphatic hydrocarbons, and aromatic and substituted aromatic hydrocarbons and ethers. It is preferable that the solvent is one selected from pentane, hexane, heptane, ligroin, petrol ether, cyclohexane, dichloromethane, trichloromethane, tetrachloromethane, benzene, toluene, xylene, chlorobenzene, dichlorobenzenes, dibutyl ether, THF, dioxane, and mixtures thereof.

The esterification is usually carried out in the temperature range from 50 to 250° C.

If the esterification catalyst is one selected from organic acids or mineral acids, the esterification is usually carried out in the temperature range from 50 to 160° C.

If the esterification catalyst is one selected from amphoteric catalysts, the esterification is usually carried out in the temperature range from 100 to 250° C.

The esterification can take place in the absence of or in the presence of an inert gas. Conventional processes known to the person skilled in the art can be also used for the reaction, described in steps b1) and c2), of the di($C_1$-$C_3$-alkyl) 2,5-furandicarboxylates and, respectively, the di($C_1$-$C_3$-alkyl) 2,5-tetrahydrofurandicarboxylates to give the corresponding ester compounds II.5a and, respectively, II.5. Among these are the reaction of the di($C_1$-$C_3$)-alkyl esters with at least one $C_7$-$C_{12}$-alkanol or a mixture thereof in the presence of a suitable transesterification catalyst.

Transesterification catalysts that can be used are the conventional catalysts usually used for transesterification reactions, where these are mostly also used in esterification reactions. Among these are by way of example mineral acids, such as sulfuric acid and phosphoric acid; organic sulfonic acids, such as methanesulfonic acid and p-toluenesulfonic acid; and specific metal catalysts from the group of the tin(IV) catalysts, for example dialkyltin dicarboxylates, such as dibutyltin diacetate, trialkyltin alkoxides, monoalkyltin compounds, such as monobutyltin dioxide, tin salts, such as tin acetate, or tin oxides; from the group of the titanium catalysts: monomeric and polymeric titanates and titanium chelates, for example tetraethyl orthotitanate, tetrapropyl orthotitanate, tetrabutyl orthotitanate, triethanolamine titanate; from the group of the zirconium catalysts:

zirconates and zirconium chelates, for example tetrapropyl zirconate, tetrabutyl zirconate, triethanolamine zirconate; and also lithium catalysts, such as lithium salts, lithium alkoxides; and aluminum(III) acetylacetonate, chromium (III) acetylacetonate, iron(III) acetylacetonate, cobalt(II) acetylacetonate, nickel(II) acetylacetonate, and zinc(II) acetylacetonate.

The amount of transesterification catalyst used is from 0.001 to 10% by weight, preferably from 0.05 to 5% by weight. The reaction mixture is preferably heated to the boiling point of the reaction mixture, the reaction temperature therefore being from 20° C. to 200° C., depending on the reactants.

The transesterification can take place at ambient pressure or at reduced or elevated pressure. It is preferable that the transesterification is carried out at a pressure of from 0.001 to 200 bar, particularly from 0.01 to 5 bar. The relatively low-boiling-point alcohol eliminated during the transesterification is preferably continuously removed by distillation in order to shift the equilibrium of the transesterification reaction. The distillation column necessary for this purpose generally has direct connection to the transesterification reactor, and it is preferable that said column is a direct attachment thereto. If a plurality of transesterification reactors are used in series, each of said reactors can have a distillation column, or the vaporized alcohol mixture can preferably be introduced into a distillation column from the final tanks of the transesterification reactor cascade by way of one or more collection lines. The relatively high-boiling-point alcohol reclaimed in said distillation is preferably returned to the transesterification.

The transesterification can be carried out in the absence of, or in the presence of, an added organic solvent. It is preferable that the transesterification is carried out in the presence of an inert organic solvent. Suitable organic solvents are those mentioned above for the esterification. Among these are specifically toluene and THF.

The transesterification is preferably carried out in the temperature range from 50 to 200° C.

The transesterification can take place in the absence of or in the presence of an inert gas.

Many processes and catalysts for the hydrogenation of the double bonds of the furan ring carried out in steps c1) and b2) of the invention are available to the person skilled in the art and these by way of example are also used in the hydrogenation of esters of aromatic polycarboxylic acids, examples being phthalates, isophthalates and terephthalates. By way of example, the ring-hydrogenation process described in WO 99/032427 is suitable. This comprises hydrogenation at from 50 to 250° C. and at a pressure of from 20 to 300 bar by means of catalysts which comprise at least one metal of transition group VIII of the Periodic Table of the Elements, for example platinum, rhodium, palladium, cobalt, nickel, or ruthenium, preferably ruthenium, either alone or together with at least one metal from transition group I or VII of the Periodic Table of the Elements, for example copper or ruthenium, deposited on a mesoporous aluminum oxide support material with bimodal pore distribution. The ring-hydrogenation process described in WO 02/100536 is moreover suitable. This comprises hydrogenation with use of a ruthenium catalyst on amorphous silicon dioxide as support. Other suitable processes are described in the following documents: EP-A 1266882—Use of a nickel/magnesium oxide on kieselguhr catalyst, WO 03/029181—Use of a nickel/zinc on silicon dioxide catalyst, WO 03/029168-Use of a palladium/ZnO on $Al_2O_3$ catalyst and of a ruthenium/ZnO on α-$Al_2O_3$ catalyst, or WO 04/09526—Use of a ruthenium on titanium dioxide catalyst. Other suitable catalysts are likewise Raney catalysts, preferably Raney nickel. Other suitable support materials alongside those already mentioned are by way of example zirconium dioxide ($ZrO_2$), sulfated zirconium dioxide, tungsten carbide (WC), titanium dioxide ($TiO_2$), sulfated carbon, activated charcoal, aluminum phosphate, aluminosilicates, or phosphated aluminum oxide, or else a combination thereof.

The hydrogenation can take place by analogy with the known hydrogenation processes for hydrogenating organic compounds which have hydrogenatable groups. To this end, the organic compound in the form of liquid phase or gas phase, preferably in the form of liquid phase, is brought into contact with the catalyst in the presence of hydrogen. The liquid phase can by way of example be passed over a fluidized bed of catalyst (fluidized bed method) or can be passed over a fixed bed of catalyst (fixed bed method).

The hydrogenation generally takes place under elevated hydrogen pressure. Preference is given to hydrogen pressure in the range from 2 to 500 bar, particularly from 10 to 300 bar.

It is preferable that the hydrogenation takes place in the presence of an organic solvent that is inert under the hydrogenation conditions. Suitable solvents are those previously defined for the esterification. Specifically, an ether is used, for example THF, or a dialkylene glycol, or a mono- or diether thereof, for example glyme.

The hydrogenation is preferably carried out at a temperature in the range from 20 to 350° C., particularly preferably from 50 to 300° C.

The amount of hydrogen used for the hydrogenation is generally from 1 to 15 times the stoichiometric amount of hydrogen theoretically needed for the complete hydrogenation of the furan ring.

Component C)

In certain embodiments, the composition according to the invention comprises a cosolvent C) selected from organic solvents different from component B) and mixtures of organic solvents different from component B).

Preferably, the organic semiconductor A) has a solubility in the mixture of components B) and C) at 20° C. of at least 0.1 mg/ml.

Preferably, the organic semiconductor A) has a solubility in component C) alone at 20° C. of at least 0.1 mg/ml.

Preferably, the component B) is present in an amount of 0.1 to 100 wt.-%, preferably in an amount of 1 to 100 wt.-%, more preferably in an amount of 10 to 100 wt.-%, in particular in an amount of 50 to 100 wt.-%, based on the total weight of components B) and C).

Preferably, the component C) is present in an amount of 0 to 99.9 wt.-%, preferably in an amount of 0 to 99 wt.-%, more preferably in an amount of 0 to 90 wt.-%, in particular in an amount of 0 to 50 wt.-%, based on the total weight of components B) and C).

If the composition according to the invention comprises a cosolvent C), the amount is preferably 0.1 to 99.9 wt.-%, more preferably 1 to 99 wt.-%, in particular 2 to 90 wt.-%, especially 3 to 50 wt.-%, based on the total weight of components B) and C).

Preferably, the cosolvent C) is selected from
aliphatic, cycloaliphatic and aromatic hydrocarbons,
aromatic ethers,
open chain aliphatic ethers, polyethers, ether alcohols and cyclic ethers,
ketones,
esters,
aliphatic and cycloaliphatic alcohols, benzene based alcohols,
halogenated aromatic compounds,
thiophenols and alkylthio-substituted benzenes,
aromatic compounds comprising a phenyl group fused to a 5-, 6-, or 7-membered cycloheteroalkyl group,
5-membered heteroaryl compounds and benzo-fused 5-membered heteroaryl compounds,
aromatic carboxylic acids,
aromatic aldehydes,
trifluoromethyl-substituted benzene compounds,
cyano-substituted or isocyano-substituted benzene compounds,
nitro-substituted benzene compounds,
phenyl sulfones,
6-membered heteroaryl compounds and benzofused 6-membered heteroaryl compounds,
5-membered heteroaryl compounds and benzofused 5-membered heteroaryl compounds,
aprotic polar solvents and
mixtures thereof.

Preferred aliphatic, cycloaliphatic and aromatic hydrocarbons are selected from n-pentane, n-hexane, n-heptan, ligroin, decaline, cyclohexane, methylcyclohexane, benzene, toluene, o-xylene, m-xylene, p-xylene, cumene, 1,2,3-trimethylbenzene, 1,2,4-trimethylbenzene, 1,3,5-trimethylbenzene, mesitylene, 1-methyl naphthalene, 2-methylnapthalene, 1-ethyl naphthalene, 2-ethylnapthalene, tetraline, indane, indene and mixtures thereof.

Preferred aromatic ethers are anisole (methylphenylether) ethoxybenzene (phenetol), propoxybenzene, isopropoxybenzene, butoxybenzene, 1-methoxynaphthalin, 2-methoxynaphthalin, 2-methylanisole, 3-methylanisole, 4-methylanisole, 2-ethylanisole, 3-ethylanisole, 4-ethylanisole, 2,3-dimethylanisole, 2,4-dimethylanisole, 2,5-dimethylanisole, 2,6-dimethylanisole, 3,4-dimethylanisole, 3,5-dimethylanisole, 1,2-dimethoxybenzene (veratrol), 1,3-dimethoxybenzene, 1,4-dimethoxybenzene, 1-ethoxy-4-methoxybenzene, 1-ethoxy-3-methoxybenzene, 1-ethoxy-2-methoxybenzene, 1,2-diethoxybenzene, 1,3-diethoxybenzene, 1,4-diethoxybenzene, 2,3-dimethoxytoluene, 2,4-dimethoxytoluene, 2,5-dimethoxytoluene, 2,6-dimethoxytoluene, 3,4-dimethoxytoluene, 3,5-dimethoxytoluene, 4-ethoxytoluene, 3-ethoxytoluene, 2-ethoxytoluene, 1-ethoxy-2-ethylbenzene, 1-ethoxy-3-ethylbenzene, 1-ethoxy-4-ethylbenzene, 1-(methoxymethoxy)benzene, (2-methoxyethoxy)benzene, (3-methoxypropoxy)benzene and mixtures thereof. A preferred cosolvent C) is anisole.

Preferred open chain aliphatic ethers, polyethers, ether alcohols and cyclic ethers are diethyl ether, dipropyl ether, diisopropyl ether, methyl tert-butyl ether, ethyleneglycolmonomethylether, ethyleneglycoldimethylether, ethyleneglycolmonoethylether, ethyleneglycoldiethylether, propyleneglycolmonomethylether, propyleneglycoldimethylether, propyleneglycolmonoethylether, propyleneglycoldiethylether, diethylenglycolmonomethylether, diethylenglycoldimethylether, diethylenglycolmonoethylether, diethylenglycoldiethylether, diglyme (=bis(2-methoxyethyl) ether), tetrahydrofuran, tetrahydropyran, 1,4-dioxane, morpholine and mixtures thereof.

Preferred ketones are acetone, methyl ethyl ketone, methyl isobutyl ketone, ethyl n-amyl ketone, diisobutyl ketone, cyclohexanone, pentane-2,4-dione (acetylacetone), acetophenone, 2-acetyltoluene, 3-acetyltoluene, 4-acetyltoluene, propiophenone, butyrophenone, valerophenone, hexanophenone and mixtures thereof. Preferred cosolvent C) are acetylacetone, acetophenone and mixtures thereof.

Preferred esters are ethyl acetate, methyl acetate, ethyl acetoacetate, propyl acetate, isopropyl acetate, n-butyl acetate, sec-butyl acetate, tert-butyl acetate, isobutyl acetate, isoamyl acetate, hexyl acetate, methyl propionate, ethyl butyrate, ethyl lactate, diethyl carbonate, ethylene carbonate, propylene carbonate, triacetin, phenyl formate, phenyl acetate, o-cresol acetate, p-cresol acetate, m-Cresol acetate, 2-methoxyphenyl acetate, 3-methoxyphenyl acetate, and 4-methoxyphenyl acetate, benzyl benzoate, bis(2-ethylhexyl) adipate, methyl benzoate, methyl 2-methylbenzoate, methyl 3-methylbenzoate, methyl 4-methylbenzoate, hexylbenzoate, pentylbenzoate, butylbenzoate, propylbenzoate, methyl 2-chlorobenzoate, methyl 3-chlorobenzoate, methyl 4-chlorobenzoate, methyl 4-fluorobenzoate, methyl 3-fluorobenzoate, methyl 2-fluorobenzoate, ethyl benzoate, ethyl 2-methyl benzoate, ethyl 3-methyl benzoate, ethyl 4-methylbenzoate, ethyl 4-chlorobenzoate, ethyl 3-chlorobenzoate, ethyl 2-chlorobenzoate, ethyl 2-fluorobenzoate, ethyl 3-fluorobenzoate, ethyl 4-fluorobenzoate, methyl 4-bromobenzoate, methyl 3-bromobenzoate, methyl 2-bromobenzoate and mixtures thereof.

Preferred aliphatic and cycloaliphatic alcohols are methanol, ethanol, n-propanol, isopropanol n-butanol, sec.-butanol, tert.-butanol, n-pentanol, amyl alcohol mixtures, n-hexanol, cyclohexanol, ethanediol, propanediol, ethylene glycol, diethylene glycol and mixtures thereof.

In preferred benzene-based alcohols the phenyl group can be directly substituted with a hydroxyl group, or the phenyl group can be substituted with an alkyl, alkoxy, alkylthio, or amino group, wherein the alkyl, alkoxy, alkylthio, or amino group is substituted with a hydroxyl group. Examples of benzene-based alcohols include phenol; cresol (o-cresol, m-cresol, p-cresol); 2-methoxyphenol, 3-methoxyphenol, 4-methoxyphenol, 4-aminobenzylalcohol; 2-phenoxyethanol; 3-phenoxy-1-propanol; 4-phenoxy-1-butanol; 5-phenoxy-1-heptanol; 6-phenoxy-1-hexanol; 2-(2-methylphenoxy)ethan-1-ol; 2-(3-methylphenoxy)ethan-1-ol; 2-(4-methylphenoxy)ethan-1-ol; phenoxymethanol; 1-phenoxyethanol, 1-phenoxypropanol, 1-phenoxybutanol, 2-(2-methoxyphenoxy)ethan-1-ol, 2-(3-methoxyphenoxy)ethan-1-ol; 2-(4-methoxyphenoxy)ethan-1-ol; 2-(2-methylphenoxy)ethanol, 2-(3-methylphenoxy)ethanol, 2-(4-methylphenoxy)ethanol, 2-(4-methoxyphenoxy)ethanol, 2-(3-methoxyphenoxy)ethan-1-ol, 2-(2-methoxyphenoxy)ethan-1-ol and mixtures thereof.

Preferred halogenated aromatic compounds are selected from chlorobenzene, 1,2-dichlorobenzene, 1,3-dichlorobenzene, 1,2,4-trichlorobenzene, 4-chlorotoluene, 3-chlorobenzene, 2-chlorotoluene, fluorobenzene, 1,2-difluorobenzene, 1,3-difluorobenzene, 1,4-difluorobenzene, 1-chloronaphthalene, 2-chloronaphthalene, 1-fluoronaphthalene, 2-fluoronaphthalene, 2-chloroanisole, 3-chloroanisole, 4-chloroanisole, 4-fluoroanisole, 3-fluoroanisole, 2-fluoroanisole, and mixtures thereof.

Examples of thiophenols include thiophenol, 2-thiocresol, 3-thiocresol, 4-thiocresol, 2-ethyl thiophenol, 3-ethyl thiophenol, 4-ethyl thiophenol, 2,6-dimethylthiophenol, 2,5-dimethylthiophenol, 2,4-dimethylthiophenol, 2,3-dimethylthiophenol, and 2-isopropylthiophenol. Examples of alkylthio-substituted benzenes include thioanisole, (ethylthio) benzene, 2-methylthioanisole, 3-methyl thioanisole, 4-methyl thioanisole, 4-methoxy thioanisole, 3-methoxy thioanisole, 2-methoxy thioanisole.

Suitable aromatic compounds comprising a phenyl group fused to a 5-, 6-, or 7-membered cycloheteroalkyl group include indoline and substituted indolines, such as 7-methylindoline, 5-methylindoline, and 6-methylindoline; 1,2,3, 4-tetrahydroquinoline; 6-methyl-3,4-dihydro-2H-1-benzopyran; benzodioxole and substituted benzodioxoles, such as 1,3-benzodioxole, 2-methyl-1,3-benzodioxole, 2-ethyl-1,3-benzodioxole, 5-hydroxy-1,3-benzodioxole, 5-methyl-1,3-benzodioxole, 5-methoxy-1,3-benzodioxole, 5-methyl-1,3-benzodioxole, 5-ethyl-1,3-benzodioxole, 4-hydroxy-1,3-benzodioxole, 4-methyl-1,3-benzodioxole, 4-ethyl-1,3-benzodioxole, 4-methoxy-1,3-benzodioxole, 2,2-dimethyl-1,3-benzodioxole, 3,4-methylenedioxytoluene, and 4-methyl-2H-1,3-benzodioxole; dihydrobenzofuran and substituted dihydrobenzofurans such as 2,3-dihydrobenzofuran, 2,3-dihydro-2-methylbenzofuran, 6-methyl-2,3-dihydrobenzofuran, and 5-methyl-2,3-dihydrobenzofuran; 4H-chromene, chromane, 7-methylchroman, 8-methylchroman, and 2,3-dihydrobenzo[b]thiophene.

Suitable 5-membered heteroaryl compounds and benzofused 5-membered heteroaryl compounds are thiophene, 2-methylthiophene, 3-methylthiophene, furan, 3-methylfuran, 2-methylfuran, pyrrole, N-methylpyrrole, N-ethylpyrrole, 1,2-dimethyl-1H-pyrrole, 1,3-dimethyl-1H-pyrrole, 2-methoxyfuran, 3-methoxyfuran, 3-methoxythiophene, 2-methoxythiophene, 2-methylthiofuran, 3-methylthiofuran, 3-methylthiothiophene, 2-methylthiothiophene, 2-N,N-dimethylamino-thiophene, 3-methoxy-1-methyl-1H-pyrrole, 2-methoxy-1-methyl-1H-pyrrole, benzofuran, 6-methylbenzofuran, benzothiophene, and 6-methylbenzothiophene.

Suitable aromatic carboxylic acids are benzoic acid, o-toluic acid, m-toluic acid, p-toluic acid, 4-chlorobenzoic acid, 3-chlorobenzoic acid, 2-chlorobenzoic acid, 2-fluorobenzoic acid, 3-fluorobenzoic acid, 4-fluorobenzoic acid and mixtures thereof.

Suitable aromatic aldehydes are benzaldehyde, 2-methylbenzaldehyde, 3-methylbenzaldehyde, 4-methylbenzaldehyde, 4-ethylbenzaldehyde, 3-ethyl benzaldehyde, 2-ethylbenzaldehyde, 2-chlorobenzaldehyde, 3-chlorobenzaldehyde, 4-chlorobenzaldehyde, 4-fluorobenzaldehyde, 3-fluorobenzaldehyde, 2-fluorobenzaldehyde, 2-bromobenzaldehyde, 3-bromobenzaldehyde, and 4-bromobenzaldehyde.

Suitable trifluoromethyl-substituted benzene compounds are benzotrifluoride, 2-methylbenzotrifluoride, 3-methylbenzotrifluoride, 4-methylbenzotrifluoride, 4-chlorobenzotrifluoride, 3-chlorobenzotrifluoride, 2-chlorobenzotrifluoride, 2-fluorobenzotrifluoride, 3-fluorobenzotrifluoride, 4-fluorobenzotrifluoride, 4-bromobenzotrifluoride, 3-bromobenzotrifluoride, 2-bromobenzotrifluoride, methyl 2-trifluoromethylbenzoate, methyl 3-trifluoromethylbenzoate, methyl 4-trifluoromethylbenzoate, ethyl 2-trifluoromethylbenzoate, ethyl 3-trifluoromethylbenzoate, ethyl 4-trifluoromethylbenzoate and mixtures thereof.

Suitable cyano-substituted or isocyano-substituted benzene compounds are benzonitrile, 2-methyl benzenecarbonitrile, 3-methylbenzenecarbonitrile, 4-methylbenzenecarbonitrile, 4-chlorobenzonitrile, 3-chlorobenzonitrile, 2-chlorobenzonitrile, 2-fluorobenzonitrile, 3-fluorobenzonitrile, 4-fluorobenzonitrile, phenylisocyanide, 2-tolylisocyanide, 3-tolylisocyanide, 4-tolyl isocyanide and mixtures thereof.

Suitable nitro-substituted benzene compounds are nitrobenzene, 2-nitrotoluene, 3-nitrotoluene, 4-nitrotoluene, 1-chloro-4-nitrobenzene, 1-chloro-3-nitrobenzene, 1-chloro-2-nitrobenzene, 1-fluoro-2-nitrobenzene, 1-fluoro-3-nitrobenzene, 1-fluoro-4-nitrobenzene and mixtures thereof.

Suitable phenyl sulfones are methyl phenyl sulfone, ethyl phenyl sulfone, (propane-1-sulfonyl)benzene, 1-methanesulfonyl-2-methyl-benzene, 1-methanesulfonyl-3-methylbenzene, and 1-methanesulfonyl-4-methyl-benzene.

Suitable 6-membered heteroaryl compounds or benzofused 6-membered heteroaryl compounds are pyridine, 2-methylpyridine, 3-methylpyridine, 4-methylpyridine, 2-chloropyridine, 3-chloropyridine, 4-chloropyridine, 4-fluoropyridine, 3-fluoropyridine, 2-fluoropyridine, 2-bromo-pyridine, 3-bromo-pyridine, 4-bromo-pyridine, 4-(trifluoromethyl)pyridine, 3-(trifluoromethyl)pyridine, 2-(trifluoromethyl)pyridine, 2-cyanopyridine, 3-cyanopyridine, 4-cyanopyridine, 4-nitropyridine, 3-nitropyridine, 2-nitropyridine, 2-picolinic acid methyl ester, 3-picolinic acid methyl ester, and 4-picolinic acid methyl ester; pyrazine and substituted pyrazines, such as methylpyrazine, 2,5-dimethylpyrazine, 2,6-dimethylpyrazine, 2,3-dimethylpyrazine, 2,3,5,6-tetramethyl-pyrazine, 2-chloropyrazine, 2,5-dichloropyrazine, 2,6-dichloropyrazine, 2,3-dichloropyrazine, 2-fluoropyrazine, (trifluoromethyl)pyrazine, 2-pyrazinecarbonitrile, 2-nitro-pyrazine, pyrazine-2-carbaldehyde, 1-pyrazin-2-yl-ethanone, 1-(pyrazin-2-yl)propan-1-one, methylpyrazine-2-carboxylate, pyrazine 2-carboxylic acid ethyl ester, 2-bromopyrazine, and 2-iodopyrazine; pyridazine and substituted pyridazines, such as 3-methylpyridazine, 4-methylpyridazine, 4,5-dimethylpyridazine, 3,6-dimethylpyridazine, 3-chloropyridazine, 4-chloropyridazine, pyridazine-3-carbonitrile, 4-pyridazinecarbonitrile, 4-(trifluoromethyl)pyridazine, 3-(trifluoromethyl)pyridazine, 3-nitropyridazine, pyridazine-3-carbaldehyde, pyridazine-4-carbaldehyde, 1-(pyridazin-4-yl)ethanone, 3-acetylpyridazine, methylpyridazine-3-carboxylate, and methylpyridazine-4-carboxylate; tetrazine and substituted tetrazines, such as 1,2,4,5-tetrazine, dimethyl-1,2,4,5-tetrazine, and 3,6-dichloro-1,2,4,5-tetrazine; quinoline and substituted quinolones, such as 2-methylquinoline, 3-methylquinoline, 4-methylquinoline, 5-methylquinoline, 6-methylquinoline, 7-methylquinoline, 8-methylquinoline, 2-chloroquinoline, 3-chloroquinoline, 4-chloroquinoline, 5-chloroquinoline, 6-chloroquinoline, 7-chloroquinoline, 8-chloroquinoline, 2-fluoroquinoline, 3-fluoroquinoline, 4-fluoroquinoline, 5-fluoroquinoline, 6-fluoroquinoline, 7-fluoroquinoline, 8-fluoroquinoline, 2-trifluoromethyl quinoline, 3-trifluoromethyl quinoline, 4-trifluoromethyl quinoline, 5-trifluoromethyl quinoline, 6-trifluoromethyl quinoline, 7-trifluoromethyl quinoline, 8-trifluoromethyl quinoline, 2-nitroquinoline, 3-nitroquinoline, 4-nitroquinoline, 5-nitroquinoline, 6-nitroquinoline, 7-nitroquinoline, 8-nitroquinoline, 2-acetylquinoline, 3-acetylquinoline, 4-acetylquinoline, 5-acetylquinoline, 6-acetylquinoline, 7-acetylquinoline, 8-acetylquinoline, 2-cyanoquinoline, 3-cyanoquinoline, 4-cyanoquinoline, 5-cyanoquinoline, 6-cyanoquinoline, 7-cyanoquinoline, 8-cyanoquinoline, methyl 2-quinolinecarboxylate, methyl 3-quinolinecarboxylate, methyl 4-quinolinecarboxylate, methyl 5-quinolinecarboxylate, methyl 6-quinolinecarboxylate, methyl 7-quinolinecarboxylate, ethyl 8-quinolinecarboxylate, ethyl 2-quinolinecarboxylate, ethyl 3-quinolinecarboxylate, ethyl 4-quinolinecarboxylate, ethyl 5 quinolinecarboxylate, ethyl 6-quinolinecarboxylate, ethyl 7-quinolinecarboxylate, ethyl 8-quinolinecarboxylate, 2-quinolinecarboxaldehyde, 3-quinolinecarboxaldehyde, 4-quinolinecarboxaldehyde, 5-quinolinecarboxaldehyde, 6-quinolinecarboxaldehyde, 7-quinolinecarboxaldehyde, 8-quinolinecarboxaldehyde, 1-(2-quinolinyl)-ethanone, 1-(3-quinolinyl)-ethanone, 1-(4-quinolinyl)-ethanone, 1-(5-quinolinyl)-ethanone, 1-(6-quinolinyl)-ethanone, 1-(7-quinolinyl)-ethanone, and 1-(8-quinolinyl)-ethanone; quinoxaline and substituted quinoxalines, such as 2-methylquinoxaline, 5-methylquinoxaline, 6-methylquinoxaline, 2-chloroquinoxaline, 5-chloroquinoxaline, 6-chloroquinoxaline, 2-fluoroquinoxaline, 5-fluoroquinoxaline, 6-fluoroquinoxaline, 2-cyanoquinoxaline, 5-cyanoquinoxaline, 6-cyanoquinoxaline, 2-nitroquinoxaline, 5-nitroquinoxaline, 6-nitroquinoxaline, 2-trifluoromethylquinoxaline, 5-trifluoromethylquinoxaline, 6-trifluoromethyquinoxaline, methyl 2-quinoxalinecarboxylate, methyl 5-quinoxalinecarboxylate, methyl 6-quinoxalinecarboxylate, ethyl 2-quinoxalinecarboxylate, ethyl 5-quinoxalinecarboxylate, ethyl 6-quinoxalinecarboxylate and mixtures thereof.

Suitable 5-membered heteroaryl compounds and benzo-fused 5-membered heteroaryl compounds are thiazole, 2-methylthiazole, 4-methylthiazole, 5-methylthiazole, 2-chlorothiazole, 4-chlorothiazole, 5-chlorothiazole, 2-fluorothiazole, 4-fluorothiazole, 5-fluorothiazole, 2-cyanothiazole, 4-cyanothiazole, 5-cyanothiazole, 2-nitrothiazole, 4-nitrothiazole, 5-nitrothiazole, methyl 1,3-thiazole-2-carboxylate, methyl 1,3-thiazole-5-carboxylate, methyl 1,3-thiazole-6-carboxylate, ethyl 1,3-thiazole-2-carboxylate, ethyl 1,3-thiazole-5-carboxylate, ethyl 1,3-thiazole-6-carboxylate, 2-trifluoromethylthiazole, 4-trifluoromethylthiazole, and 5-trifluoromethylthiazole; imidazole and substituted imidazoles, such as N-methyl imidazole, 2-methylimidazole, 4-methylimidazole, 5-methylimidazole, 2-chloroimidazole, 4-chloroimidazole, 5-chloroimidazole, 2-fluoroimidazole, 4-fluoroimidazole, 5-fluoroimidazole, 2-cyanoimidazole, 4-cyanoimidazole, 5-cyanoimidazole, 2-nitroimidazole, 4-nitroimidazole, 5-nitroimidazole, methyl imidazole-2-carboxylate, methyl imidazole-5-carboxylate, methyl imidazole-5-carboxylate, ethyl imidazole-2-carboxylate, ethyl imidazole-4-carboxylate, ethyl imidazole-5-carboxylate, 2-trifluoromethylimidazole, 4-trifluoromethylimidazole, 5-trifluoromethylimidazole, 2-methyl-N-methyl imidazole, 4-methyl-N-methyl imidazole, 5-methyl-N-methyl imidazole, 2-chloro-N-methyl imidazole, 4-chloro-N-methyl imidazole, 5-chloro-N-methyl imidazole, 2-fluoro-N-methyl imidazole, 4-fluoro-N-methyl imidazole, 5-fluoro-N-methyl imidazole, 2-cyano-N-methyl imidazole, 4-cyano-N-methyl imidazole, 5-cyano-N-methyl imidazole, 2-nitro-N-methyl imidazole, 4-nitro-N-methyl imidazole, 5-nitro-N-methyl imidazole, methyl N-methyl imidazole-2-carboxylate, methyl N-methyl imidazole-4-carboxylate, methyl N-methyl imidazole-5-carboxylate, ethyl N-methyl imidazole-2-carboxylate, ethyl N-methyl imidazole-4-carboxylate, ethyl N-methyl imidazole-5-carboxylate, 2-trifluoromethyl-N-methyl imidazole, 4-trifluoromethyl-N-methyl imidazole, and 5-trifluoromethyl-N-methyl imidazole; triazole and substituted triazoles such as 4-methyl-1,2,3-triazole, 5-methyl-1,2,3-triazole, 4-chloro-1,2,3-triazole, 5-chloro-1,2,3-triazole, 4-fluoro-1,2,3-triazole, 5-fluoro-1,2,3-triazole, 4-cyano-1,2,3-triazole, 5-cyano-1,2,3-triazole, 4-nitro-1,2,3-triazole, 5-nitro-1,2,3-triazole, methyl 1,2,3-triazole-4-carboxylate, methyl 1,2,3-triazole-5-carboxylate, ethyl 1,2,3-triazole-4-carboxylate, ethyl 1,2,3-triazole-5-carboxylate, 4-trifluoromethyl-1,2,3-triazole, 5-trifluoromethyl-1,2,3-triazole, 4-methyl-N-methyl-1,2,3-triazole, 5-methyl-N-methyl-1,2,3-triazole, 4-chloro-N-methyl-1,2,3-triazole, 5-chloro-N-methyl-1,2,3-triazole, 4-fluoro-N-methyl-1,2,3-triazole, 5-fluoro-N-methyl-1,2,3-triazole, 4-cyano-N-methyl-1,2,3-triazole, 5-cyano-N-methyl-1,2,3-triazole, 4-nitro-N-methyl-1,2,3-triazole, 5-nitro-N-methyl-1,2,3-triazole, methyl N-methyl-1,2,3-triazole-4-carboxylate, methyl N-methyl-1,2,3-triazole-5-carboxylate, ethyl N-methyl-1,2,3-triazole-4-carboxylate, ethyl N-methyl-1,2,3-triazole-5-carboxylate, 4-trifluoromethyl-N-methyl-1,2,3-triazole, and 5-trifluoromethyl-N-methyl-1,2,3-triazole; tetrazole and substituted tetrazoles, such as N-methyltetrazole, 5-methyl-tetrazole, 5-methyl-N-methyl-tetrazole, 5-chloro-tetrazole, 5-chloro-N-methyl-tetrazole, 5-fluoro-tetrazole, 5-fluoro-N-methyl-tetrazole, 5-nitro-tetrazole, 5-nitro-N-methyl-tetrazole, 5-cyano-tetrazole, 5-cyano-N-methyl-tetrazole, 5-trifluoromethyl-tetrazole, 5-trifluoromethyl-N-methyl-tetrazole, methyl 1H-1,2,3,4-tetrazole-5-carboxylate, ethyl 1H-1,2,3,4-tetrazole-5-carboxylate, methyl 1-methyl-1,2,3,4-tetrazole-5-carboxylate, ethyl 1-methyl-1,2,3,4-tetrazole-5-carboxylate, tetrazole-5-carboxaldehyde, 1H-tetrazole-5-carboxaldehyde, 1-methyl-1-(1-methyl-1H-1,2,3,4-tetrazol-5-yl)ethan-1-one, 1-(1H-1,2,3,4-tetrazol-5-yl)ethan-1-one; benzothiazole and substituted benzothiazoles, such as 2-methyl-benzothiazole, 4-methyl-benzothiazole, 5-methyl-benzothiazole, 6-methyl-benzothiazole, 7-methyl-benzothiazole, 2-fluoro-benzothiazole, 4-fluoro-benzothiazole, 5-fluoro-benzothiazole, 6-fluoro-benzothiazole, 7-fluoro-benzothiazole, 2-chloro-benzothiazole, 4-chloro-benzothiazole, 5-chloro-benzothiazole, 6-chloro-benzothiazole, 7-chloro-benzothiazole, 2-cyano-benzothiazole, 4-cyano-benzothiazole, 5-cyano-benzothiazole, 6-cyano-benzothiazole, 7-cyano-benzothiazole, 2-nitro-benzothiazole, 4-nitro-benzothiazole, 5-nitro-benzothiazole, 6-nitro-benzothiazole, 7-nitro-benzothiazole, 2-trifluoromethyl-benzothiazole, 4-trifluoromethyl-benzothiazole, 5-trifluoromethyl-benzothiazole, 6-trifluoromethyl-benzothiazole, 7-trifluoromethyl-benzothiazole, 2-benzothiazolecarboxylic acid methyl ester, 4-benzothiazolecarboxylic acid methyl ester, 5-benzothiazolecarboxylic acid methyl ester, 6-benzothiazolecarboxylic acid methyl ester, 7-benzothiazolecarboxylic acid methyl ester, 2-benzothiazolecarboxylic acid ethyl ester, 4-benzothiazolecarboxylic acid ethyl ester, 5-benzothiazolecarboxylic acid ethyl ester, 6-benzothiazolecarboxylic acid ethyl ester, 7-benzothiazolecarboxylic acid ethyl ester, benzothiazole-2-carbaldehyde, benzothiazole-4-carbaldehyde, benzothiazole-5-carbaldehyde, benzothiazole-6-carbaldehyde, benzothiazole-7-carbaldehyde, 2-acetylbenzothiazole, 4-acetylbenzothiazole, 5-Acetylbenzothiazole, 6-acetylbenzothiazole, and 7-acetylbenzothiazole, 3,4-dihydronaphthalen-1(2H)-one, 8-methyl-3,4-dihydronaphthalen-1(2H)-one, 7-methyl-3,4-dihydronaphthalen-[(2H)-one, 6-methyl-3,4-dihydronaphthalen-1(2H)-one, 5-methyl-3,4-dihydronaphthalen-1(2H)-one, 2,3-dihydro-1H-inden-1-one, 7-methyl-2,3-dihydro-1H-inden-1-one, 6-methyl-2,3-dihydro-1H-inden-1-one, 57-methyl-2,3-dihydro-1H-inden-1-one, 4-methyl-2,3-dihydro-1H-inden-1-one and mixtures thereof.

Suitable aprotic polar solvents are acetonitrile, formamide, dimethylformamide (DMF), dimethylacetamide, dimethylsulfoxide (DMSO), N-methylpyrrolidone, $(CH_3)_2SO$, dimethyl sulfone, sulfolane, cyclic ureas, such as 1,3-dimethyl-3,4,5,6-tetrahydro-2(1H)-pyrimidinone (DMPU), imidazolidin-2-one and mixtures thereof.

In a special embodiment, the composition according to the invention contains a viscosity-modifying additive. Suitable viscosity-modifying additives are dielectric polymers or semiconductive polymers. Suitable dielectric polymers are e.g. polystyrene, polyimides, fluorinated polyimides, polyarylene ether, polyvinylidene fluoride, polytetrafluoroethylene, poly-2-vinyl-naphthalene (P2VN), etc. A preferred viscosity-modifying additive is polystyrene. Preferably, the viscosity-modifying additive has a solubility in component B) at 20° C. of at least 0.01 mg/ml, preferably of at least 0.05 mg/ml. Preferably, the composition according to the invention contains the viscosity-modifying additive in an amount of 0.1 to 30 wt.-%, preferably 0.2 to 20 wt.-%, based on the total weight of component B) and the viscosity-modifying additive.

The composition according to the invention allows the preparation of various articles, structures, or devices from semiconductors A) by solution-processing. As used herein, "solution-processing" refers to various solution-phase processes including spin-coating, printing (e.g., inkjet printing, screen printing, pad printing, offset printing, gravure printing, flexographic printing, lithographic printing, mass-printing and the like), spray coating, electrospray coating, drop casting, dip coating, slot coating and blade coating.

Articles that can be advantageously prepared from the composition according to the invention are electronic devices, optical devices and optoelectronic devices. Those include organic field effect transistors (OFETs) (e.g., organic thin film transistors (OTFTs)), organic photovoltaic devices (OPVs), photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, sensors and ring oscillators. All of those articles may contain a semiconductor component A) that is deposited from a composition according to the invention.

A further object of the invention is a process for the preparation of an electronic device, optical device or optoelectronic device, comprising:
(a) providing a composition comprising A) at least one organic semiconductor and B) at least one compound that is liquid at 20° C. and 1013 mbar, as defined in any of claims 1 to 15,
(b) applying the composition provided in step (a) to at least a portion of the surface of a substrate to allow deposition of the at least one organic semiconductor on the substrate.

The depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, slot-coating, dip coating, blade coating, or spraying.

Preferably, in step (b) the application of the composition provided in step (a) to at least a portion of the surface of the substrate is performed by printing.

A wide variety of substrates may be used in the method of the present invention. The substrates may be made of virtually any materials which are stable under the process conditions of the method of the invention. Thus, the substrate may include organic and inorganic materials or composite materials. Suitable substrates are in principle all materials known for this purpose. Suitable substrates comprise, for example, oxidic materials, metals, semiconductors, metal alloys, semiconductor alloys, polymers, inorganic solids, paper and combinations thereof.

Suitable substrates are preferably selected from $SiO_2$, inorganic glasses, quartz, ceramics, undoped or doped inorganic semiconductors, metals of groups 8, 9, 10 or 11 of the Periodic Table and metal alloys thereof, polymeric materials, filled polymeric materials and combinations thereof.

Preferred metal and metal alloy substrates comprise Au, Ag, Cu, etc. Preferred undoped or doped inorganic semiconductors are Si, doped Si, Ge and doped Ge. Preferred polymeric materials are selected from acrylics, epoxies, polyamides, polycarbonates, polyimides, polyvinyl chloride, polyolefins, polystyrene homopolymers and copolymers, polyketones, poly(oxy-1,4-phenyleneoxy-1,4-phenylenecarbonyl-1,4-phenylene (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), fluoropolymers, polyurethanes, fiber-reinforced plastics (FRP) and combinations thereof.

Especially preferred substrates are selected from Si, $SiO_2$, glass, quartz, ceramics and combinations thereof. The substrate may be flexible or inflexible, and have a curved or planar geometry, depending on the desired use.

In a special embodiment, at least the surface of the substrate comprises or consists of at least one dielectric. Suitable dielectrics are selected from inorganic dielectric materials, polymeric dielectric materials and combinations thereof. Suitable inorganic dielectric materials are $SiO_2$, $Al_2O_3$, $ZrO_2$, $HfO_2$, $TaO5$, $WO_3SiO_3N_4$, RbBr, LiF, $BaTiO_3$, $PbTiO_3$, and mixtures thereof. Suitable polymeric dielectric materials are polystyrene, poly-α-methylstyrene, polyolefins (such as polypropylene, polyethylene, polyisobutene), polyvinylcarbazole, fluorinated polymers (e.g. Cytop, CYMM), cyanopullulans, polyvinylphenol, poly-p-xylene, polyvinyl chloride, poly(methyl methacrylate)/trimethylolpropane triacrylate copolymers etc., and combinations thereof. Specific dielectrics are "self-assembled nanodielectrics", i.e. polymers which are obtained from monomers comprising SiCl functionalities, for example $Cl_3SiOSiCl_3$, $Cl_3Si-(CH_2)_6-SiCl_3$, $Cl_3Si-(CH_2)_{12}-SiCl_3$, and/or which are crosslinked by atmospheric moisture or by addition of water diluted with solvents (see, for example, Facchetti Adv. Mat. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facchetti, US patent application 2006/0202195).

The surface of the substrate and/or the dielectric can be subjected to a modification prior to the deposition of component A).

In a special embodiment, the surface of the substrate and/or the dielectric is subjected to a modification prior to the deposition of compound A) resulting in a self-assembled monolayer (SAM) of the compounds employed for the modification.

In a further modification only parts of the substrate are covered with the self-assembled monolayer (SAM). Without being bound by a theory this might be advantageous to achieve a lateral structuring of the morphology of the compound A).

The modification of the surface of the substrate and/or the dielectric prior to the deposition of compound A) may e.g. serve to form regions which bind the semiconductor materials and/or regions on which no semiconductor materials can be deposited. Further, the modification of the surface of the substrate and/or the dielectric may have an influence on the properties of the obtained semiconductor, e.g. its charge transport mobility, on/off ratio, etc.

Suitable compounds for the surface modification are:
silanes, such as alkyltrichlorosilanes, e.g. n-octadecyltrichlorosilane (OTS); compounds with trialkoxysilane groups, e.g. alkyltrialkoxysilanes, such as n-octadecyltrimethoxysilane, n-octadecyltriethoxysilane, n-octadecyltri(n-propyl)oxysilane, n-octadecyltri(isopropyl)oxysilane; trialkoxyaminoalkylsilanes, such as triethoxyaminopropylsilane and N[(3-triethoxysilyl)

propyl]ethylenediamine; trialkoxyalkyl 3-glycidyl ether silanes, such as triethoxypropyl 3-glycidyl ether silane; trialkoxyallylsilanes, such as allyltrimethoxysilane; trialkoxy(isocyanatoalkyl)silanes; trialkoxysilyl (meth)acryloyloxyalkanes and trialkoxysilyl(meth) acrylamidoalkanes, such as 1-triethoxysilyl-3-acryloyl-oxypropane, phosphonic acids, e.g. 4-ethoxyphenylphosphonic acid,
carboxylic acids,
hydroxamic acids,
amines,
phosphines,
sulfur-comprising compounds, especially thiols, and mixtures thereof.

The compounds for the surface modification are preferably selected from alkyltrichlorosilanes, alkyltrialkoxysilanes, hexaalkyldisilazanes, $C_8$-$C_{30}$-alkylthiols, mercaptocarboxylic acids, mercaptosulfonic acids and mixtures thereof.

In a special embodiment, the compounds for the surface modification are selected from n-octadecyltrichlorosilane (OTS), n-octadecyltrimethoxysilane, n-octadecyltriethoxysilane, hexamethyldisilazane (HMDS), 4-ethoxyphenylphosphonic acid, hexadecanethiol, mercaptoacetic acid, 3-mercaptopropionic acid, mercaptosuccinic acid and 3-mercapto-1-propanesulfonic acid, the alkali metal and ammonium salts of mercaptoacetic acid, 3-mercaptopropionic acid, mercaptosuccinic acid and 3-mercapto-1-propanesulfonic acid and mixtures thereof.

In order to modify the surface of the substrate with a plethora of functional groups it can be activated with acids or bases. Further, the surface of the substrate can be activated by oxidation, irradiation with electron beams or by plasma treatment. Further, the afore-mentioned substances comprising functional groups can be applied to the surface of the substrate, e.g. via deposition from solution, physical vapor deposition (PVD) or chemical vapor deposition (CVD).

The composition according to the invention is advantageously suitable for the fabrication of organic field-effect transistors. They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. OFETs prepared from the composition according to the invention are especially suitable for use in displays (specifically large-surface area and/or flexible displays), RFID tags, smart labels and sensors.

An aspect of the present teaching relates to the fabrication of an organic field-effect transistor that incorporates a semiconductor component prepared from a composition according to the invention. An OFETs generally comprises a substrate having at least one gate structure including a gate electrode and a gate dielectric, a source electrode and a drain electrode and a semiconductor material that is in contact with the source and drain electrode and the gate dielectric.

A specific embodiment is a substrate with a pattern (topography) of organic field-effect transistors, each transistor comprising
an organic semiconductor disposed on the substrate;
a gate structure for controlling the conductivity of the conductive channel; and
conductive source and drain electrodes at the two ends of the channel.

As a buffer layer, any dielectric material is suitable, for example anorganic materials such LIF, $AlO_x$, $SiO_2$ or silicium nitride or organic materials such as polyimides or polyacrylates, e.g. polymethylmethacrylate (PMMA).

A further specific embodiment is a substrate having a pattern of organic field-effect transistors, each transistor forming an integrated circuit or being part of an integrated circuit and at least some of the transistors are prepared by deposition of an organic semiconductor from a composition according to the invention.

Suitable substrates are those mentioned above. A typical substrate for semiconductor units comprises a matrix (for example a silicon, quartz or polymer matrix) and, optionally, a dielectric top layer. Suitable dielectrics are those mentioned above, wherein $SiO_2$ is especially preferred.

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators, such as $SiO_2$, silicon nitride ($Si_3N_4$), etc., ferroelectric insulators, such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 6, 7, 8, 9, 10 or 11 of the Periodic Table, such as Pd, Au, Ag, Cu, Al, Ni, Cr, etc. Also suitable are conductive polymers, such as PEDOT (=poly (3,4-ethylenedioxythiophene)):PSS (=poly(styrenesulfonate)), polyaniline, surface-modified gold, etc. Preferred electrically conductive materials have a specific resistance of less than $10^{-3}$ ohm×meter, preferably less than $10^{-4}$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation or sputtering, lithographic processes or another structuring process, such as printing techniques.

The resulting semiconductor layers generally have a thickness which is sufficient for forming a semiconductor channel which is in contact with the source/drain electrodes.

The semiconductor component is preferably deposited on the substrate in a thickness of from 0.5 to 1000 nm, more preferably from 1.5 to 250 nm.

In a preferred embodiment, the inventive field-effect transistor is a thin-film transistor (TFT). In a customary construction, a thin-film transistor has a gate electrode disposed on the substrate or buffer layer (the buffer layer being part of the substrate), a gate insulation layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula A) is subjected to a modification as mentioned above.

Various semiconductor architectures are conceivable from the composition according to the invention, for example top contact, top gate, bottom contact, bottom gate, or else a vertical construction, for example a VOFET (vertical organic field-effect transistor), as described, for example, in US 2004/0046182.

Preferred semiconductor architectures are the following:
1. substrate, dielectric, organic semiconductor, preferably gate, dielectric, organic semiconductor, source and drain, known as "Bottom Gate Top Contact";
2. substrate, dielectric, organic semiconductor, preferably substrate, gate, dielectric, source and drain, organic semiconductor, known as "Bottom Gate Bottom Contact";
3. substrate, organic semiconductor, dielectric, preferably substrate, source and drain, organic semiconductor, dielectric, gate, known as "Top Gate Bottom Contact";
4. substrate, organic semiconductor, dielectric, preferably substrate, organic semiconductor, source and drain, dielectric, gate, known as "Top Gate Top Contact".

The layer thicknesses are, for example, from 0.5 nm to 5 µm in semiconductors, from 3 nm to 10 µm in the dielectric; the electrodes may, for example, be from 20 nm to 10 µm. The OFETs may also be combined to form other components, such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors, such as polarization-sensitive photodetectors, gates, AND, NAND, NOT, OR, TOR and NOR gates, registers, switches, timer units, static or dynamic stores and other dynamic or sequential, logical or other digital components including programmable switches.

A specific semiconductor element is an inverter. In digital logic, the inverter is a gate which inverts an input signal. The inverter is also referred to as a NOT gate. Real inverter switches have an output current which constitutes the opposite of the input current. Typical values are, for example, (0, +5V) for TTL switches. The performance of a digital inverter reproduces the voltage transfer curve (VTC), i.e. the plot of input current against output current. Ideally, it is a staged function and, the closer the real measured curve approximates to such a stage, the better the inverter is.

The composition according to the invention is also particularly suitable for use in organic photovoltaics (OPVs). An aspect of the present teaching relates to the fabrication of organic solar cells, e.g. solar cells which are characterized by diffusion of excited states (exciton diffusion). In this case, one or both of the semiconductor materials utilized is notable for a diffusion of excited states (exciton mobility). Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

A representative organic solar cell comprises a substrate with at least one cathode and at least one anode and at least one photoactive region comprising a semiconductor material. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction.

Suitable substrates for organic solar cells are those mentioned above, for example, oxidic materials, polymers and combinations thereof. Preferred oxidic materials are selected from glass, ceramic, $SiO_2$, quartz, etc. Preferred polymers are selected from polyethylene terephthalates, polyolefins (such as polyethylene and polypropylene), polyesters, fluoropolymers, polyamides, polyurethanes, polyalkyl (meth) acrylates, polystyrenes, polyvinyl chlorides and mixtures and composites.

Suitable electrodes (cathode, anode) are in principle metals, semiconductors, metal alloys, semiconductor alloys, nanowire thereof and combinations thereof. Preferred metals are those of groups 2, 8, 9, 10, 11 or 13 of the periodic table, e.g. Pt, Au, Ag, Cu, Al, In, Mg or Ca. Preferred semiconductors are, for example, doped Si, doped Ge, indium tin oxide (ITO), fluorinated tin oxide (FTO), gallium indium tin oxide (GITO), zinc indium tin oxide (ZITO), poly(3,4-ethylenedioxythiophene) poly(styrenesulfonate) (PEDOT-PSS), etc. Preferred metal alloys are, for example, alloys based on Pt, Au, Ag, Cu, etc. A specific embodiment is Mg/Ag alloys.

The material used for the electrode facing the light (the anode in a normal structure, the cathode in an inverse structure) is preferably a material at least partly transparent to the incident light. This preferably includes electrodes which have glass and/or a transparent polymer as a carrier material. Transparent polymers suitable as carriers are those mentioned above, such as polyethylene terephthalate. The electrical contact connection is generally effected by means of metal layers and/or transparent conductive oxides (TCOs). These preferably include ITO, doped ITO, FTO (fluorine doped tin oxide), AZO (aluminum doped tin oxide), ZnO, $TiO_2$, Ag, Au, Pt or graphene or multi layer graphene or carbon nanotubes. Particular preference is given to ITO for contact connection. For electrical contact connection, it is also possible to use a conductive polymer, for example a poly-3,4-alkylenedioxythiophene, e.g. poly-3,4-ethyleneoxythiophene poly(styrenesulfonate) (PEDOT).

The electrode facing the light is configured such that it is sufficiently thin to bring about only minimal light absorption but thick enough to enable good charge transport of the extracted charge carriers. The thickness of the electrode layer (without carrier material) is preferably within a range from 20 to 200 nm.

In a specific embodiment, the material used for the electrode facing away from the light (the cathode in a normal structure, the anode in an inverse structure) is a material which at least partly reflects the incident light. This includes metal films, preferably of Ag, Au, Al, Ca, Mg, In, and mixtures thereof. Preferred mixtures are Mg/Al. The thickness of the electrode layer is preferably within a range from 20 to 300 nm.

The photoactive region comprises or consists of at least one layer which comprises an organic semiconductor A). In addition to the photoactive layer there may be one or more further layer(s). These are, for example, selected from
  layers with electron-conducting properties (electron transport layer, ETL),
  layers which comprise a hole-conducting material (hole transport layer, HTL), which need not absorb any radiation, exciton- and hole-blocking layers (e.g. EBLs), which must not absorb, and multiplication layers.

Suitable materials for these layers are described in detail hereinafter.

Suitable exciton- and hole-blocking layers are described, for example, in U.S. Pat. No. 6,451,415. Suitable materials for exciton-blocking layers are, for example, bathocuproin (BCP), 4,4',4"-tris[3-methylphenyl-N-phenylamino]triphenylamine (m-MTDATA).

The solar cells preferably comprise at least one photoactive donor-acceptor heterojunction. Optical excitation of an organic material generates excitons. In order that a photocurrent occurs, the electron-hole pair has to be separated, typically at a donor-acceptor interface between two unlike contact materials. At such an interface, the donor material forms a heterojunction with an acceptor material. When the charges are not separated, they can recombine in a process also known as "quenching", either radiatively by the emission of light of a lower energy than the incident light or nonradiatively by generation of heat. Both processes are undesired.

If at least one compound of the general formula (I) is used as an n-semiconductor (electron conductor, acceptor) it is employed as the ETM (electron transport material) of the solar cell. It can then be combined with an appropriate p-semiconductor (electron donor material) that is employed as the HTM (hole transport material) of the solar cell. Hole-conducting materials preferably comprise at least one material with high ionization energy. The materials may be organic or inorganic materials.

Suitable HTMs are, for example,

N,N'-Bis(naphthalen-1-yl)-N,N'-bis(phenyl)-9,9-dimethylfluoren,

N,N'-Bis(3-methylphenyl)-N,N'-bis(phenyl)-9,9-diphenylfluoren,

N,N'-Bis(naphthalen-1-yl)-N,N'-bis(phenyl)-9,9-diphenylfluoren,

N,N'-Bis(naphthalen-1-yl)-N,N'-bis(phenyl)-2,2-dimethylbenzidin,

N,N'-Bis(3-methylphenyl)-N,N'-bis(phenyl)-9,9-spirobifluoren, 2,2',7,7'-Tetrakis(N,N-diphenylamino)-9,9'-spirobifluoren, N,N'-Bis(naphthalen-1-yl)-N,N'-bis(phenyl)-benzidin, N,N'-Bis(naphthalen-2-yl)-N,N'-bis(phenyl)-benzidin, N,N'-Bis(3-methylphenyl)-N,N'-bis(phenyl)-benzidin, N,N'-Bis(3-methylphenyl)-N,N'-bis(phenyl)-9,9-dimethylfluoren, N,N'-Bis(naphthalen-1-yl)-N,N'-bis(phenyl)-9,9-spirobifluoren, Di[4-(N,N-ditolyl-amino)-phenyl]cyclohexan, 2,2',7,7'-tetra(N,N-di-tolyl)amino-spirobifluoren, 9,9-Bis[4-(N,N-bis-biphenyl-4-yl-amino)phenyl]-9H-fluoren, 2,2',7,7'-Tetrakis[N-naphthalenyl(phenyl)-amino]-9,9-spirobifluoren, 2,7-Bis[N,N-bis(9,9-spiro-bifluorene-2-yl)-amino]-9,9-spirobifluoren, 2,2'-Bis[N,N-bis(biphenyl-4-yl)amino]-9,9-spirobifluoren, N,N'-bis(phenanthren-9-yl)-N,N'-bis(phenyl)-benzidin, N,N,N',N'-tetra-naphthalen-2-yl-benzidin, 2,2'-Bis(N,N-di-phenyl-amino)-9,9-spirobifluoren, 9,9-Bis[4-(N,N-bis-naphthalen-2-yl-amino)phenyl]-9H-fluoren, 9,9-Bis[4-(N,N'-bis-naphthalen-2-yl-N,N'-bis-phenyl-amino)phenyl]-9H-fluoren, Titanium oxide phthalocyanin, Copper phthalocyanin, 2,3,5,6-Tetrafluoro-7,7,8,8-tetracyano-quinodimethan, 4,4',4"-Tris(N-3-methylphenyl-N-phenyl-amino)triphenylamin, 4,4',4"-Tris(N-(2-naphthyl)-N-phenyl-amino)triphenylamin, 4,4',4"-Tris(N-(1-naphthyl)-N-phenyl-amino)triphenylamin, 4,4',4"-Tris(N,N-diphenyl-amino)triphenylamin, Pyrazino[2,3-f][1,10]phenanthroline-2,3-dicarbonitril N,N,N',N'-Tetrakis(4-methoxyphenyl)benzidin, 2,7-Bis[N,N-bis(4-methoxy-phenyl)amino]-9,9-spirobifluoren, 2,2'-Bis[N,N-bis(4-methoxy-phenyl)amino]-9,9-spirobifluoren, N,N'-di(naphthalen-2-yl)-N,N'-diphenylbenzene-1,4-diamin, N,N'-di-phenyl-N,N'-di-[4-(N,N-di-tolyl-amino)phenyl]benzidin, N,N'-di-phenyl-N,N'-di-[4-(N,N-di-phenyl-amino)phenyl]benzidin.

Examples of polymeric hole transport materials, are PEDOT (poly (3,4-ethylenedioxythiophene), polyvinylcarbazole (PVK), poly(N,N'-bis (4-butylphenyl)-N,N'-bis(phenyl) benzidine (PTPD), polyaniline (PANI) and poly (3-hexylthiophene (P3HT).

In a first embodiment, the heterojunction has a flat configuration (see: Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).).

In a second preferred embodiment, the heterojunction is configured as a bulk (mixed) heterojunction, also referred to as an interpenetrating donor-acceptor network. Organic photovoltaic cells with a bulk heterojunction are described, for example, by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005). Bulk heterojunctions are discussed in detail hereinafter.

The composition according to the invention can be used for the fabrication of the photoactive material in cells with MiM, pin, pn, Mip or Min structure (M=metal, p=p-doped organic or inorganic semiconductor, n=n-doped organic or inorganic semiconductor, i=intrinsically conductive system of organic layers; see, for example, J. Drechsel et al., Org. Electron., 5 (4), 175 (2004) or Maennig et al., Appl. Phys. A 79, 1-14 (2004)).

The composition according to the invention can also be used for the fabrication of the photoactive material in tandem cells. Suitable tandem cells are described, for example, by P. Peumans, A. Yakimov, S. R. Forrest in J. Appl. Phys., 93 (7), 3693-3723 (2003) (see also U.S. Pat. Nos. 4,461,922, 6,198,091 and 6,198,092) and are described in detail hereinafter.

The composition according to the invention can also be used for the fabrication of the photoactive material in tandem cells which are constructed from two or more than two stacked MiM, pin, Mip or Min structures (see DE 103 13 232.5 and J. Drechsel et al., Thin Solid Films, 451452, 515-517 (2004)).

The layer thickness of the M, n, i and p layers is typically within a range from 10 to 1000 nm, more preferably from 10 to 400 nm. The other layers which form the solar cell can be produced by customary processes known to those skilled in the art. These include vapor deposition under reduced pressure or in an inert gas atmosphere, laser-ablation or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by solution processing.

In a suitable embodiment, the solar cells are present as an individual cell with flat heterojunction and normal structure. In a specific embodiment, the cell has the following structure:
- an at least partly transparent conductive layer (top electrode, anode) (11)
- a hole-conducting layer (12)
- a layer which comprises a donor material (13)
- a layer which comprises an acceptor material (14)
- an exciton-blocking and/or electron-conducting layer (15)
- a second conductive layer (back electrode, cathode) (16)

The essentially transparent conductive layer (11) (anode) comprises a carrier, such as glass or a polymer (e.g. polyethylene terephthalate) and a conductive material, as described above. Examples include ITO, doped ITO, FTO, ZnO, AZO, etc. The anode material can be subjected to a surface treatment, for example with UV light, ozone, oxygen plasma, $Br_2$, etc. The layer (11) should be sufficiently thin to enable maximum light absorption, but also sufficiently thick to ensure good charge transport. The layer thickness of the transparent conductive layer (11) is preferably within a range from 20 to 200 nm.

Solar cells with normal structure optionally have a hole-conducting layer (=layer 12). This layer comprises at least one hole-conducting material (hole transport material, HTM). Hole-conducting materials (HTM) suitable for forming layers with hole-conducting properties (HTL) preferably comprise at least one material with high ionization energy. The ionization energy is preferably at least 5.0 eV, more preferably at least 5.5 eV. The materials may be organic or inorganic materials. Organic materials suitable for use in a layer with hole-conducting properties are preferably selected from poly(3,4-ethylenedioxythiophene) poly(styrenesulfonate) (PEDOT-PSS), Ir-DPBIC (tris-N,N'-diphenyl-benzimidazol-2-ylideneiridium(III)), N,N'-diphenyl-N,N'-bis(3-methylphenyl)-1,1'-diphenyl-4,4'-diamine (α-NPD), 2,2',7,7'-tetrakis(N,N-di-p-methoxyphenylamine)-9,9'-spirobifluorene (spiro-MeOTAD), etc. and mixtures thereof.

The organic materials may, if desired, be doped with a p-dopant which has a LUMO within the same range as or lower than the HOMO of the hole-conducting material. Suitable dopants are, for example, 2,3,5,6-tetrafluoro-7,7,8,8-tetracyanoquino-dimethane ($F_4TCNQ$), $WO_3$, $MoO_3$, etc. Inorganic materials suitable for use in a layer with hole-conducting properties are preferably selected from $WO_3$, $MoO_3$, etc.

If present, the thickness of the layers with hole-conducting properties is preferably within a range from 5 to 200 nm, more preferably 10 to 100 nm.

Layer (13) comprises at least one donor material. The thickness of the layer should be sufficient to absorb a maximum amount of light, but thin enough to enable effective dissipation of the charge. The thickness of the layer (13) is preferably within a range from 5 nm to 1 µm, more preferably from 5 to 100 nm.

Layer (14) comprises at least acceptor material. The thickness of the layer should be sufficient to absorb a maximum amount of light, but thin enough to enable effective dissipation of the charge. The thickness of the layer (14) is preferably within a range from 5 nm to 1 µm, more preferably from 5 to 80 nm.

Suitable donor and acceptor materials are in principle organic semiconductors, wherein at least one is a semiconductor A) deposited fro a composition according to the invention.

Solar cells with normal structure optionally comprise an exciton-blocking and/or electron-conducting layer (15) (EBL/ETL). Suitable materials for exciton-blocking layers generally have a greater band gap than the materials of layer (13) and/or (14). They are firstly capable of reflecting excitons and secondly enable good electron transport through the layer. The materials for the layer (15) may comprise organic or inorganic materials. Suitable organic materials are preferably selected from 2,9-dimethyl-4,7-diphenyl-1,10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc.

Inorganic materials suitable for use in a layer with electron-conducting properties are preferably selected from ZnO, etc. If present, the thickness of the layer (15) is preferably within a range from 5 to 500 nm, more preferably 10 to 100 nm.

Layer 16 is the cathode and preferably comprises at least one compound with low work function, more preferably a metal, such as Ag, Al, Mg, Ca, etc. The thickness of the layer (16) is preferably within a range from about 10 nm to 10 µm, e.g. 10 nm to 60 nm.

In a further suitable embodiment, the inventive solar cells are present as an individual cell with a flat heterojunction and inverse structure.

In a specific embodiment, the cell has the following structure:
- an at least partly transparent conductive layer (cathode) (11)
- an exciton-blocking and/or electron-conducting layer (12)
- a layer which comprises an acceptor material (13)
- a layer which comprises a donor material (14)
- a hole-conducting layer (15)
- a second conductive layer (back electrode, anode) (16)

With regard to suitable and preferred materials for the layers (11) to (16), reference is made to the above remarks regarding the corresponding layers in solar cells with normal structure.

In a suitable embodiment, the inventive solar cell is a tandem cell.

A tandem cell consists of two or more than two (e.g. 3, 4, 5, etc.) subcells. A single subcell, some of the subcells or all subcells may have photoactive donor-acceptor heterojunctions. Each donor-acceptor heterojunction may be in the form of a flat heterojunction or in the form of a bulk heterojunction. According to the invention, the photoactive layer of at least one subcell is prepared from a composition according to the invention. The subcells which form the tandem cell may be connected in parallel or in series. The subcells which form the tandem cell are preferably connected in series. There is preferably an additional recombination layer in each case between the individual subcells. The individual subcells have the same polarity, i.e. generally either only cells with normal structure or only cells with inverse structure are combined with one another.

"Subcell" refers here to a cell as defined above without cathode and anode. The subcells may, for example, either all have polymorph 2 in the photoactive layer or have other combinations of semiconductor materials, for example C60 with zinc phthalocyanine, C60 with oligothiophene (such as DCVST). In addition, individual subcells may also be configured as dye-sensitized solar cells or polymer cells.

In addition to the compounds of the general formula (I.a) and (I.b) the following semiconductor materials are suitable for use in organic photovoltaics:

Acenes, such as anthracene, tetracene, pentacene and substituted acenes. Substituted acenes comprise at least one substituent selected from electron-donating substituents (e.g. alkyl, alkoxy, ester, carboxylate or thioalkoxy), electron-withdrawing substituents (e.g. halogen, nitro or cyano) and combinations thereof. These include 2,9-dialkylpentacenes and 2,10-dialkylpentacenes, 2,10-dialkoxypentacenes, 1,4,8,11-tetraalkoxypentacenes and rubrene (5,6,11,12-tetraphenylnaphthacene). Suitable substituted pentacenes are described in US 2003/0100779 and U.S. Pat. No. 6,864,396. A preferred acene is rubrene (5,6,11,12-tetraphenylnaphthacene).

Phthalocyanines, such as hexadecachlorophthalocyanines and hexadecafluorophthalocyanines, metal-free phthalocyanine and phthalocyanine comprising divalent metals, especially those of titanyloxy, vanadyloxy, iron, copper, zinc, especially copper phthalocyanine, zinc phthalocyanine and metal-free phthalocyanine, copper hexadecachlorophthalocyanine, zinc hexadecachlorophthalocyanine, metal-free hexadecachlorophthalocyanine, copper hexadecafluorophthalocyanine, hexadecafluorophthalocyanine or metal-free hexadecafluorophthalocyanine.

Porphyrins, for example 5,10,15,20-tetra(3-pyridyl)porphyrin (TpyP).

Liquid-crystalline (LC) materials, for example hexabenzocoronene (HBC-PhC12) or other coronenes, coronenediimides, or triphenylenes, such as 2,3,6,7,10,11-hexahexylthiotriphenylene (HTT6) or 2,3,6,7,10,11-hexakis(4-n-nonylphenyl)triphenylene (PTP9), 2,3,6,7,10,11-hexakis(undecyloxy)triphenylene (HATI11). Particular preference is given to LCs which are discotic.

Thiophenes, oligothiophenes and substituted derivatives thereof. Suitable oligothiophenes are quaterthiophenes, quinquethiophenes, sexithiophenes, α,ω-di($C_1$-$C_8$)alkyloligothiophenes such as α,ω-dihexylquaterthiophenes, α,ω-dihexylquinquethiophenes and α,ω-dihexylsexithiophenes, poly(alkylthiophenes) such as poly(3-hexylthiophene, bis(dithienothiophenes), anthradithiophenes and dialkylanthradithiophenes such as dihexylanthradithiophene, phenylenethiophene (P-T) oligomers and derivatives thereof, especially α,ω-alkyl-substituted phenylene-thiophene oligomers.

Preferred thiophenes, oligothiophenes and substituted derivatives thereof, are poly-3-hexylthiophene (P3HT) or compounds of the αα'-bis(2,2-dicyanovinyl)quin-quethiophene (DCVST) type, poly(3-(4-octylphenyl)-2,2'-bithiophene) (PTOPT), poly(3-(4'-(1'',4'',7''-trioxaoctyl)phenyl) thiophene) (PEOPT), poly(3-(2'-methoxy-5'-octylphenyl) thiophenes) (POMeOPTs), poly(3-octylthiophene) (P3OT), pyridine-containing polymers such as poly(pyridopyrazine vinylene), poly(pyridopyrazine vinylene) modified with alkyl groups e.g. EHH-PpyPz, PTPTB copolymers, polybenzimidazobenzophenanthroline (BBL), poly(9,9-dioctylfluorene-co-bis-N,N'-(4-methoxyphenyl)-bis-N,N'-phenyl-1,4-phenylenediamine) (PFMO); see Brabec C., Adv. Mater., 2996, 18, 2884. (PCPDTBT) poly[2,6-(4,4-bis(2-ethylhexyl)-4H-cyclopenta[2,1-b; 3,4-b']-dithiophene)-4,7-(2,1,3-benzothiadiazoles)].

Paraphenylenevinylene and paraphenylenevinylene-comprising oligomers and polymers, for example polyparaphenylenevinylene (PPV), MEH-PPV (poly(2-methoxy-5-(2'-ethylhexyloxy)-1,4-phenylenevinylene)), MDMO-PPV (poly(2-methoxy-5-(3',7'-dimethyloctyloxy)-1,4-phenylenevinylene)), cyano-paraphenylenevinylene (CN-PPV), CN-PPV modified with alkoxy groups.

PPE-PPV hybrid polymers (phenylene-ethynylene/phenylene-vinylene hybrid polymers).

Polyfluorenes and alternating polyfluorene copolymers, for example with 4,7-dithien-2'-yl-2,1,3-benzothiadiazoles, and also poly(9,9'-dioctylfluorene-co-benzothiadiazole) ($F_8BT$), poly(9,9'-dioctylfluorene-co-bis-N,N'-(4-butylphenyl)-bis-N,N'-phenyl-1,4-phenylenediamine) (PFB).

Polycarbazoles, i.e. carbazole-comprising oligomers and polymers, such as (2,7) and (3,6).

Polyanilines, i.e. aniline-comprising oligomers and polymers.

Triarylamines, polytriarylamines, polycyclopentadienes, polypyrroles, polyfuran, polysilols, polyphospholes, N,N'-Bis-(3-methylphenyl)-N,N'-bis-(phenyl)benzidine (TPD), 4,4'-bis(carbazol-9-yl) biphenyl (CBP), 2,2',7,7'-tetrakis-(N,N-di-p-methoxyphenyl-amine)-9,9'-spirobifluorene (spiro-MeOTAD).

Fullerenes, especially C60 and derivatives thereof such as PCBM (=[6,6]-phenyl-$C_{61}$-butyric acid methyl ester). In such cases, the fullerene derivative would be a hole conductor.

Copper(I) iodide, copper(I) thiocyanate.

p-n-Mixed materials, i.e. donor and acceptor in one material, polymer, block copolymers, polymers with C60s, C60 azo dyes, trimeric mixed material which comprises compounds of the carotenoid type, porphyrin type and quinoid liquid-crystalline compounds as donor/acceptor systems, as described by Kelly in S. Adv. Mater. 2006, 18, 1754.

An aspect of the present teaching relates to the fabrication of an electroluminescent (EL) arrangement comprising an upper electrode, a lower electrode, wherein at least one of said electrodes is transparent, an electroluminescent layer and optionally an auxiliary layer, wherein the electroluminescent arrangement comprises a semiconductor component prepared fro a composition according to the invention. An EL arrangement is characterized by the fact that it emits light when an electrical voltage is applied with flow of current. Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and organic light-emitting diode (OLEDs) are used synonymously. As a rule, EL arrangements are constructed from several layers. At least on of those layers contains one or more organic charge transport compounds. The layer structure is in principle as follows:

1. Carrier, substrate
2. Base electrode (anode)
3. Hole-injecting layer
4. Hole-transporting layer
5. Light-emitting layer
6. Electron-transporting layer
7. Electron-injecting layer
8. Top electrode (cathode)
9. Contacts
10. Covering, encapsulation This structure represents the most general case and can be simplified by omitting individual layers, so that one layer performs several tasks. In the simplest case an EL arrangement consists of two electrodes between which an organic layer is arranged, which fulfills all functions, including emission of light. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. In principle OLEDs according to the invention can be produced by methods known to those skilled in the art. The OLED can be produced by successive deposition of the individual layers onto a suitable substrate. In a suitable embodiment, all layers are prepared by solution processing. In an alternative embodiment, at least one layer that does not contain the semiconductor A) may be coated by vapour phase deposition techniques known to those skilled in the art.

Suitable as substrate 1 are transparent carriers, such as glass or plastics films (for example polyesters, such as polyethylene terephthalate or polyethylene naphthalate, polycarbonate, polyacrylate, polysulphone, polyimide foil). Suitable as transparent and conducting materials are a) metal oxide, for example indium-tin oxide (ITO), tin oxide (NESA), etc. and b) semi-transparent metal films, for example Au, Pt, Ag, Cu, etc.

At least one semiconductor A) serves as a charge transport material (electron conductor). Thus, at least one of the following layers: the electron-injecting layer, the electron transporting layer or part of the transparent electrode incorporates a semiconductor component prepared from a composition according to the invention.

In the EL applications according to the invention low molecular weight or oligomeric as well as polymeric materials may be used as light-emitting layer 5. The substances are characterized by the fact that they are photoluminescing. Accordingly, suitable substances are for example fluorescent dyes and fluorescent products that are forming oligomers or are incorporated into polymers. Examples of such materials are coumarins, perylenes, anthracenes, phenanthrenes, stilbenes, distyryls, methines or metal complexes such as $Alq_3$ (tris(8-hydroxyquinolinato)aluminium), etc. Suitable polymers include optionally substituted phenylenes, phenylene vinylenes or polymers with fluorescing segments in the polymer side chain or in the polymer backbone. A detailed list is given in EP-A-532 798. Preferably, in order to increase the luminance, electron-injecting or hole-injecting layers (3 and/or 7) can be incorporated into the EL arrangements. A large number of organic compounds that transport charges (holes and/or electrons) are described in the literature. Mainly low molecular weight substances are used, which are suitable for solution processing. A comprehensive survey of the classes of substances and their use is given for example in the following publications: EP-A 387 715, U.S. Pat. Nos. 4,539,507, 4,720,432 and 4,769,292. A preferred material is PEDOT (poly-(3,4-ethylenedioxythiophene)) which can also be employed in the transparent electrode of the OLEDs.

As a result of the use of the composition according to the invention it is possible to obtain OLEDs with high efficiency. Those OLEDs can be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cell phones, laptops, digital cameras, vehicles and destination displays on buses and trains. Moreover, the composition according to the invention may be used for the fabrication of OLEDs with inverse structure. The structure of inverse OLEDs and the materials typically used therein are known to those skilled in the art.

The following figures and examples serve to illustrate the invention and should not be interpreted as limiting.

The following compounds (A) were used:

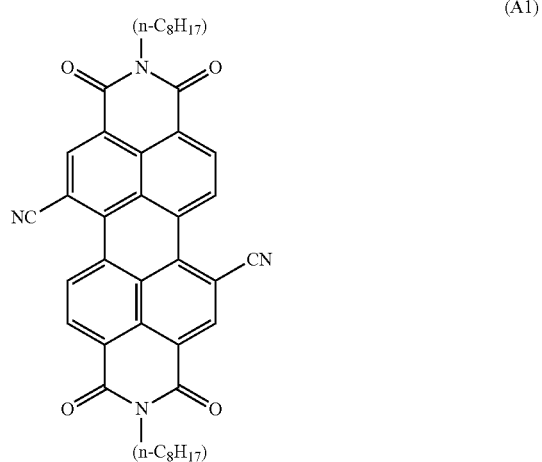

(A1)

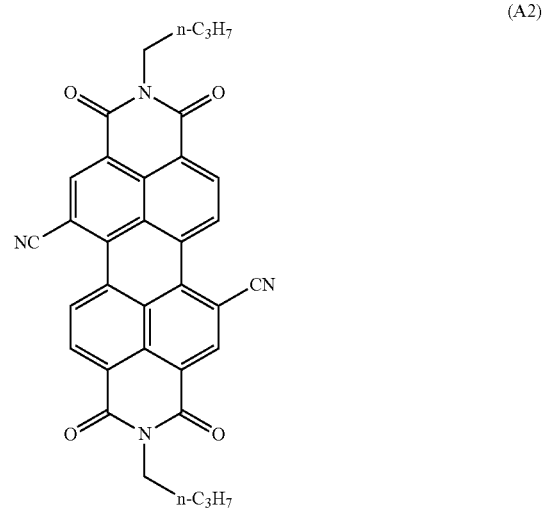

(A2)

(A3) 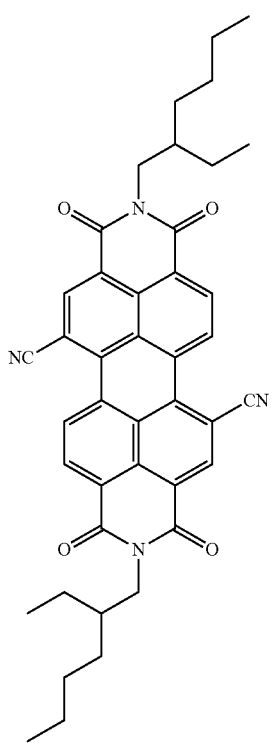

(A4) 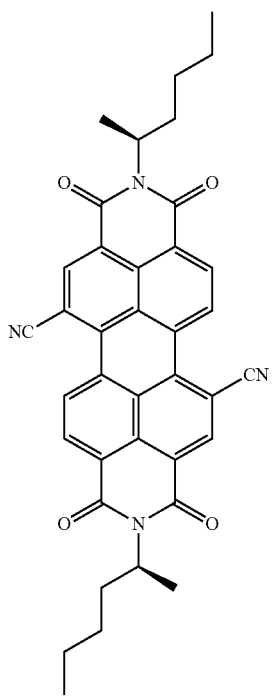

(A5) 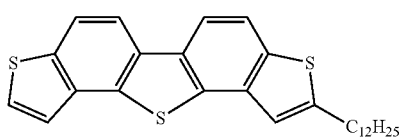

(A6) 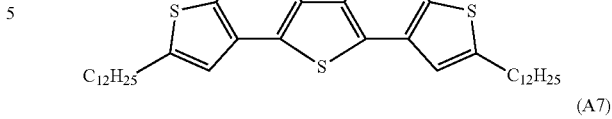

(A7) 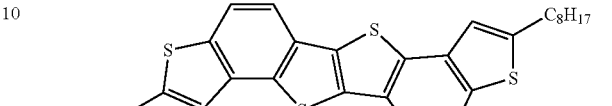

(A8) 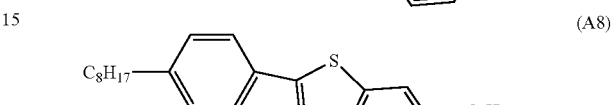

(A9) 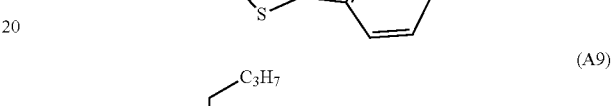

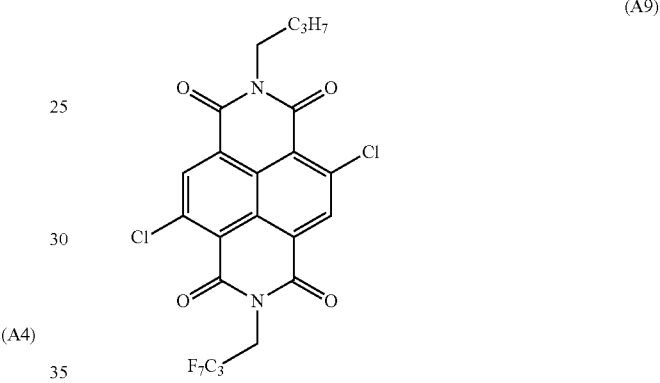

As compound B) the following phthalates were employed:
Dimethylphthalate (DMP)
Diethylphthalate (DEP)
Diallylphthalate (DAP)
Dibutylphthalate (DBP)

The following organic solvents/cosolvents C) were used:
Ethylacetate (EthAc)
Acetylacetone (Acac)

BRIEF DESCRIPTION OF THE DRAWINGS

FIG. 10a shows the transfer characteristics of the semiconductor obtained by inkjet printing of compound A3) from a DMP solution onto a wafer with a 30 nm insulating dielectric layer of $Al_2O_3$ (example 13) with $U_{GS}$=−30 V to +60 V with $U_{DS}$=50 V.

FIG. 10b shows the transfer characteristics of the semiconductor obtained by inkjet printing of compound A3) from a DMP solution onto a wafer with a 30 nm insulating dielectric layer of $Al_2O_3$ (example 13) with $U_{GS}$=−30 V to +60 V with $U_{DS}$=50 V.

FIG. 14a shows the transfer characteristics of the semiconductor obtained by drop casting of compound A4) from a DMP:Toluene (1:3) solution onto a wafer (example 28) with $U_{GS}$=−2 V to 10 V with $U_{DS}$=3 V.

FIG. 14b shows the output characteristics of the semiconductor obtained by drop casting of compound A4) from a DMP:Toluene (1:3) solution onto a wafer (example 28) with $U_{DS}$=0 V to 8 V with $U_{GS}$=0, 2, 4, 6, 8, and 10 V.

EXAMPLES

I) Optical Characterization

For the direct growth of well-oriented organic crystals of the compounds A) a solution containing compound A) is placed on a $SiO_2$ substrate by means of using a micropipette at 60 to 100° C. and ambient pressure. The temperature of the substrate is kept constant. As the liquid starts to evaporate, the crystallization of the organic semiconductors takes place. For the formation of crystalline films, the coated substrates were kept at 90° C. for 2 hours. The same technique can be used to deposit an organic semiconductor material on the channel region in OFETs. In photographs taken by polarized light microscopy of the organic layers produced with various semiconductor materials A), compounds B) and optionally cosolvents C) using the method of the invention, the organic layers exhibit different colors depending on the thickness of the material. The different morphologies observed under the polarized light microscope generally correlate with different electrical properties of the layer. It has been observed that larger crystals are associated with fewer grain boundaries, thus leading to improved electrical properties—in particular as far as charge carrier mobility μ is concerned.

Example 1: Drop-Casting of Semiconductor A1

Figure 1A:
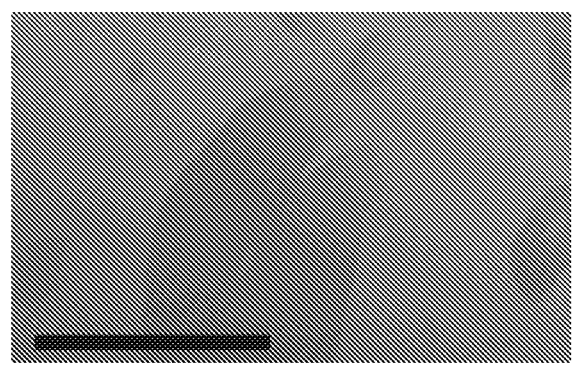
FIG. 1a shows the polarized optical micrograph of the crystalline organic film obtained by drop-casting of compound A1) from DMP (example 1.1). The black bar at the left bottom of the image shows a distance of 50 μm.
Figure 1B:
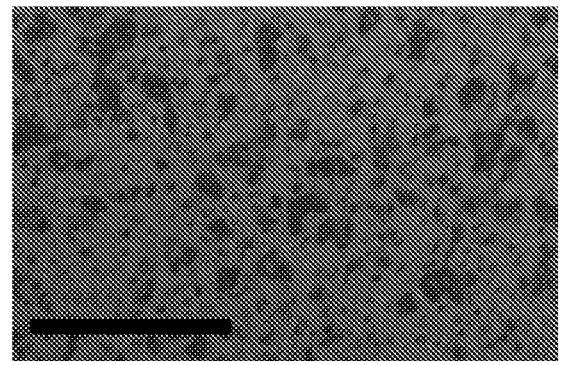
FIG. 1b shows the polarized optical micrograph of the crystalline organic film obtained by drop-casting of compound A1) from EthAc (comparative example 1.4). The black bar at the left bottom of the image shows a distance of 50 μm.

A 0.1 wt. % solution of A1) in a solvent according to table 1 is applied to a $SiO_2$ substrate and the solvent allowed to evaporate. For the preparation of the solutions of A1) in the phthalates the semiconductor is stirred in the phthalate at 80° C. for 60 minutes. FIG. 1a shows the polarized optical micrograph of the crystalline organic film obtained by drop-casting of compound A1) from DMP and FIG. 1b shows the micrograph of film obtained by drop-casting of compound A1) from EthAc. As can be seen, the crystals obtained from the compositions of the invention show remarkably larger crystalline areas.

TABLE 1

| example | solvent | crystal length [µm] | crystal width [µm] |
|---|---|---|---|
| 1.1 | DMP | 50 | 5 |
| 1.2 | DEP | 100 | 30 |
| 1.3 | DAP | 100 | 20 |
| C1.4[+)] | EthAc | 3[#)] | 0.5[#] |

[+)]comparative,
[#)]small polycrystalline to amorphous disconnected agglomerates Example 2: Drop-Casting of Semiconductor A2

A 0.1 wt. % solution of A2) in a solvent according to table 1 is applied to a SiO$_2$ substrate and the solvent allowed to evaporate. For the preparation of the solutions of A2) in the phthalates the semiconductor is stirred in the phthalate at 80° C. for 60 minutes. In the polarized optical micrograph the crystals obtained from the compositions of the invention show remarkably larger crystalline areas.

TABLE 2

| example | solvent | crystal length [µm] | crystal width [µm] |
|---|---|---|---|
| 2.1 | DMP | 35 | 5 |
| 2.2 | DEP | 100 | 50 |
| 2.3 | DAP | 60 | 50 |
| C2.4[+)] | EthAc | 20[#)] | 10[#)] |

[+)]comparative,
[#)]small polycrystalline to amorphous disconnected agglomerates Example 3: Drop-Casting of Semiconductor A3

A 0.1 wt. % solution of A3) in a solvent according to table 1 is applied to a SiO$_2$ substrate and the solvent allowed to evaporate. For the preparation of the solutions of A3) in the phthalates the semiconductor is stirred in the phthalate at 80° C. for 60 minutes. In the polarized optical micrograph the crystals obtained from the compositions of the invention show remarkably larger crystalline areas.

TABLE 3

| example | solvent | crystal length [µm] | crystal width [µm] |
|---|---|---|---|
| 3.1 | DAP | 200 | 250 |
| C3.2[+)] | EthAc | 20[#)] | 3[#)] |
| C3.3[+)] | Acac | 20[#)] | 3[#)] |

[+)]comparative,
[#)]small polycrystalline to amorphous disconnected agglomerates Example 4: Drop-Casting of Semiconductor A4

A 0.1 wt. % solution of A4) in a solvent according to table 1 is applied to a SiO$_2$ substrate and the solvent allowed to evaporate. For the preparation of the solutions of A4) in the phthalates the semiconductor is stirred in the phthalate at 80° C. for 60 minutes. In the polarized optical micrograph the crystals obtained from the compositions of the invention show remarkably larger crystalline areas.

TABLE 4

| example | solvent | crystal length [µm] | crystal width [µm] |
|---|---|---|---|
| 4.1 | DMP | 500 | 200 |
| 4.2 | DEP | 1200 | 650 |
| 4.3 | DAP | 250 | 150 |
| C4.3[+)] | EthAc | 3[#)] | 2[#)] |

[+)]comparative,
[#)]small polycrystalline to amorphous disconnected agglomerates II) Preparation and Electrical Characterization of OFET Devices Example 5: Drop-Casting of A4) from DMP Solution on a SiO$_2$ Wafer A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 µm PTFE filter. Si/SiO$_2$ wafers from WRS Materials heavily p-doped with boron (550 to 600 µm thickness, 100 nm insulating dielectric layer of thermally oxidized silicon) were used as back gate substrate. 1 to 10 µL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 µm and channel length (L) of 100 µm. Electrical characterization was conducted in a dark box under ambient conditions using an Agilent 4145C Semiconductor Parameter Analyzer.

Figure 2A:
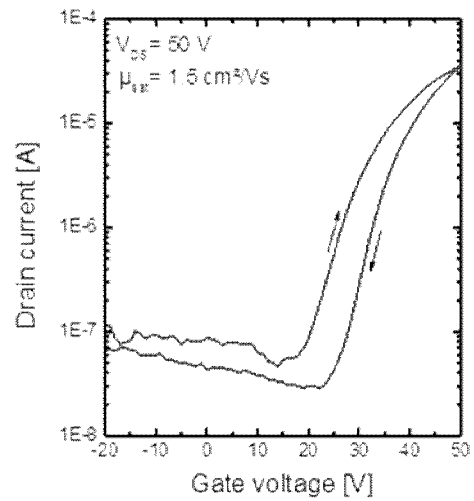
FIG. 2a shows the transfer characteristics of the semiconductor obtained by drop casting of compound A4) from a DMP solution (example 5) with $U_{GS}$=−20 V to +50 V with $U_{DS}$=50 V
Figure 2B:
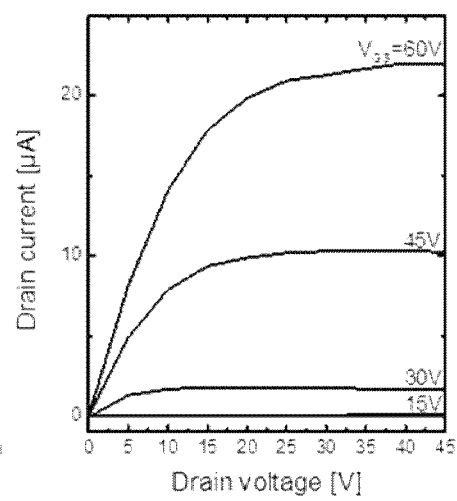
FIG. 2b shows the output characteristics of the semiconductor obtained by drop casting of compound A4) from a DMP solution (example 5) with $U_{DS}$=0 V to +45V with $U_{GS}$=15, 30, 45 and 60V.

The measurement results are depicted in FIGS. 2a and 2b, respectively.

Example 6: Drop-Casting of A4) from DMP:Acac (1:9) Solution on a SiO$_2$ Wafer

A 0.1 wt.-% solution of the semiconductor material A4) was prepared by dissolution in a 1:9 mixture of dimethyl phthalate and acetylacetone for 1 h at 80° C. and then stirred for further 30 minutes. The solution was allowed to cool to ambient temperature and was filtered through a 0.2 µm PTFE filter. Si/SiO$_2$ wafers from WRS Materials heavily p-doped with boron (550 to 600 µm thickness, 100 nm insulating dielectric layer of thermally oxidized silicon) were used as back gate substrate. 1 to 10 µL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 µm and channel length (L) of 100 µm. Electrical characterization was conducted in a dark box under ambient conditions using an Agilent 4145C Semiconductor Parameter Analyzer.

Figure 3A:
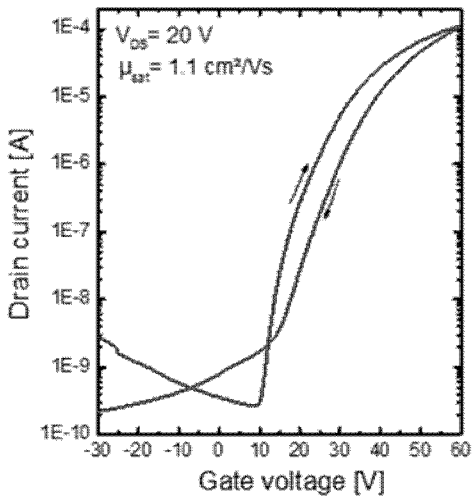
FIG. 3a shows the transfer characteristics of the semiconductor obtained by drop casting of compound A4) from a DMP:Acac (1:9) solution (example 6) with $U_{GS}$=−30 V to +60 V with $U_{DS}$=20 V
Figure 3B:
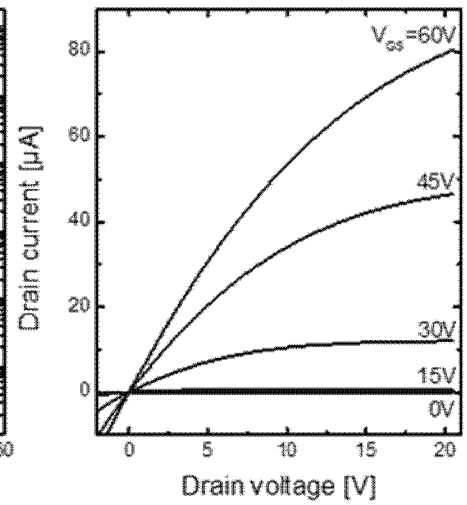
FIG. 3b shows the output characteristics of the semiconductor obtained by drop casting of compound A4) from a DMP:Acac (1:9) solution (example 6) with $U_{DS}$=0 V to +20 V with $U_{GS}$=15, 30, 45 and 60V.

The measurement results are depicted in FIGS. 3a and 3b, respectively.

Example 7: Drop-Casting of A4) from a DMP Solution on an Al$_2$O$_3$ Layer

A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate. 1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 4A:
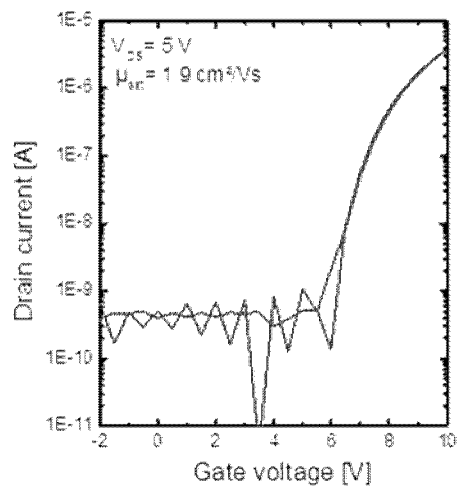
FIG. 4a shows the transfer characteristics of the semiconductor obtained by drop casting of compound A4) from a DMP solution onto a wafer with a 30 nm insulating dielectric layer of $Al_2O_3$ (example 7) with $U_{GS}$=−2 V to +10 V with $U_{DS}$=5 V.
Figure 4B:
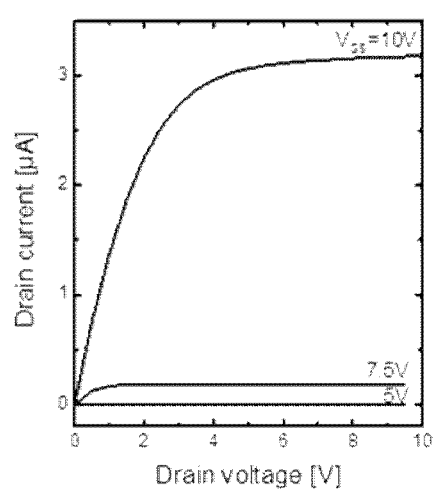
FIG. 4b shows the output characteristics of the semiconductor obtained by drop casting of compound A4) from a DMP solution onto a wafer with a 30 nm insulating dielectric layer of $Al_2O_3$ (example 7) with $U_{DS}$=0 V to +10 V with $U_{GS}$=5, 7.5 and 10 V.

The measurement results are depicted in FIGS. 4a and 4b, respectively.

Example 8: Drop-Casting of A4) from a DMP Solution on Al$_2$O$_3$ after Surface Modification A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate. Prior to material deposition, a surface treatment was conducted; the substrate was exposed to O$_2$ plasma for 300 seconds. 4-Ethoxyphenylphosphonic acid (CAS 69387-02-6) was dissolved in isopropanol at a concentration of 2 mMol (typically 4 mg/10 ml) and stirred at room temperature for 20 minutes. The substrate was immersed in the solution for 1 hour in a covered petri dish. After subsequent rinsing with isopropanol and drying under N$_2$, the substrates were baked at 150° C. on a hotplate. 1 to 10 μL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 5A:
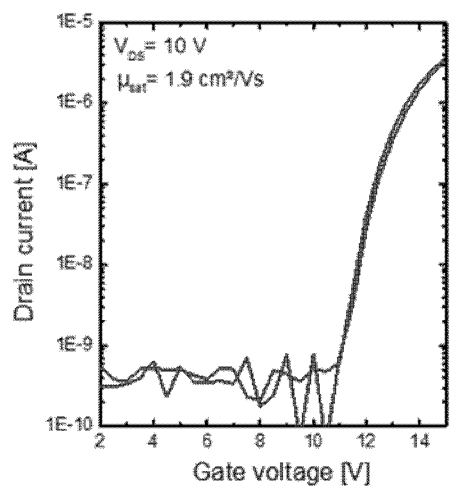
FIG. 5a shows the transfer characteristics of the semiconductor obtained by drop casting of compound A4) from a DMP solution onto a wafer after surface modification with 4-ethoxyphenylphosphonic acid (example 8) with $U_{GS}$=+2 V to +15 V with $U_{DS}$=10V
Figure 5B:
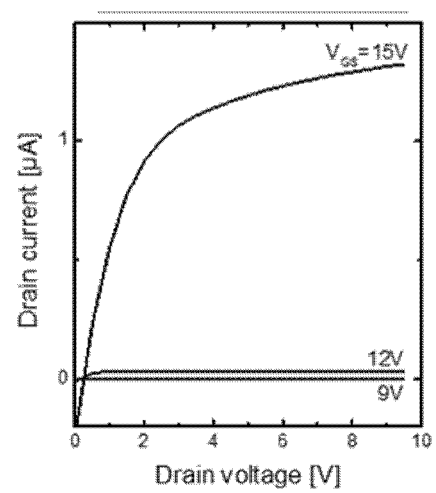
FIG. 5b shows the output characteristics of the semiconductor obtained by drop casting of compound A4) from a DMP solution onto a wafer after surface modification with 4-ethoxyphenylphosphonic acid (example 8) with $U_{DS}$=0 V to +10 V with $U_{GS}$=9, 12 and 15 V.

The measurement results are depicted in FIGS. 5a and 5b, respectively.

Example 9: Drop-Casting of A4) from a DMP Solution on a PET Substrate, Production of a Bottom-Contact Top-Gate Field Effect Transistor Using a PVCH/PMMA Top Gate A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 μm PTFE filter. A polyethylene terephthalate (PET) foil (Hostaphan 4600GN 175 from Mitsubishi Polyester Film) was used as substrate. Gold contacts (Umicore, 99.99%) were deposited at a base pressure of 6×10$^{-6}$ mbar through a kapton shadow mask via thermal evaporation yielding a channel width (W) of 500 μm and channel length (L) of 50 μm. 1 to 10 μL of solution was deposited onto the substrate on a hotplate at 60 to 90° C. in a flow box. After complete evaporation of the solvent the sample was put in a vacuum oven at 70° C. for 1 h to eliminate residual solvent. Polyvinylcyclohexane (PVCH) (0.4 wt % in cyclohexane) was spin-coated (4000 RPM, 30 seconds) and dried for 5 minutes at 90° C. Polymethylmethacrylate (PMMA) (4 to 7 wt.-% in butylacetate/ethyl-lactate [4:6]) was spin-coated (2000 RPM/60 seconds) and dried for 120 seconds at 90° C. The PVCH/PMMA dielectric thickness was 420 nm (6 r=4). Electrical characterization was conducted in a dark box under ambient conditions using an Agilent 4145C Semiconductor Parameter Analyzer.

Figure 6A:
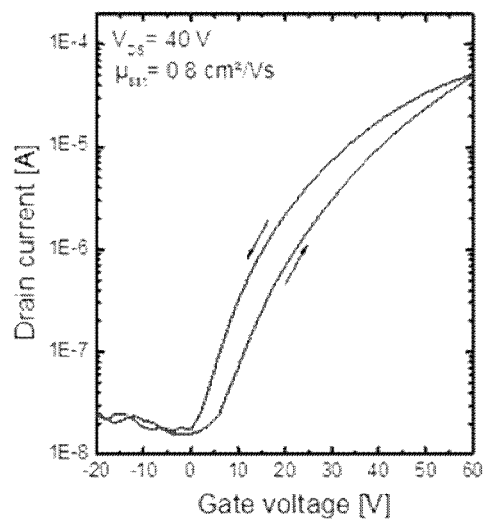
FIG. 6a shows the transfer characteristics of the semiconductor obtained by drop casting of compound A4) from a DMP solution onto a polyethylene terephthalate foil as substrate (example 9) with $U_{GS}$=−20 V to +60 V with $U_{DS}$=40 V.
Figure 6B:
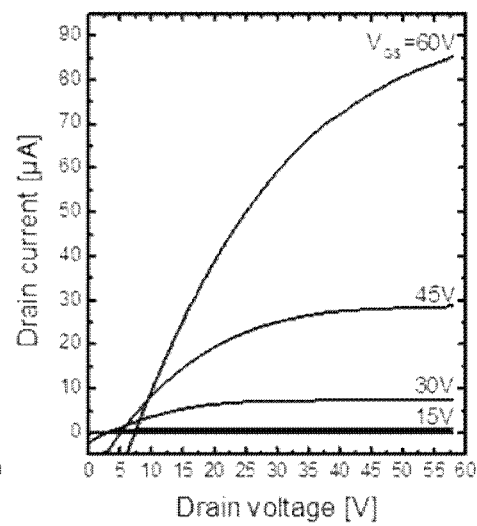
FIG. 6b shows the output characteristics of the semiconductor obtained by drop casting of compound A4) from a DMP solution onto a polyethylene terephthalate foil as substrate (example 9) with $U_{DS}$=0 V to +60 V with $U_{GS}$=15, 30, 45 and 60 V.

The measurement results are depicted in FIGS. 6a and 6b, respectively.

Example 10: Inkjet Printing of A4) from DMP Solution on a SiO$_2$ Wafer

A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 100 nm insulating dielectric layer of thermally oxidized silicon) were used as back gate substrate. The ink was printed with a Dimatix DMP2831 printer at a drop space of 20 μm with the nozzle at 35° C. and the printing plate at room temperature. The printed substrates were dried 5 h at 60° C. in ambient air followed by a second drying step for one hour at 110° C. in a vacuum oven (about 5 mbar pressure). After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 μm and channel length (L) of 100 μm. Electrical characterization was conducted in a dark box under ambient conditions using an Agilent 4145C Semiconductor Parameter Analyzer.

Figure 7A:
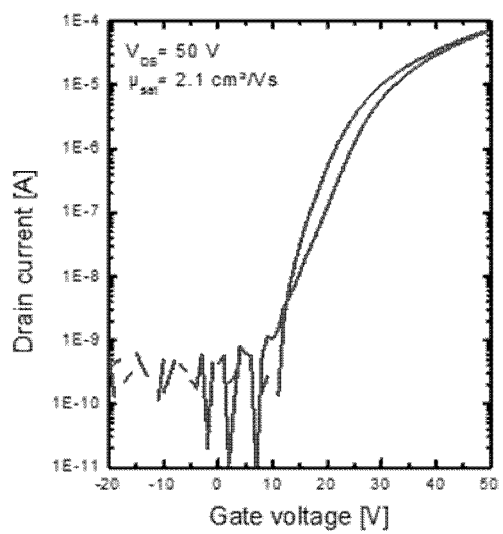
FIG. 7a shows the transfer characteristics of the semiconductor obtained by inkjet printing of compound A4) from a DMP solution onto a $SiO_2$ wafer (example 10) with $U_{GS}$=−20 V to +50 V with $U_{DS}$=50 V.
Figure 7B:
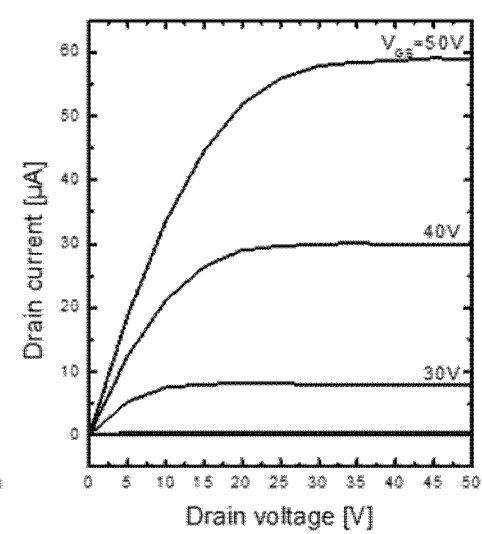
FIG. 7b shows the output characteristics of the semiconductor obtained by inkjet printing of compound A4) from a DMP solution onto a $SiO_2$ wafer (example 10) with $U_{DS}$=0 V to +50 V with $U_{GS}$=30, 40 and 50 V.

The measurement results are depicted in FIGS. 7a and 7b, respectively.

Example 11: Inkjet Printing of A4) from a DMP Solution on Al$_2$O$_3$ after Surface Modification A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 μm PTFE filter. Si/SiO$_2$ wafers from WRS Materials heavily p-doped with boron (550 to 600 μm thickness, 30 nm insulating dielectric layer of Al$_2$O$_3$) were used as back gate substrate. Prior to material deposition, a surface treatment was conducted; the substrate was exposed to O$_2$ plasma for 300 seconds. 4-Ethoxyphenylphosphonic acid, (CAS 69387-02-6) was dissolved in isopropanol at a concentration of 2 mMol (typically 4 mg/10 ml) and stirred at room temperature for 20 minutes. The substrate was immersed in the solution for 1 hour in a covered petri dish. After subsequent rinsing with isopropanol and drying under N2, the substrates were baked at 150° C. on a hotplate. The ink was printed with a Dimatix DMP2831 printer at a drop space of 20 μm with the nozzle at 35° C. and the printing plate at room temperature. The printed substrates were dried 5 h at 60° C. in ambient air followed by a second drying step for one hour at 110° C. in a vacuum oven (about 5 mbar pressure). After complete evaporation of solvent the sample was put in a vacuum oven for 1 h at 70° C. to eliminate residual solvent trapped in the film. Gold contacts (Umicore, 99.99%) were deposited at a base pressure of 6E-6 mbar through a kapton shadow mask via thermal evaporation yielding a typical channel W/L of 200 µm/100 µm. Electrical characterization was conducted in a dark box under ambient conditions using an Agilent 4145C Semiconductor Parameter Analyzer.

Figure 8A:
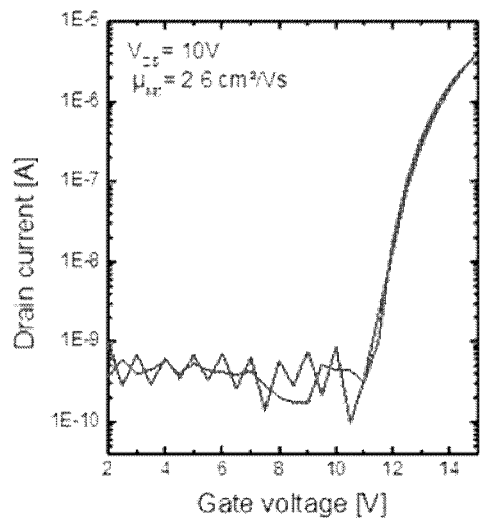
FIG. 8a shows the transfer characteristics of the semiconductor obtained by inkjet printing of compound A4) from a DMP solution onto an $Al_2O_3$ wafer after surface modification (example 11) with $U_{GS}$=+2 V to +15 V with $U_{DS}$=10 V.
Figure 8B:
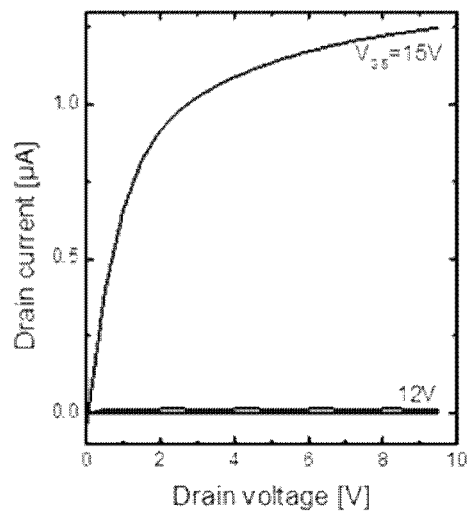
FIG. 8b shows the output characteristics of the semiconductor obtained by inkjet printing of compound A4) from a DMP solution onto an $Al_2O_3$ wafer after surface modification (example 11) with $U_{DS}$=0 V to +10 V with $U_{GS}$=12 and 15 V.

The measurement results are depicted in FIGS. 8a and 8b, respectively.

Example 12

Drop-Casting of A4) from a DMP Solution on a SiO$_2$ Wafer Using a Poly(Methyl Methacrylate)/Trimethylolpropane Triacrylate Bottom-Gate Dielectric A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 µm PTFE filter. Si/SiO$_2$ wafers from WRS Materials heavily p-doped with boron (550 to 600 µm thickness, 100 nm insulating dielectric layer of thermally oxidized silicon) with a UV-crosslinked polymer dielectric were used as backgate substrate. The dielectric properties are summarized in the table below.

TABLE 5

| UV polymer | spin-coating RPM(time) | drying | crosslinking | $\varepsilon_r$ | film thickness |
|---|---|---|---|---|---|
| TMPTA/PMMA | 2000/10000 (60 seconds) | 10 min 90° C. | 10 × 10 LEDs UV meter 53" 23 mW/cm$^2$ | 3.5 | 328 nm |

$\varepsilon_r$ = relative permittivity (dielectric constant)

1 to 10 µL of solution was deposited onto the wafer on a hotplate at 60 to 90° C. in a flow box. After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a typical channel W/L of 200 µm/100 µm. Electrical characterization was conducted in a dark box under ambient conditions. Electrical characterization was conducted in a dark box under ambient conditions using an Agilent 4145C Semiconductor Parameter Analyzer.

Figure 9A:
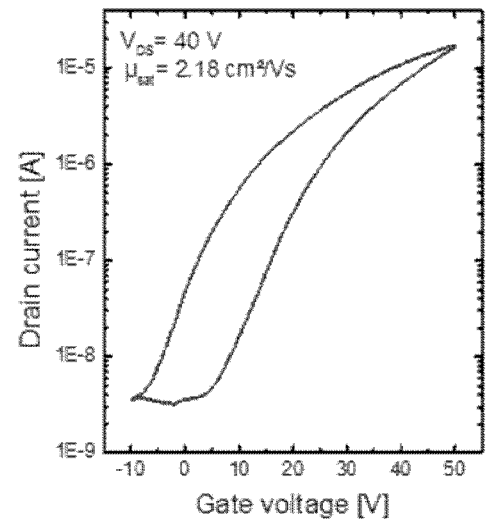
FIG. 9a shows the transfer characteristics of the semiconductor obtained by drop casting of compound A4) from a DMP solution onto a $SiO_2$ wafer using a poly(methyl methacrylate)/trimethylolpropane triacrylate bottom gate dielectric (example 12) with $U_{GS}$=−10 V to +50 V with $U_{DS}$=40 V.
Figure 9B:
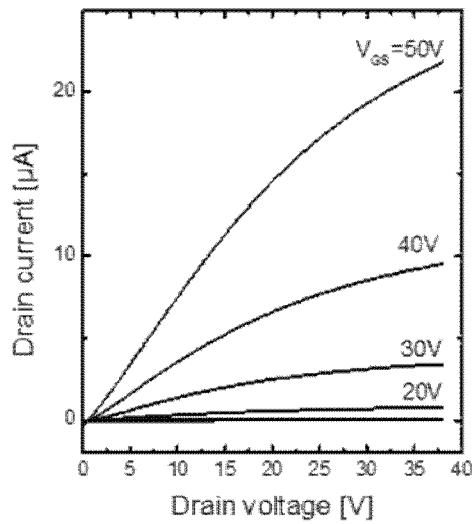
FIG. 9b shows the output characteristics of the semiconductor obtained by drop casting of compound A4) from a DMP solution onto a $SiO_2$ wafer using a poly(methyl methacrylate)/trimethylolpropane triacrylate bottom gate dielectric (example 12) with $U_{DS}$=0 V to +40 V with $U_{GS}$=20, 30, 40 and 50 V.

The measurement results are depicted in FIGS. 9a and 9b, respectively.

Example 13: Inkjet Printing of A3) from DMP Solution on Al$_2$O$_3$

A 0.1 wt.-% solution of the semiconductor material A4) was prepared by dissolution in dimethyl phthalate for 1 h at 80° C. and then stirred for further 30 minutes. The solution was allowed to cool to ambient temperature and was filtered through a 0.2 µm PTFE filter. Si/SiO$_2$ wafers from WRS Materials heavily p-doped with boron (550 to 600 µm thickness, 30 nm insulating dielectric layer of Al$_2$O$_3$) were used as back gate substrate. The ink was printed with a Dimatix DMP2831 printer at a drop space of 20 µm with the nozzle at 35° C. and the printing plate at room temperature. The printed substrates were dried 5 h at 60° C. in ambient air followed by a second drying step for one hour at 110° C. in a vacuum oven (about 5 mbar pressure). After complete evaporation of solvent the sample was put in a vacuum oven for 1 h at 70° C. to eliminate residual solvent trapped in the film. Gold contacts (Umicore, 99.99%) were deposited at a base pressure of 6×10$^{-6}$ mbar through a kapton shadow mask via thermal evaporation yielding a channel width (W) of 200 µm and channel length (L) of 100 µm. Electrical characterization was conducted in a dark box under ambient conditions using an Agilent 4145C Semiconductor Parameter Analyzer.

The measurement results are depicted in FIGS. 10a and 10b, respectively.

Examples 14 to 20

Sample Preparation:

Degenerately doped silicon wafers (wafers from WRS Materials heavily p-doped with boron, 550-600 µm thickness) coated with a 240 nm thermally grown silicon dioxide were used as substrate. They were subjected to 2 min oxygen plasma treatment (100 W, 20 standard cubic centimeters per minute (sccm) gas flow) and subsequently immersed into a 0.2 vol % solution of octadecyltrichlorosilane (OTS) in toluene for 17 minutes at room temperature. Subsequently the sample was removed from the solution, rinsed with toluene and baked for 30 min at 90° C. Subsequently a 0.5-1 mm thick layer of polydimethylsiloxane (PDMS) comprising holes with a diameter of 7.3 mm was placed onto the hydrophobic substrate that was subsequently subjected to a 5 minutes treatment with air plasma. This plasma burns away the hydrophobic monolayer in the locations of the holes of the PDMS layer exposing the bare, more hydrophilic SiO$_2$ surface.

0.1 wt % of semiconductor powder was dissolved in DMP, a mixture of DMP and toluene or pure toluene and filtered through a 0.2 µm polytetrafluoroethylene (PTFE) filter. The substrate was placed on a hotplate (temperature for all solvents 70° C. except toluene, here 30° C. was used for drying) and 1 µL of the organic semiconductor solution was applied by drop casting with a pipette onto the hydrophilic areas. Substrates were removed once the solution had dried. The obtained crystalline semiconductor materials were examined under a polarized microscope in reflection mode. The results are shown in table 6.

TABLE 6

List of semiconductors tested:

| | | solvent/crystal form | | |
|---|---|---|---|---|
| example no. | semiconductor | DMP thin layers | DMP:Toluene(1:3) thin layers | Toluene thin layers |
| 14 | A9 | yes | not measured | no |
| 15 | A4 | Yes | Yes | No |
| 16 | A3 | yes | yes | no |
| 17 | A5 | yes | yes | no |
| 18 | A6 | yes | yes | no |
| 19 | A7 | yes | yes | no |
| 20 | A8 | yes | yes | not measured |

With DMP and mixtures of DMP and toluene in each case good semiconductor materials having a large area of thin connected crystals were obtained. If toluene is used as solvent the obtained semiconductor material consists of thick disconnected crystals.

Examples 21 to 24

Polystyrene (PS), molecular weight 2,000,000 (obtained from Alfa Aesar; PS-Lot: K05Y052), was dissolved in the respective solvents at room temperature and stirred until all polymer was dissolved. Then 0.1 wt % of the organic semiconductor (A4) was dissolved in the mixture. Microscopy cover glass-slides were used as substrates and were thoroughly rinsed with acetone first. All solutions were deposited by drop casting and drying was performed at 70° C. on a hotplate. The obtained crystalline semiconductor materials were examined by polarized optical microscopy. The results are shown in table 7. With all solvent mixtures containing a solvent in the sense of the invention in each case good semiconductor materials having a large area of thin connected crystals were obtained.

TABLE 7

List of solvent mixtures and solvent-polymer mixtures tested

| example no. | solvent mixture, polymer-solvent mixture | Viscosity [mPas] | Surface tension [mN/m] | crystal form |
|---|---|---|---|---|
| 21 | DMP:PS (1.5 mg PS/1 g DMP) | 20 | not measured | thin |
| 22 | DEP:PS (2.3 mg PS/1 g DEP) | 19 | not measured | thin |
| 23 | DMP:PS (wire-bar coated) (1.5 mg PS/1 g DMP) | 20 | not measured | thin |
| 24 | DEP:PS (wire-bar coated) (2.3 mg PS/1 g DEP) | 19 | not measured | thin |

Examples 25-27 Sample Preparation

Degenerately doped silicon wafers coated with $Al_2O_3$ (30 nm thick, grown via atomic layer deposition) were subjected to a 2 minutes treatment with oxygen plasma (100 W, 20 sccm gas flow) and subsequently immersed into a 1.5 mM solution of tetradecyl phosphonic acid (TDPA) in isopropanol for 1 hour at room temperature. Subsequently the sample was removed from the solution and baked for 5 min at 120° C. This procedure yields a hydrophobic self-assembled monolayer (SAM) on the $Al_2O_3$ surface with a surface energy of 22 mN/m (surface energy determined via contact angle measurement). Subsequently a layer of PDMS having a thickness of 0.5-1 mm and comprising holes with a diameter of 7.3 mm was placed onto the hydrophobic substrate that was subsequently subjected to a 5 minutes treatment with air plasma. This plasma burns away the hydrophobic monolayer in the locations of the holes of the PDMS layer exposing the bare, more hydrophilic $Al_2O_3$ surface. The resulting plasma-treated hydrophilic areas of the substrate were then treated with 4-ethoxyphenylphosphonic acid (EPPA) in the same manner as described above for the TDPA SAM. This process yields a hydrophilic EPPA SAM in the circular regions that had been subjected to the second plasma treatment step. The surface energy of the EPPA-treated areas was determined to be 36 mN/m.

0.1 wt % of semiconductor powder was dissolved in the respective solvent for 1 h at 80° C. under constant shaking. After cooling the solution to room temperature it was filtered through a 0.2 µm PTFE filter. In the case that solvent mixtures were used, first the semiconductor was dissolved in the respective individual solvent, subjected to shaking at 80° C. for 1 h, filtered and subsequently mixed to the respective solvent ratios. 1 µL of the organic semiconductor solution was drop casted with a pipette onto the hydrophilic EPPA areas at an elevated substrate temperature (70° C., substrate placed on hotplate). After several hours to 2 days of drying at 70° C. the samples were transferred to a vacuum oven and heated to 60° C. to 90° C. for additional 3 hours to completely remove residual solvent. Optical images were recorded under a polarized microscope in reflection mode.

Example 25

Figure 11:
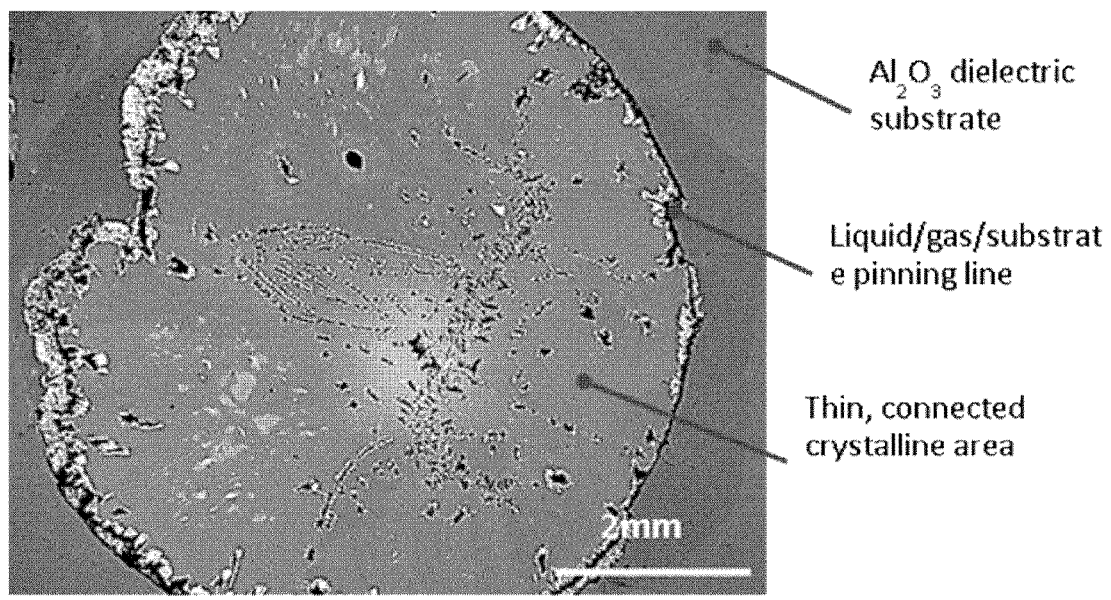
FIG. 11 shows the polarized optical micrograph of the crystalline organic film obtained by drop-casting of compound A1) from a mixture of DMP:Toluene (1:3) (example 25).

According to the afore-mentioned sample preparation method a crystalline material of semiconductor (A4) was prepared using a solvent mixture of DMP and toluene (wt. ratio 1:3). The solids content of the semiconductor solution was 0.1 wt. % and drying was performed at 70° C. on a hotplate. FIG. 11 shows the polarized optical micrograph of the obtained crystalline organic film. The combination of DMP with toluene as a solvent mixture according to the invention leads to a semiconductor material having a large area of thin connected continuous crystals.

Example 26 (Comparative)

Figure 12:
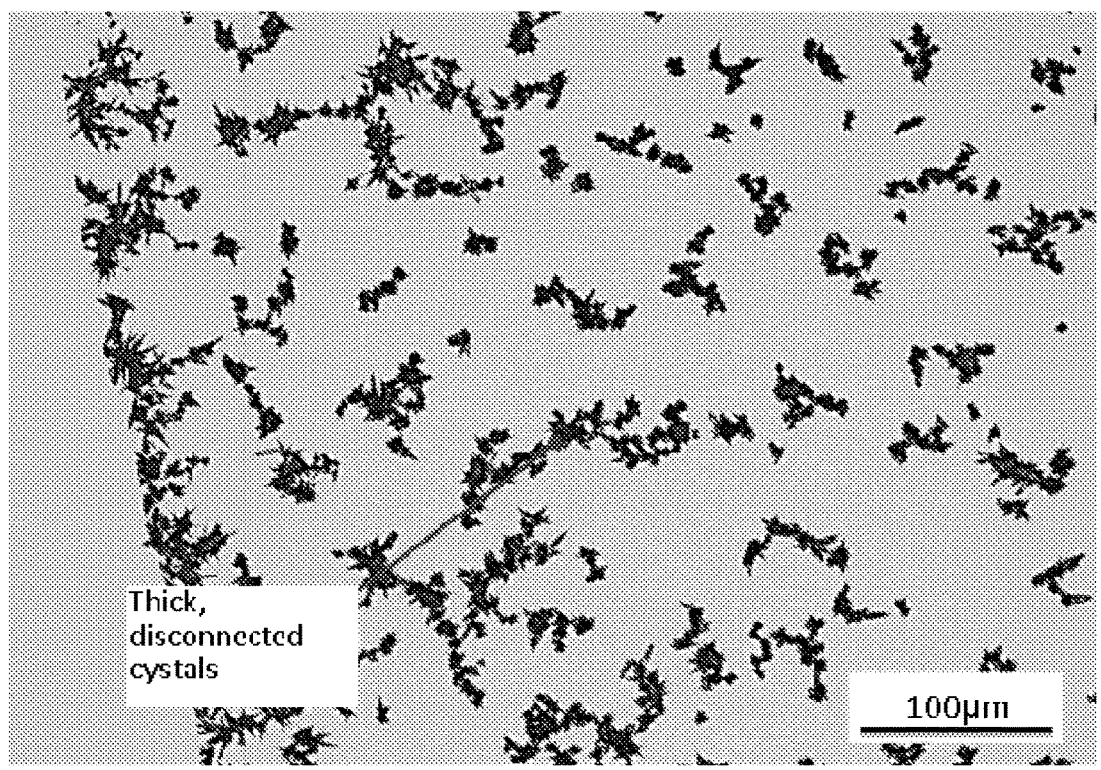
FIG. 12 shows the polarized optical micrograph of the crystalline organic film obtained by drop-casting of compound A1) from acetylacetone (comparative example 26).

According to the afore-mentioned sample preparation method a crystalline material of semiconductor (A4) was prepared using acetylacetone as solvent. The solids content of the semiconductor solution was 0.1 wt.-% and drying was performed at 70° C. on a hotplate. FIG. 12 shows the polarized optical micrograph of the obtained crystalline organic film. The use of a solvent that is not a solvent (B) in the sense of the invention leads to a semiconductor material having thick disconnected crystals.

Example 27 (Comparative)

Figure 13:
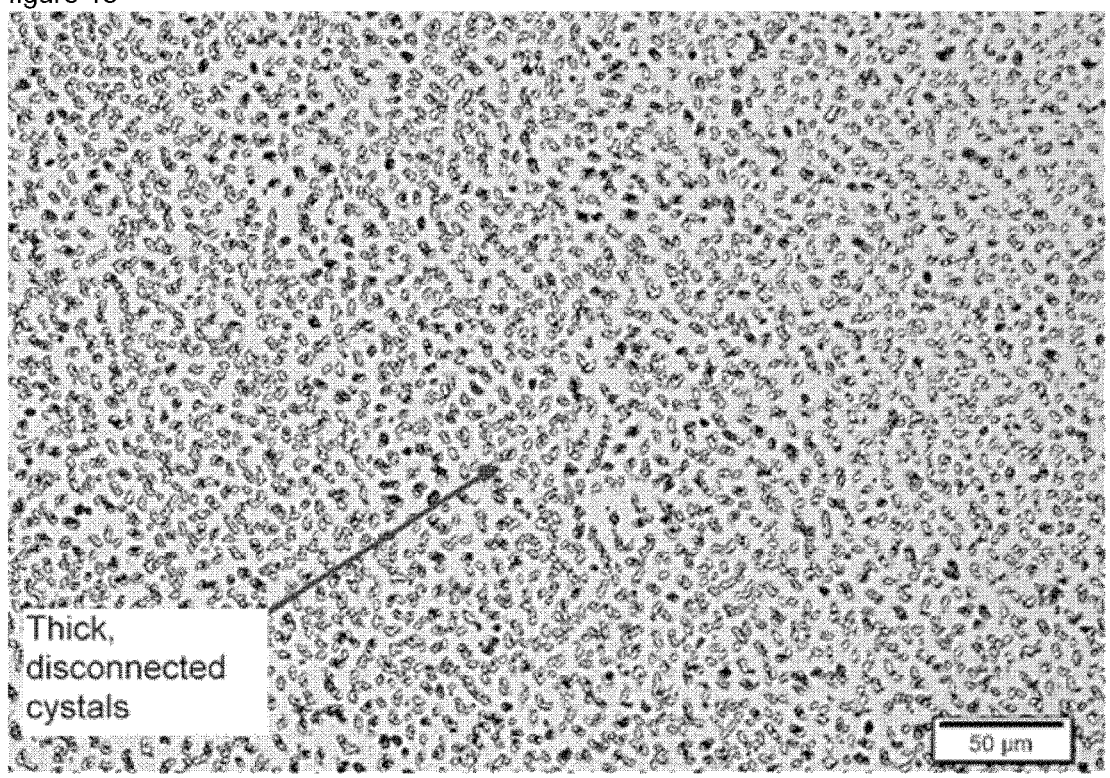
FIG. 13 shows the polarized optical micrograph of the crystalline organic film obtained by drop-casting of compound A1) from toluene (comparative example 27).

According to the afore-mentioned sample preparation method a crystalline material of semiconductor (A4) was prepared using toluene as solvent. The solids content of the semiconductor solution was 0.1 wt.-% and drying was performed at 30° C. on a hotplate. FIG. 13 shows the polarized optical micrograph of the obtained crystalline organic film. The use of toluene alone, being a solvent that is not a solvent (B) in the sense of the invention, leads to a semiconductor material having thick disconnected crystals.

Example 28: Drop-Casting of A4) from a DMP:Toluene (1:3) Mixture on $Al_2O_3$ after Surface Modification A 0.1 wt.-% solution of the semiconductor material A4) was prepared by dissolution in dimethyl phthalate for 1 h at 80° C. and then stirred for further 30 minutes. A second 0.1 wt.-% solution of the semiconductor material A4) was prepared by dissolution in toluene for 1 h at 80° C. and then stirred for further 30 minutes. The two solutions were mixed at a weight ratio of 1 (DMP) to 3 (toluene). The combined solution was allowed to cool to ambient temperature and was filtered through a 0.2 µm PTFE filter. Silicon wafers from WRS Materials (heavily p-doped with boron, 550 to 600 µm thickness) coated with $Al_2O_3$ (30 nm thick, grown via atomic layer deposition) were subjected to a 2 minutes treatment with oxygen plasma (100 W, 20 sccm gas flow)

and subsequently immersed into a 1.5 mM solution of tetradecyl phosphonic acid (TDPA) in isopropanol for 1 hour at room temperature. Subsequently the sample was removed from the solution, rinsed with isopropanol and baked for 5 min at 120° C. on a hotplate. This procedure yields a hydrophobic self-assembled monolayer (SAM) on the $Al_2O_3$ surface with a surface energy of 22 mN/m (surface energy determined via water contact angle measurement). Subsequently a layer of PDMS having a thickness of 0.5-1 mm and comprising holes with a diameter of 8 mm was placed onto the hydrophobic substrate that was subsequently subjected to a 2 minutes treatment with air plasma (100 W, 20 sccm gas flow). This plasma burns away the hydrophobic monolayer in the locations of the holes of the PDMS layer exposing the bare, more hydrophilic $Al_2O_3$ surface. 1 to 10 µL of solution was deposited onto the wafer on a hotplate at 70° C. in a flow box. After complete evaporation of solvent the sample was put in a vacuum oven for 1 h at 90° C. to eliminate residual solvent trapped in the film. Gold contacts (Umicore, 99.99%) were deposited at a base pressure of $6 \times 10^{-6}$ mbar through a kapton shadow mask via thermal evaporation yielding a channel width (W) of 200 m and channel length (L) of 50 m. The degenerately doped silicon wafers were used as back gate substrate for electrical characterization, conducted in a dark box under ambient conditions using an Agilent 4145C Semiconductor Parameter Analyzer.

The measurement results are depicted in FIGS. 14a and 14b, respectively.

The invention claimed is:

1. A composition, comprising:

A) at least one organic semiconductor which is an rylene compound of formula (I.a):

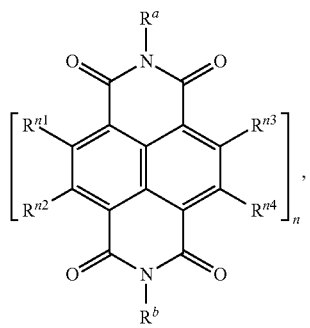

wherein:

n is 1 or 2, $R^a$ and $R^b$ are independently hydrogen or in each case an optionally substituted alkyl, alkenyl, alkadienyl, alkynyl, cycloalkyl, bicycloalkyl, cycloalkenyl, heterocycloalkyl, aryl, or heteroaryl group, $R^{n1}$, $R^{n2}$, $R^{n3}$ and $R^{n4}$ are independently of one another selected from the group consisting of hydrogen, F, Cl, Br and CN, such that at least one of $R^{n1}$, $R^{n2}$, $R^{n3}$ and $R^{n4}$ is not hydrogen; and B) at least one compound of formula (II.1) that is liquid at 20° C. and 1013 mbar:

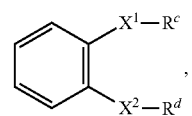

wherein:

$X^1$ and $X^2$ represent *—(C=O)—O—, where * is the point of linkage to the aromatic carbocycle, and $R^c$ and $R^d$ are independently selected from the group consisting of unbranched and branched $C_1$-$C_{12}$-alkyl and $C_2$-$C_{12}$-alkenyl.

2. The composition according to claim 1, wherein $R^a$ and $R^b$ are independently selected from the group consisting of hydrogen, linear $C_1$-$C_{30}$-alkyl, branched $C_3$-$C_{30}$-alkyl, perfluoro-$C_1$-$C_{30}$-alkyl, 1H,1H-perfluoro-$C_2$-$C_{30}$-alkyl, 1H,1H,2H,2H-perfluoro-$C_3$-$C_{30}$-alkyl, a radical of the formula G.1, a radical of the formula G.2 and a radical of the formula G.3:

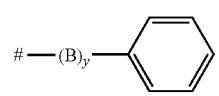

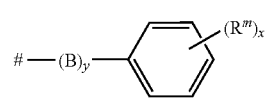

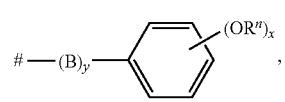

where:

\# represents the bonding side to a nitrogen atom,

B where present, is a $C_1$-$C_{10}$-alkylene group which may be interrupted by one or more nonadjacent groups which are selected from the group consisting of —O— and —S—, y is 0 or 1, $R^m$ is independently selected from the group consisting of $C_1$-$C_{30}$-alkyl, $C_1$-$C_{30}$-fluoroalkyl, fluorine, chlorine, bromine, $NE^3E^4$, nitro and cyano, where $E^3$ and $E^4$, independently of one another, are hydrogen, alkyl, cycloalkyl, heterocycloalkyl, aryl or hetaryl, $R^n$ is independently $C_1$-$C_{30}$-alkyl, and x in formulae G.2 and G.3 is 1, 2, 3, 4 or 5.

3. The composition according to claim 1, wherein $R^a$ and $R^b$ are selected from the group consisting of radicals of formulae (III.1), (III.2) and (III.3):

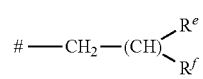

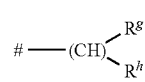

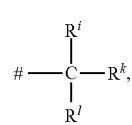

wherein:
# is a bonding site,
in the formula (III.1) $R^e$ and $R^f$ are independently $C_1$- to $C_{27}$-alkyl, where the sum of the carbon atoms of the $R^e$ and $R^f$ radicals is an integer from 2 to 28,
in the formula (III.2) $R^g$ and $R^h$ are independently $C_1$- to $C_{28}$-alkyl, where the sum of the carbon atoms of the $R^g$ and $R^h$ radicals is an integer from 2 to 29, and
in the formula (III.3) $R^i$, $R^k$ and $R^l$ are independently $C_1$- to $C_{27}$-alkyl, where the sum of the carbon atoms of the $R^i$, $R^k$ and $R^l$ radicals is an integer from 3 to 29.

4. The composition according to claim 1, wherein $R^a$ and $R^b$ have the same meaning.

5. The composition according to claim 1, wherein the component A) is a compound of formula (I.a1):

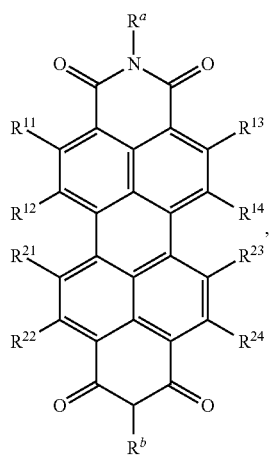

(I.a1)

wherein:
$R^a$ and $R^b$ are defined as above,
$R^{12}$ and $R^{23}$ are independently selected from the group consisting of F, Cl, Br, CN, and
$R^{11}$, $R^{13}$, $R^{14}$, $R^{21}$, $R^{22}$ and $R^{24}$ are hydrogen.

6. The composition according to claim 1, wherein the compound B) satisfies:
a Hansen solubility parameter (delta D) ranging from 15 to 20,
a Hansen solubility parameter (delta P) ranging from 7 to 12,
a Hansen solubility parameter (delta H) ranging from 3.5 to 5.5, and
a boiling point at 1013.25 mbar of at least 100° C.

7. The composition according to claim 1, wherein $R^c$ and $R^d$ are independently selected from the group consisting of methyl, ethyl, n-propyl, isopropyl, n-butyl, sec.-butyl, tert.-butyl, isobutyl, n-pentyl, n-hexyl, n-heptyl, n-octyl, 2-ethylhexyl, n-nonyl, isononyl, isodecyl, 2-propylheptyl, n-undecyl and isoundecyl.

8. The composition according to claim 1, wherein the compound B) is selected from the group consisting of dimethylphthalate, diethylphthalate, di(n-propyl)phthalate, di(n-butyl)phthalate, diallylphthalate and mixtures thereof.

9. The composition according to claim 1, wherein the organic semiconductor A) has a solubility in component B) at 20° C. of at least 0.01 mg/ml.

10. The composition according to claim 1, further comprising:

C) a cosolvent selected from the group consisting of an organic solvent different from the compound B) and mixtures thereof.

11. The composition according to claim 10, wherein the cosolvent C) is selected from the group consisting of:
aliphatic, cycloaliphatic and aromatic hydrocarbons,
aromatic ethers,
open chain aliphatic ethers, polyethers, ether alcohols and cyclic ethers,
ketones,
esters,
aliphatic and cycloaliphatic alcohols,
benzene based alcohols,
halogenated aromatic compounds,
thiophenols and alkylthio-substituted benzenes,
aromatic compounds comprising a phenyl group fused to a 5-, 6-, or 7-membered cycloheteroalkyl group,
5-membered heteroaryl compounds and benzo-fused 5-membered heteroaryl compounds,
aromatic carboxylic acids,
aromatic aldehydes,
trifluoromethyl-substituted benzene compounds,
cyano-substituted or isocyano-substituted benzene compounds,
nitro-substituted benzene compounds,
phenyl sulfones,
6-membered heteroaryl compounds and benzofused 6-membered heteroaryl compounds,
5-membered heteroaryl compounds and benzofused 5-membered heteroaryl compounds,
aprotic polar solvents, and
mixtures thereof.

12. The composition according to claim 10, wherein the organic semiconductor A) has a solubility in a mixture of components B) and C) at 20° C. of at least 0.01 mg/ml.

13. The composition according to claim 1, further comprising:
a viscosity-modifying additive.

14. A process, comprising applying the composition of claim 1 to at least a portion of the surface of a substrate to allow deposition of the at least one organic semiconductor A) on the substrate.

15. The process according to claim 14, wherein the composition is applied to the surface of the substrate by printing.

16. The process according to claim 14, wherein the surface of the substrate is a substrate coated with a dielectric.

17. The process according to claim 14, wherein:
the surface of the substrate or, if present, a dielectric coating on the substrate, is subjected to a surface modification prior to the application of the composition; and
a compound used for the surface modification is selected from the group consisting of silanes, phosphonic acids, carboxylic acids, hydroxamic acids, amines, phosphines, sulfur-comprising compounds and mixtures thereof.

18. The process according to claim 14, which produces a device selected from the group consisting of organic field-effect transistors, electroluminescent arrangements, organic solar cells and photodetectors.

19. The composition according to claim 1, wherein:
the at least one organic semiconductor is an rylene compound of formula (I.a) having the structure:

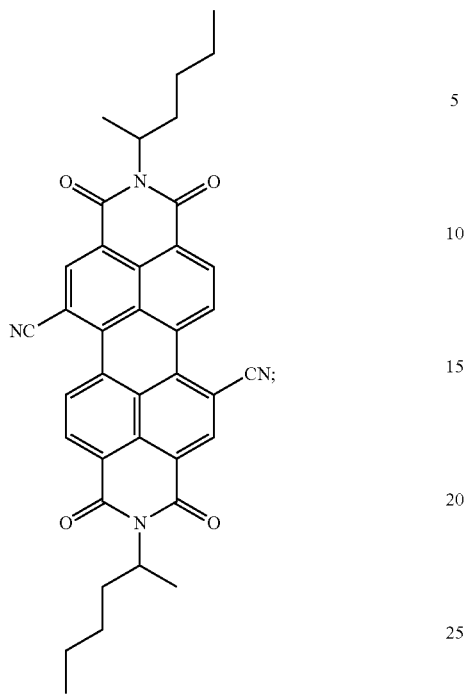
and
the at least one compound of formula (II) is dimethylphthalate.
* * * * *

UNITED STATES PATENT AND TRADEMARK OFFICE
CERTIFICATE OF CORRECTION

PATENT NO. : 10,454,037 B2  
APPLICATION NO. : 15/504851  
DATED : October 22, 2019  
INVENTOR(S) : Ilja Vladimirov et al.

Page 1 of 4

It is certified that error appears in the above-identified patent and that said Letters Patent is hereby corrected as shown below:

In the Specification

Column 2, Line 58, "mL" should read -- ml --,

Column 3, Line 1, "methylanisol," should read -- methylanisole, --,

Column 7, Line 61, "propyl pentyl" should read -- propylpentyl --,

Column 9, Line 63, "yland" should read -- yl and --,

Column 10, Line 30, "dibenzylamino;" should read -- dibenzylamino. --,

Column 10, Line 59, "4-sec." should read -- 4-sec --,

Column 12, Line 57, "4H[1" should read -- 4H-[1 --,

Column 15, Line 33, "$C_1$-$C_{30}$" should read -- $C_3$-$C_{30}$ --,

Column 18, Line 21, "R," should read -- $R^i$, --,

Column 18, Line 51, "2-m ethyltetradecyl," should read -- 2-methyltetradecyl, --, Column 19, Line 41, "1-ethyl heptyl," should read -- 1-ethylheptyl, --, Column 20, Line 55, "tert.-" should read -- tert- --, Column 23, Line 20, "((3S)" should read -- (3S) --, Column 23, Line 22, "((3S)" should read -- (3S) --, Signed and Sealed this  
Twenty-sixth Day of May, 2020

Andrei Iancu  
*Director of the United States Patent and Trademark Office*

Column 25, Line 20, "((3S)" should read -- (3S) --,

Column 25, Line 22, "((3S)" should read -- (3S) --,

Column 27, Line 11, "((3S)" should read -- (3S) --,

Column 27, Line 13, "((3S)" should read -- (3S) --,

Column 77, Line 7, "aryl," should read -- aryl. --,

Column 77, Line 61, "aryl," should read -- aryl. --,

Column 77, Line 63, "162015" should read -- IB2015 --,

Column 80, Line 13, "$Y^{1e}$ and $Y^{2e}$" should read -- $R^{1e}$ and $R^{2e}$ --, Column 83, Line 29, "sec.-" should read -- sec- --, Column 83, Line 30, "tert.-" should read -- tert- --, Column 84, Line 12, "di methylterephthalate," should read -- dimethylterephthalate, --, Column 85, Line 15, "alcohol" should read -- alcohol. --, Column 89, Line 22, "n-heptan," should read -- n-heptane, --, Column 90, Line 16, "2-methyl benzoate," should read -- 2-methylbenzoate, --, Column 90, Line 16, "3-methyl benzoate" should read -- 3-methylbenzoate --, Column 90, Line 23, "sec.-" should read -- sec- --, Column 90, Line 24, "tert.-" should read -- tert- --, Column 90, Lines 42-43, "methyl phenoxy" should read -- methylphenoxy --, Column 91, Line 35, "ethyl benzaldehyde" should read -- ethylbenzaldehyde --, Column 91, Lines 53-54, "methyl benzenecarbonitrile," should read -- methylbenzenecarbonitrile, --, Column 91, Line 58, "4-tolyl isocyanide" should read -- 4-tolylisocyanide --, Column 92, Lines 57-58, "ethyl 5 quinolinecarboxylate," should read -- ethyl 5-quinolinecarboxylate, --, Column 93, Line 7, "trifluoromethyquinoxaline," should read -- trifluoromethylquinoxaline, --,

CERTIFICATE OF CORRECTION (continued)
U.S. Pat. No. 10,454,037 B2

Column 96, Line 1, "poly(oxy-1," should read -- poly(oxy-1), --,

Column 96, Line 17, "TaO5," should read -- TaO$_5$, --,

Column 98, Line 2, "anorganic" should read -- an organic --,

Column 101, Line 53, "Di[4-" should read -- Di-[4- --,

Column 101, Line 54, "spirobifluoren," should read -- spiro-bifluoren, --,

Column 102, Line 4, "tetracyano-quinodimethan," should read -- tetracyanoquinodimethane, --, Column 102, Lines 5-6, "triphenylamin," should read -- triphenylamine, --, Column 102, Lines 7-8, "triphenylamin," should read -- triphenylamine, --, Column 102, Lines 9-10, "triphenylamin," should read -- triphenylamine, --, Column 102, Line 11, "triphenylamin," should read -- triphenylamine, --, Column 102, Lines 17-18, "diamin," should read -- diamine, --, Column 102, Line 24, "ethylenedioxythiophene)," should read -- ethylenedioxythiophene)), --, Column 102, Line 26, "(PTPD)" should read -- (PTPD)) --, Column 102, Line 27, "(P3HT)." should read -- (P3HT)). --, Column 102, Line 32, "(1994).)." should read -- (1994)). --, Column 103, Lines 44-45, should read -- robifluorene (spiro-MeOTAD), etc, and mixtures thereof. The organic materials may, if desired, be doped with a --, Column 103, Line 49, "tetracyanoquino-dimethane" should read -- tetracyanoquinodimethane --, Column 104, Line 3, "fro" should read -- from --, Column 104, Lines 21-23, should read -- amine B, cobaltocenes, etc. Inorganic materials suitable for use in a layer with electron conducting properties are preferably selected from --, Column 105, Line 3, "DCV5T)" should read -- DCV5T) --, Column 105, Line 37, "(HATI11)" should read -- (HAT11) --, Column 105, Line 53, "(DCV5T)" should read -- (DCV5T) --,

CERTIFICATE OF CORRECTION (continued)

Column 105, Line 64, "[2,1-b; 3,4-b']" should read -- [2,1-b;3,4-b'] --,

Column 106, Line 40, "fro" should read -- from --,

Column 106, Line 50, "on" should read -- one --,

Column 108, Line 45, "n-$C_3H_7$" should read -- n-$C_3F_7$ --,

Column 108, Line 63, "n-$C_3H_7$" should read -- n-$C_3F_7$ --,

Column 110, Line 22, "$C_3H_7$" should read -- $C_3F_7$ --,

Column 116, Line 9, "(6 r=4)" should read -- (ε r=4) --,

Column 116, Line 62, "N2," should read -- $N_2$, --,

Column 117, Line 26, "backgate" should read -- back gate --,

In the Claims

Column 123, Lines 32-36, Claim 5, " " should read -- 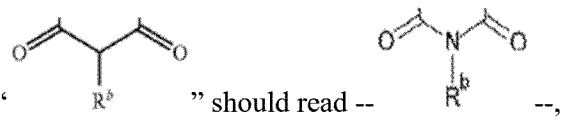 --,

Column 123, Line 55, Claim 7, "sec.-butyl," should read -- sec-butyl, --,

Column 123, Line 55, Claim 7, "tert.-" should read -- tert- --.